(12) United States Patent
Hartwig et al.

(10) Patent No.: US 7,732,365 B2
(45) Date of Patent: Jun. 8, 2010

(54) ENANTIOSELECTIVE AMINATION AND ETHERIFICATION

(75) Inventors: John F. Hartwig, Durham, CT (US); Chutian Shu, Danbury, CT (US); Toshimichi Ohmura, Nagaokakyo (JP); Christoph Kiener, Weisenheim am Sand (DE); Fernando Garcia Lopez, A Estrada Pontevedra (ES)

(73) Assignee: Yale University, New Haven, CT (US)

( * ) Notice: Subject to any disclaimer, the term of this patent is extended or adjusted under 35 U.S.C. 154(b) by 1057 days.

(21) Appl. No.: 10/527,899

(22) PCT Filed: Sep. 12, 2003

(86) PCT No.: PCT/US03/28718

§ 371 (c)(1),
(2), (4) Date: Mar. 16, 2006

(87) PCT Pub. No.: WO2004/024684

PCT Pub. Date: Mar. 25, 2004

(65) Prior Publication Data

US 2006/0199728 A1    Sep. 7, 2006

Related U.S. Application Data

(60) Provisional application No. 60/410,407, filed on Sep. 13, 2002, provisional application No. 60/445,154, filed on Feb. 5, 2003.

(51) Int. Cl.
| | |
|---|---|
| *B01J 31/00* | (2006.01) |
| *B01J 27/24* | (2006.01) |
| *B01J 27/00* | (2006.01) |
| *B01J 27/185* | (2006.01) |

(52) U.S. Cl. .................. 502/150; 502/152; 502/155; 502/162; 502/200; 502/208; 502/213

(58) Field of Classification Search .................. 502/150, 502/152, 155, 162, 200, 208, 213
See application file for complete search history.

(56) References Cited

U.S. PATENT DOCUMENTS 4,859,799 A    8/1989    Campestrini (Continued)

FOREIGN PATENT DOCUMENTS

| WO | WO 01/23088 | 5/2001 |
| WO | WO 02/04466 | 1/2002 |

OTHER PUBLICATIONS

Bartels, B. et al., *Eur. J. Inorg. Chem.* 2002,2569.

(Continued)

*Primary Examiner*—Jerry Lorengo
*Assistant Examiner*—James E McDonough
(74) *Attorney, Agent, or Firm*—Henry D. Coleman; R. Neil Sudol; William J. Sapone

(57) ABSTRACT

The present invention is directed to a catalyst composition, comprising: (1) a catalyst precursor having the general structure $MSX_n$ wherein M is a transition metal selected from the group consisting of iridium, molybdenum, and tungsten; S is a coordinating ligand; X is a counterion; and n is an integer from 0 to 5; and (2) a phosphoramidite ligand having the structure wherein $O-C_n-O$ is an aliphatic or aromatic diolate and wherein $R_1$, $R_2$, $R_3$ and $R_4$ are selected from the group consisting of substituted or unsubstituted aryl groups, substituted or unsubstituted heteroaryl groups, substituted or unsubstituted aliphatic groups, and combinations thereof, with the proviso that at least one of $R_1$, $R_2$, $R_3$, or $R_4$ must be a substituted or unsubstituted aryl or heteroaryl group. The present invention is also directed to activated catalysts made from the above catalyst composition, as well as methods of allylic amination and etherification using the above catalysts.

4 Claims, 4 Drawing Sheets

U.S. PATENT DOCUMENTS

| | | |
|---|---|---|
| 5,089,460 A | 2/1992 | Chien |
| 5,166,281 A | 11/1992 | Chamla et al. |
| 5,395,971 A | 3/1995 | Nicholas et al. |
| 5,817,877 A | 10/1998 | Hartwig et al. |
| 5,962,360 A | 10/1999 | Sivaram et al. |
| 5,977,361 A | 11/1999 | Hartwig et al. |
| 6,057,456 A | 5/2000 | Hartwig et al. |
| 6,072,073 A | 6/2000 | Kawatsura et al. |
| 6,100,398 A | 8/2000 | Hartwig et al. |
| 6,235,938 B1 | 5/2001 | Hartwig et al. |
| 6,384,282 B2 | 5/2002 | Hartwig et al. |
| 6,451,937 B1 | 9/2002 | Hartwig et al. |
| 6,562,989 B2 | 5/2003 | Hartwig et al. |
| 2003/0199713 A1 | 10/2003 | Berg Van Den et al. |

OTHER PUBLICATIONS

Herde, JL et al., *Inorg. Synth.* 1974, 15, 18.
Dondoni, A et al., *Synth. Commun.* 1994, 24, 2551.
Bartels, B. et al., Eur. J. Inorg. Chem. 2002, 2569-2586.
Ohmura, T. et al., J. Am. Chem. Soc. 2002, 124, 15164-15165.
Lopez, F. et al., J. Am. Chem. Soc. 2003, 125, 3426-3427.

ENANTIOSELECTIVE AMINATION AND ETHERIFICATION

CROSS-REFERENCE TO RELATED APPLICATIONS

This application claims the benefit of Provisional Application 60/410,407 filed Sep. 13, 2002, and Provisional Application 60/445,154 filed Feb. 5, 2003. These applications are incorporated by reference herewith in their entireties.

STATEMENT OF GOVERNMENT SUPPORT

This invention was made in part with government support under grant number GM-58108 from the National Institutes of Health of the United States Department of Health and Human Services. The U.S. Government has certain rights in this invention.

BACKGROUND OF THE INVENTION

1. Field of the Invention

The present invention relates to catalyzed enantioselective amination and etherification reactions and catalysts, and more specifically to iridium-catalyzed enantioselective amination and etherification of allylic esters with primary or secondary amines, phenoxides, or alkoxides, as well as catalyst complexes comprising iridium and a phosphoramidite ligand.

2. Brief Description of the Related Art

Transition metal-catalyzed allylic substitution is a powerful tool for the controlled formation of carbon-carbon and carbon-heteroatom bonds (Godleski, S. A.; Trost, B. M., Fleming, I., Eds.; Pergamon Press: New York, 1991; Vol. 4, pp 585-661). Most enantioselective versions of these reactions with carbon nucleophiles have been reported with Pd (Jacobsen, E. N. et al., *Comprehensive Asymmetric Catalysis I-III*; Springer-Verlag: Berlin, Germany, 1999), but enantioselective allylic alkylation has also been reported with Mo (Trost, B. M.; Hachiya, I. *J. Am. Chem. Soc.* 1998, 120, 1104; Trost, B. M.; Hildbrand, S.; Dogra, K. *J. Am. Chem. Soc.* 1999, 121, 10416; Malkov, A. V.; Baxendale, I. R.; Dvorak, D.; Mansfield, D. J.; Kocovsky, P. *joc* 1999, 64, 2737), W (Lloyd-Jones, G. C.; Pfaltz, A. *Angew. Chem., Int. Ed.* 1995, 34, 462; Malkov, A. V.; Baxendale, I. R.; Dvorak, D.; Mansfield, D. J.; Kocovsky, P. *joc* 1999, 64, 2737), and, most recently, Ir catalysts (Takeuchi, R. *Synlett* 2002, 1954; Takeuchi, R.; Ue, N.; Tanabe, K.; Yamashita, K.; Shiga, N. *J. Am. Chem. Soc.* 2001, 123, 9525; Bartels, B.; Garcia-Yebra, C.; Rominger, F.; Helmchen, G. *Eur. J. Inorg. Chem.* 2002, 2569). However, despite the importance of optically active allylic amines and ethers, few enantioselective allylic aminations and etherifications by reactions of heteroatom nucleophiles have been described.

Enantioselective routes to optically active amines can provide valuable synthetic building blocks. The enantioselective preparation of chiral tertiary amines is particularly important because they cannot be generated directly by enantioselective hydrogenation of imines, and the enantioselective hydrogenation of enamines remains a challenge. In addition, methods for enantioselective coupling of two fragments by C—N bond-formation are limited.

Allylic substitution of acyclic allylic electrophiles catalyzed by W, Mo, Ru, Ir, and Rh complexes often generate the chiral branched substitution products. Enantioselective amination of symmetrical 1,3-diphenylallyl carbonates and unsymmetrical branched allylic acetates along with a few examples of palladium-catalyzed asymmetric amination of a terminal allylic ester or carbonate have been reported (Hayashi, T. et al., *J. Am. Chem. Soc.* 1989, 111, 6301-6311; You, S. et al., *J. Am. Chem. Soc.* 2001, 123, 7471; Hayashi, T. et al., *Tetrahedron Lett.* 1990, 31, 1743-1746; Johannsen, M.; Jørgensen, K. A. *Chem. Rev.* 1998, 98, 1689-1708). Takeuchi (Takeuchi, R.; et al., *J. Am. Chem. Soc.* 2001, 123, 9525-9534) and Evans (Evans, P. A.; et al., *J. Am. Chem. Soc.* 1999, 121, 6761-6762) have shown that iridium and rhodium complexes of achiral phosphites catalyze the formation of branched amines, in some cases with conservation of enantiomeric excess. Helmchen reported enantioselective alkylation of branched allylic acetates with modest levels of enantiomeric excess (ee) (Bartels, B.; Helmchen, G. *Chem. Commun.* 1999, 741-742) in the presence of an iridium-phosphoramidite catalyst. Analogous enantioselective aminations occurred with ee's below 15%. A general, enantioselective allylic amination from an achiral, terminal allylic electrophile has not been accomplished.

Aryl ethers are common subunits of biologically active molecules. Apart from their use as precursors for the Claisen rearrangement (Wipf, P.; Trost, B. M., Fleming, I., Paquette, L. A., Eds.; Pergamon press: Oxford, 1991; Vol. 5, pp 827-874; Larock, R. C. *Comprehensive Organic Transformations: A Guide to Functional Group Preparations*; VCH Publishers, Inc: New York, 1989), aryl allyl ethers have not been used extensively as building blocks for natural product synthesis because methods for their enantioselective construction are limited. Two reports of stereospecific allylic etherification of branched carbonates catalyzed by Ru (Trost, B. M.; Fraisse, P. L.; Ball, Z. T. *Angew. Chem., Int. Ed.* 2002, 41, 1059) and Rh (Evans, P. A.; Leahy, D. K. *J. Am. Chem. Soc.* 2000, 122, 5012; Evans, P. A.; Leahy, D. K. *J. Am. Chem. Soc.* 2002, 124, 7882) were reported recently, and a few enantioselective palladium-catalyzed examples have been reported (Trost, B. M.; Toste, F. D. *J. Am. Chem. Soc.* 1995, 121, 4545; Trost, B. M.; Toste, F. D. *J. Am. Chem. Soc.* 1998, 120, 815; Trost, B. M.; Tsui, H.-C.; Toste, F. D. *J. Am. Chem. Soc.* 2000, 122, 3534). Elegant applications of the palladium-catalyzed chemistry for the synthesis of natural products demonstrates the potential of these building blocks in organic synthesis (Trost, B. M.; Toste, F. D. *J. Am. Chem. Soc.* 1998, 120, 9074; Trost, B. M.; Toste, F. D. *J. Am. Chem. Soc.* 2000, 122, 11262; Trost, B. M.; Thiel, O. R.; Tsui, H.-C. *J. Am. Chem. Soc.* 2002, 124, 11616; Trost, B. M.; Tang, W. *J. Am. Chem. Soc.* 2002, 124, 14542) Thus, new, more general, enantioselective methods for the construction of allylic ethers would be synthetically valuable.

International Patent Publication WO 02/04466 discloses catalysts for asymmetric transfer hydrogenation, including a transition metal selected from rhodium and ruthenium, and a phosphoramidite ligand. This publication also discloses processes for the asymmetric transfer hydrogenation of an olefinically unsaturated compound, ketone, imine or oxime derivative in the presence of a hydrogen donor and a catalyst, wherein the catalyst includes a transition metal selected from rhodium, ruthenium, and iridium, and a ligand.

International Patent Publication WO 01/23088 discloses catalysts for asymmetric transfer hydrogenation using a transition metal catalyst and a nitrogen-containing enantiomerically enriched ligand, as well as processes for the preparation of enantiomerically enriched compounds using such catalysts. According to the invention, the transition metal is iridium, ruthenium, rhodium or cobalt, and the enantiomerically enriched ligand contains sulfur in the form of a thioether or a sulfoxide.

Bartels et al., (Bartels, B.; Garcia-Yebra, C.; Rominger, F.; Helmchen, G. *Eur. J. Inorg. Chem.* 2002, 2569-2586) discloses Ir-catalysed allylic alkylations of enantiomerically enriched monosubstituted allylic acetates using P(OPh)$_3$ as ligand. Lithium N-tosylbenzylamide was identified as a suitable nucleophile for allylic aminations.

What is needed in the art are catalysts and processes for enantioselective and regioselective reactions of terminal allylic electrophiles with compounds containing N—H or O—H bonds such as aliphatic amines, benzylamines, aromatic amines, phenoxides, or alkoxides, to produce optically active, branched allylic ethers or amines. The present invention is believed to be an answer to that need.

SUMMARY OF THE INVENTION

In one aspect, the present invention is directed to a catalyst composition, comprising (1) a catalyst precursor having the general structure MSX$_n$ wherein M is a transition metal selected from the group consisting of iridium, molybdenum, and tungsten; S is a coordinating ligand; X is a counterion; and n is an integer from 0 to 5; and (2) a phosphoramidite ligand having the structure

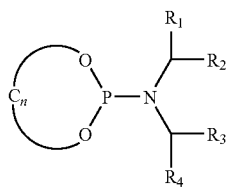

wherein O—C$_n$—O is an aliphatic or aromatic diolate and wherein R$_1$, R$_2$, R$_3$, and R$_4$ are selected from the group consisting of substituted or unsubstituted aryl groups, substituted or unsubstituted heteroaryl groups, substituted or unsubstituted aliphatic groups, and combinations thereof, with the proviso that at least one of R$_1$, R$_2$, R$_3$, or R$_4$ must be a substituted or unsubstituted aryl or heteroaryl group.

In another aspect, the present invention is directed to an activated catalyst, comprising a cyclometallated phosphoramidite having the structure

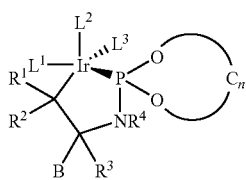

wherein O—C$_n$—O is an aliphatic or aromatic diolate; B is any substituted or unsubstituted aryl or heteroaryl group; R$^1$, R$^2$, R$^3$, and R$^4$ are independently selected from hydrogen, alkyl, benzylic and aromatic or heteroaromatic groups; L$^1$ and L$^2$ are any ligands bound to Ir through an electron pair or through electrons in a pi-system of an unsaturated moiety; and L$^3$ is an optional ligand selected from the group consisting of phosphine, phosphite, phosphoramidite, amine, heterocycle, carbon monoxide, and combinations thereof.

In another aspect, the present invention is directed to a method of making an activated catalyst, the activated catalyst comprising a cyclometallated phosphoramidite, comprising the step of combining a catalyst precursor and a phosporamadite ligand in the presence of a base under conditions that form the activated catalyst.

In yet another embodiment, the present invention is directed to a method of preparing allylic amines enantioselectively, the method comprising the steps of reacting (a) an achiral or racemic allylic ester, allylic carbonate or allylic halide; (b) a reactant containing an N—H bond or a salt thereof, excluding lithium salts of N-benzyltosylamides; and (c) an optional additive selected from a base and a metal salt, the reacting step taking place in the presence of a solvent and a catalyst composition, the catalyst composition comprising a transition metal selected from the group consisting of iridium, rhodium, molybdenum, and tungsten, the reacting step taking place under conditions that enantioselectively form allylic amines.

In yet another aspect, the present invention is directed to a method of preparing allylic amines enantioselectively, the method comprising the steps of reacting (a) an achiral or racemic allylic ester, allylic carbonate or allylic halide; and (b) a reactant containing an N—H bond or a salt thereof, in the presence of a solvent and a catalyst composition, the catalyst composition comprising (1) a catalyst precursor having the general structure MSX$_n$ wherein M is a transition metal selected from the group consisting of iridium, molybdenum, and tungsten; S is a coordinating ligand; X is a counterion; and n is an integer from 0 to 5; and (2) a phosphoramidite ligand having the structure

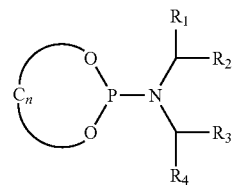

wherein O—C$_n$—O is an aliphatic or aromatic diolate and wherein R$_1$, R$_2$, R$_3$, and R$_4$ are selected from the group consisting of substituted or unsubstituted aryl groups, substituted or unsubstituted heteroaryl groups, substituted or unsubstituted aliphatic groups, and combinations thereof, with the proviso that at least one of R$_1$, R$_2$, R$_3$, or R$_4$ must be a substituted or unsubstituted aryl or heteroaryl group; under conditions that enantioselectively form allylic amines.

In yet another aspect, the present invention is directed to a method of preparing allylic ethers enantioselectively, the method comprising the steps of reacting (a) an achiral or racemic allylic ester, allylic carbonate or allylic halide (b) a reactant containing an O—H bond, and (c) optionally, a base; the reacting step taking place in a solvent and in the presence of a catalyst composition, the catalyst composition comprising a transition metal selected from the group consisting of iridium, rhodium, ruthenium, molybdenum, and tungsten, the reacting step taking place under conditions that enantioselectively form allylic ethers.

In yet another aspect, the present invention is directed to a method of preparing allylic ethers enantioselectively, the method comprising the steps of reacting (a) an achiral or racemic allylic ester, allylic carbonate or allylic halide and (b) a reactant containing an O—H bond, or a salt thereof, the reacting step taking place in a solvent and in the presence of a catalyst composition, the catalyst composition comprising (1) a catalyst precursor having the general structure MSX$_n$ wherein M is a transition metal selected from the group consisting of iridium, molybdenum, and tungsten; S is a coordinating ligand; X is a counterion; and n is an integer from 0 to 5; and (2) a phosphoramidite ligand having the structure

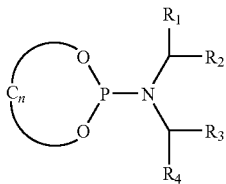

wherein O—C$_n$—O is an aliphatic or aromatic diolate and wherein R$_1$, R$_2$, R$_3$, and R$_4$ are selected from the group consisting of substituted or unsubstituted aryl groups, substituted or unsubstituted heteroaryl groups, substituted or unsubstituted aliphatic groups, and combinations thereof, with the proviso that at least one of R$_1$, R$_2$, R$_3$, or R$_4$ must be a substituted or unsubstituted aryl or heteroaryl group; under conditions that enantioselectively form allylic ethers.

These and other aspects will become apparent upon reading the following detailed description of the invention.

BRIEF DESCRIPTION OF THE FIGURES

The invention will be more fully understood from the following detailed description taken in conjunction with the accompanying drawings in which.

DETAILED DESCRIPTION OF THE INVENTION

Figure 1:
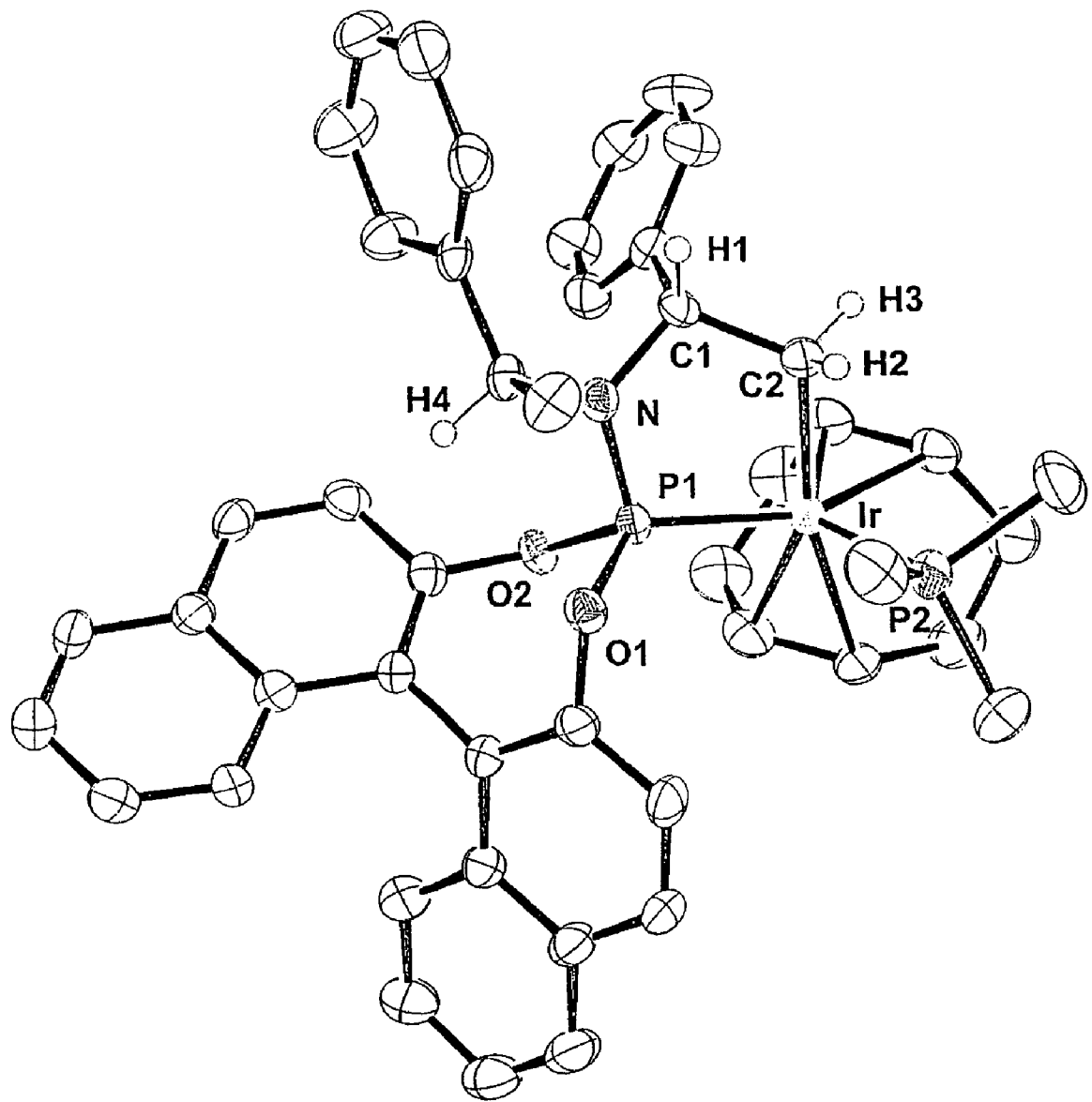
FIG. 1 depicts the molecular structure of a phosphoramidite-iridium catalyst complex of the invention.

Applicants have unexpectedly discovered that catalysts made from a transition metal-containing catalyst precursor and a phosphoramidite ligand are capable of catalyzing production of allylic amines and allylic esters with high regio- and enantioselectivity. The amination and etherification catalysts and methods of the present invention are believed to be the first enantioselective processes with a metal other than palladium that converts terminal allylic esters or carbonates to branched materials as the major product. The catalysts and methods of the present invention are useful in the preparation of materials containing a terminal olefin group. Such products may be used as precursors to generate other useful products, for example, 1,3-amino alcohols, 1,3-diamines, and various types of amino acids. Such products are useful in the chemical and pharmaceutical industries.

For the purposes of this application, the term "ester" includes compounds containing an oxygen bound to a carbon, phosphorus or sulfur that is bound to an additional oxygen through a multiple bond or a compound containing an oxygen bound to boron that is bound to two additional oxygen atoms.

As indicated above, the catalyst composition of the present invention comprises (1) a catalyst precursor having the general structure MSX$_n$ wherein M is a transition metal selected from the group consisting of iridium, molybdenum, and tungsten; S is a coordinating ligand; X is a counterion; and n is an integer from 0 to 5; and (2) a phosphoramidite ligand having the structure

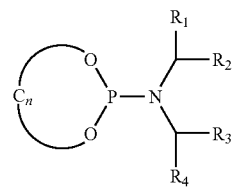

wherein O—C$_n$—O is an aliphatic or aromatic diolate and wherein R$_1$, R$_2$, R$_3$, and R$_4$ are selected from the group consisting of substituted or unsubstituted aryl groups, substituted or unsubstituted heteroaryl groups, substituted or unsubstituted aliphatic groups, and combinations thereof. Preferably, at least one of R$_1$, R$_2$, R$_3$, or R$_4$ is a substituted or unsubstituted aryl or heteroaryl group. Each of these components is discussed in more detail below.

Transition metals useful in the catalyst precursor component of the invention include iridium, tungsten, molybdenum, ruthenium, and rhodium. Preferably the transition metal is iridium, tungsten, or molybdenum, and most preferably, iridium.

The catalyst precursor has a general structure MSX$_n$, where S is a coordinating ligand for the transition metal M. Useful coordinating ligands S include, but are not limited to, ethylene, maleic anhydride, 1,5-cyclooctadiene, cyclooctene, 1,3-butadiene, 2,5-norbornadiene, benzene, hexamethyl benzene, cymene, cumene, cyclopentadiene, pentamethylcyclopentadiene, 1,2-diaminoethane, (R,R)-1,2 cyclohexanediamine, (S,S)-1,2-diphenyl-1,2-diaminoethane, (S,S)-1,2-dicyclohexyl-1,2-diaminoethane, and (S)-1,1'-bis-(p-methoxyphenyl)-1,2-propanediamine. Particularly useful coordinating ligands S are 1,5-cyclooctadiene (abbreviated as COD) and 2,5-norbornadiene. It will be understood that alternative enantiomers (R) and (S) of the above coordinating ligands may also be used. Further, as will be appreciated by one skilled in the art, combinations of the aforementioned coordinating ligands may also be implemented in the catalysts and methods of the present invention.

In the catalyst precursor, X is counterion which may be anionic or cationic. Useful counterions include, but are not limited to, Cl, Br, I, acetate, BF$_4$, PF$_6$, ClO$_4$, p-toluene sulfonate, benzene phosphonate, tetra-pentafluorophenylborate, Li, Na, K, Mg, Ca, ammonium, and alkyl-substituted ammonium. Like the coordinating ligands, combinations of counterions X may be implemented in the catalysts and methods of the present invention. The number of X counterions (n) in the MSX$_n$ catalyst precursor is sufficient to counterbalance the charge on the complex. Preferably, n can range from zero (0) to five (5). In a preferred embodiment, the catalyst precursor has the structure [(COD)IrCl]$_2$. The catalyst precursors may be made using published procedures known in the art, such as those described in Herde et al., Inorg. Synth. 15:18 (1974), herein incorporated by reference in its entirety.

The phosphoramidite portion of the catalyst composition of the invention may be any phosphoramidite, such as those disclosed in International Patent Application Publication WO 02/04466, which is hereby incorporated by reference in its entirety. Preferably, the phosphoramidite ligand has the general structure

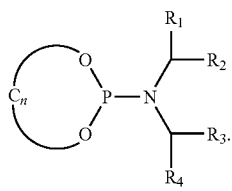

In this structure, O—$C_n$—O is an aliphatic or aromatic diolate. $R_1$, $R_2$, $R_3$, and $R_4$ are preferably substituted or unsubstituted aryl groups, substituted or unsubstituted heteroaryl groups, substituted or unsubstituted aliphatic groups, or combinations of such groups. However, at least one of $R_1$, $R_2$, $R_3$, or $R_4$ must be a substituted or unsubstituted aryl or heteroaryl group.

In one embodiment, a preferred O—$C_n$—O group is an aromatic group having the general structure

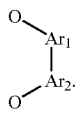

In this general structure, $Ar_1$ amd $Ar_2$ are individually aryl, substituted aryl, or heteroaryl. Examples of useful O—$C_n$—O groups having this general structure include, but are not limited to the following:

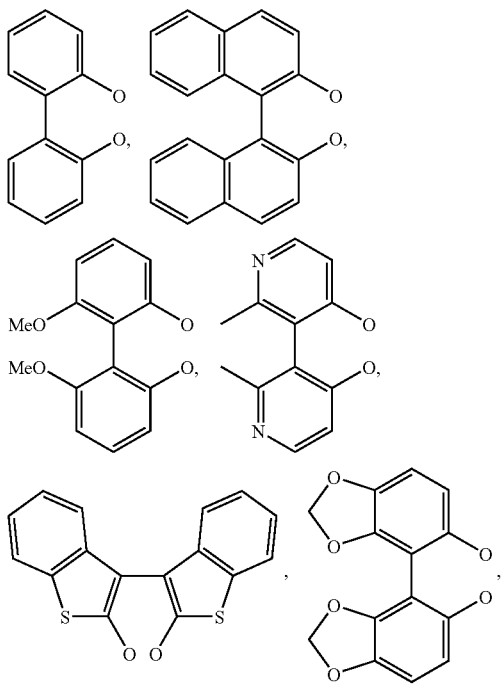

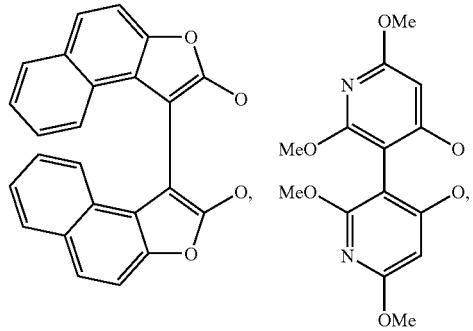

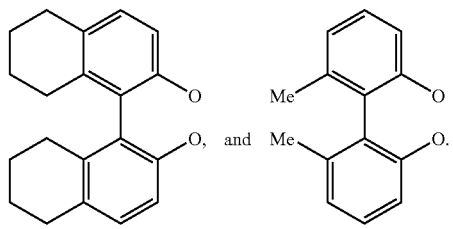

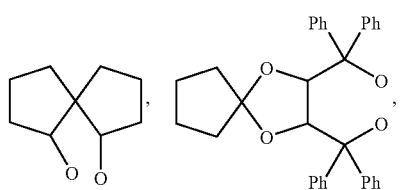

It will be understood by those skilled in the art that these structures may be in any combination of R or S enantiomers, and that both enantiomers may be implemented in the present invention.

In an alternative preferred embodiment, the O—$C_n$—O group is an aliphatic group. Examples of useful aliphatic groups include, but are not limited to, 2,3-butanediol, 1,2-propanediol, 2-phenylethylene glycol, or compounds having the following structures:

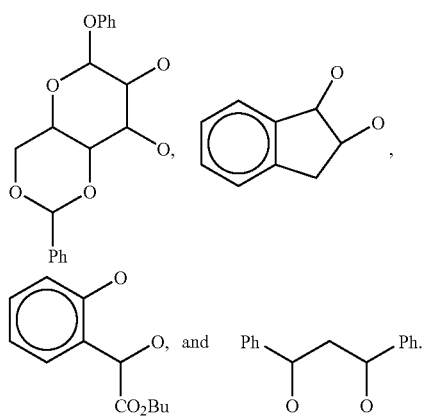

In the general structure above, O—C$_n$—O is preferably a substituted or unsubstituted moiety having the structures:

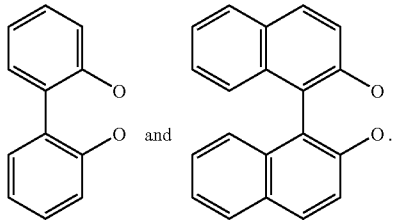

Particularly useful phosphoramidite ligands include various diastereomers of the phosphoramidites having the structures

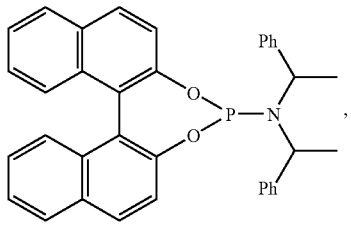
(L1)

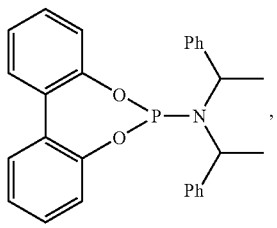
(L2)

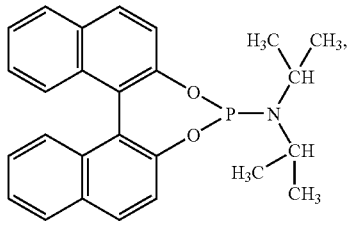
(L3)

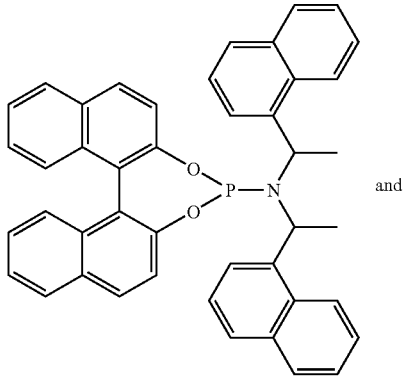
(L4)

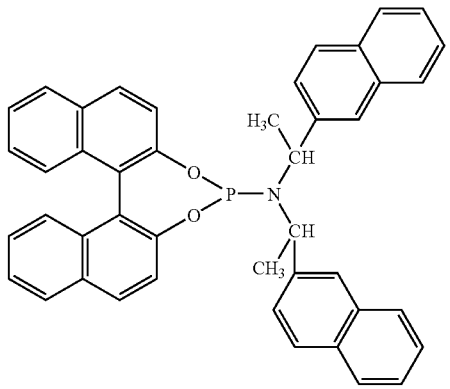
(L5)

The phosphoramidites of the present invention may be produced using know procedures, such as those described by Alexakis et al. (Alexakis, A. et al., Synlett (2001), 1375), which is herein incorporated by reference in its entirety.

As discussed in more detail below, several diastereomers of the ligands can be prepared, and the catalytic process can be conducted with pure diastereomers of the ligands or mixtures of diastereomeric forms of the ligand. These diastereomeric ligands generate catalysts with different activities, and the optimal configuration of the diastereomer can depend on the substrate combination. For example, S or R binaphthol can be combined with the R,R-enantiomer of the amine to generate two diastereomeric forms of the ligand and, after coordination to the metal atom, diastereomeric catalysts. In addition, several diastereomeric forms of the activated catalyst can result from the combination of ligand stereochemistry and stereochemistry of the metal center. Several of these diastereomers are likely to undergo interconversion faster than the catalytic reaction occurs, and the catalyst may, therefore, react though one or more diastereomeric forms of the catalyst regardless of the diastereomer that is isolated.

In one preferred embodiment, the catalyst composition of the present invention includes [(COD)IrCl]$_2$ as the catalyst precursor, and a phosphoramidite ligand having the structure

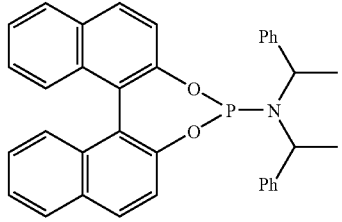

The catalyst precursor and phosphoramidate ligand of the catalyst composition form a catalyst for allylic amination or etherification of achiral or racemic allylic esters in situ (e.g., in the vessel where the allylic amination or etherification is occurring).

Amination Reaction

In one embodiment, the present invention is directed to a general method of preparing allylic amines enantioselectively. The method comprises the steps of reacting (a) an achiral or racemic allylic ester, allylic carbonate or allylic halide; and (b) a reactant containing an N—H bond or a salt thereof, excluding lithium salts of N-benzyltosylamides, in the presence of a solvent and a catalyst composition. The catalyst composition may be any catalyst composition that contains a transition metal selected from the group consisting of iridium, rhodium, molybdenum, and tungsten.

The catalyst for the above general reaction preferably comprises (1) a catalyst precursor having the general structure $MSX_n$ wherein M is the above transition metal; S is a coordinating ligand; X is a counterion; and n is an integer from 0 to 5; and (2) a phosphoramidite ligand having the structure

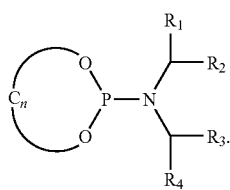

In the above structure, $O—C_n—O$ is an aliphatic or aromatic diolate and $R_1$, $R_2$, $R_3$, and $R_4$ are selected from the group consisting of substituted or unsubstituted aryl groups, substituted or unsubstituted heteroaryl groups, substituted or unsubstituted aliphatic groups, and combinations thereof. However, at least one of $R_1$, $R_2$, $R_3$, or $R_4$ must be a substituted or unsubstituted aryl or heteroaryl group.

In a preferred embodiment, the present invention is further directed to methods of preparing allylic amines enantioselectively, wherein the method comprises the step of reacting an achiral or racemic allylic ester, allylic carbonate or allylic halide; and a reactant containing an N—H bond, or a salt thereof, in the presence of a solvent and the above catalyst composition. The present inventors have unexpectedly discovered that Ir-phosphoramidite complexes display higher activity than phosphite complexes for allylic amination, and that branched products were formed with high enantioselectivity (Scheme 1).

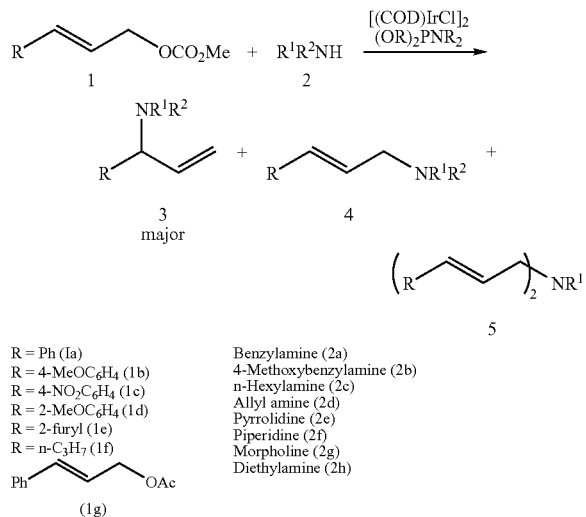

The phosphoramidite complex catalyzed allylic amination to form the product 3 shown in Scheme 1. In the presence of 2 mol % [Ir(cod)Cl]$_2$ and phosphoramadite structure (1) above, the reaction of cinnamyl methylcarbonate (compound 1a in Scheme 1) with morpholine (2 g) (3.0 equiv) occurred to completion and with excellent regioselectivity (ratio of products 3 and 4 was 99/1) at room temperature.

As indicated above, one reactant in the method of the present invention is an achiral or racemic allylic ester, an achiral or racemic allylic carbonate, or an achiral or racemic halide. Useful achiral or racemic allylic esters are preferably selected from the group consisting of: Ph-CH=CH—CH$_2$—OAc, 4-MeO—C$_6$H$_4$—CH=CH—CH$_2$—OAc, 4-NO$_2$—C$_6$H$_4$—CH=CH—CH$_2$—OAc, 2-MeO—C$_6$H$_4$—CH=CH—CH$_2$—OAc, 2-furyl-CH=CH—CH$_2$—OAc, n-C$_3$H$_7$—CH=CH—CH$_2$—OAc, Me-CH=CH—CH$_2$—OAc, n-Pr—CH=CH—CH$_2$—OAc, i-Pr—CH=CH—CH$_2$—OAc, and CH$_3$—CH=CH—CH=CH—CH$_2$—OAc. As will be appreciated by those skilled in the art, combinations of the above achiral allylic esters may also be implemented in the method of the invention.

Useful achiral or racemic allylic carbonates that may be implemented in the method of the invention include Ph-CH=CH—CH$_2$—OCOOMe, 4-MeO—C$_6$H$_4$—CH=CH—CH$_2$—OCOOMe, 4-NO$_2$—C$_6$H$_4$—CH=CH—CH$_2$—OCOOMe, 2-MeO—C$_6$H$_4$—CH=CH—CH$_2$—OCOOMe, 2-furyl-CH=CH—CH$_2$—OCOOMe, n-C$_3$H$_7$—CH=CH—CH$_2$—OCOOMe, Me-CH=CH—CH$_2$—OCOOMe, n-Pr—CH=CH—CH$_2$—OCOOMe, i-Pr—CH=CH—CH$_2$—OCOOMe, and CH$_3$—CH=CH—CH$_2$—OCOOMe. Combinations of the above achiral allylic carbonates may also be implemented.

Notwithstanding the above examples, it will be appreciated by those skilled in the art that other esters and carbonates can be used in the present invention, besides acetate and methyl carbonates shown above. For example, ethyl, t-butyl phenyl, or other suitable aliphatic or aromatic group could replace methyl.

Useful achiral or racemic allylic halides that may be implemented in the method of the invention include Ph-CH=CH—CH$_2$—X, 4-MeO—C$_6$H$_4$—CH=CH—CH$_2$—X, 4-NO$_2$—C$_6$H$_4$—CH=CH—CH$_2$—X, 2-MeO—C$_6$H$_4$—CH=CH—CH$_2$—X, 2-furyl-CH=CH—CH$_2$—X, n-C$_3$H$_7$—CH=CH—CH$_2$—X, Me-CH=CH—CH$_2$—X, n-Pr—CH=CH—CH$_2$—X, i-Pr—CH=CH—CH$_2$—X, and CH$_3$—CH=CH—CH=CH—CH$_2$—X, wherein X is selected from a halide atom such as F, Cl, Br, and I.

Generally, useful reagents containing an N—H bond include ammonia, aromatic or aliphatic primary or secondary amines, amides, carbamates, sulfonamides, imides, phosphoramides, imines, silylamines, heterocycles, and combinations and salts thereof. More specific examples of useful reagents with N—H bonds that may be used in the method of the invention include ammonia, aromatic or aliphatic primary or secondary amines such as substituted or unsubstituted anilines, diphenylmethylamine, benzylamines, 4-methoxybenzylamine; primary alkylamines such as n-hexylamine and allyl amines; secondary cyclic amines such as pyrrolidine, piperidine, and morpholine; acyclic secondary amines such as diethylamine; and non-amine substrates like Boc$_2$NLi, LiN(CHO)$_2$, benzphenone imine, and tosylamide. Suitable mixtures of the above amine compounds may also be implemented.

Additional additives, such as metal salts (e.g., copper or zinc salts), metal halides (e.g., copper chloride or zinc chloride), 1,4-diazabicyclo(2.2.2)octane (DABCO), and the like, as well as various combinations of these, may also be implemented in the present invention. Particularly useful additives are those that function as bases, including, but not limited to triethylamine or other tertiaryl alkylamines, cyclic tertiaryamines such as 1,4-diazabicyclo(2.2.2)octane (DABCO), and imines such as diazabicycloundecane.

In general, the reaction conditions for the amination method of the present invention include reaction temperatures ranging from 20 to 60° C., and reaction times ranging from 1 to 96 hours. Generally, the ratio of the amounts of phosphoramidite ligand to catalyst precursor is approximately 2:1, and the enantiomeric excess (ee) of said method is typically greater than approximately 70%.

Solvent can influence the reactivity, regioselectivity, and enantioselectivity of the reaction scheme. Useful solvents for the amination reaction include DMF, ethanol, methanol, THF, acetonitrile, $CH_3NO_2$, DME, $CH_2Cl_2$, triethylamine, 1,4-dioxane, diethyl ether, toluene, hexane, and combinations thereof. The reactivity at room temperature followed the order DMF, EtOH>MeOH, THF, $CH_3CN>CH_3NO_2$, DME>$CH_2Cl_2$, $Et_3N$>1,4-dioxane, $Et_2O$, toluene. Reactions in each solvent occur with high regioselectivity (ratio of products 3/4/5=98-94/1-4/0-3) except for those in $Et_3N$ and $CH_3NO_2$. The enantioselectivity of reactions in different solvents followed the order: THF, $Et_2O$, DME>toluene, 1,4-dioxane, $CH_2Cl_2$>$Et_3N$>DMF, EtOH, $CH_3CN>CH_3NO_2$>MeOH. Reactions in the polar solvents DMF, EtOH, and MeOH were fast, but lower ee's were observed. Reactions in THF (tetrahydrofuran) displayed the most suitable balance of rate and enantioselectivity.

The effect of ligand and temperature on selectivity is summarized in Table 1.

Product yields were isolated after silica gel chromatography. Enantiomeric excesses (ee) were determined by HPLC.

As shown in Table 1, the reaction proceeded smoothly at room temperature in the presence of $[Ir(cod)Cl]_2$ (1 mol %) and phosphoramidite ligand 1 above (2 mol %, L/Ir=1) to give after 10 h branched product 3 in 84% isolated yield with excellent regioselectivity (3/4/5=98/1/1) and 95% enantiomeric excess (entry 1). Reaction at 50° C. for 4 h gave 89% of product 3 with 94% ee (entry 2). Reactions catalyzed by complexes of the diastereomeric form of phosphoramidite ligand L1 with opposite relative configuration of the binaphthol and amine unit were slow, even at 50° C., and formed the opposite enantiomer in 66% yield and 75% ee (entry 3). Complexes of binaphthol-derived ligands with achiral and smaller substituents at nitrogen (e.g., phosphoramidite ligand L3) produced lower ee's than did those of phosphoramidite ligand L1 (entry 4). Phosphoramidite ligand L2 with a biphenol unit gave product with a lower, though substantial enantioselectivity of 87% (entry 5).

The scope of the allylic amination catalyzed with the combination of phosphoramidite ligand L1 and $[Ir(cod)Cl]_2$ as a catalyst, and in the absence of a base, is summarized in Table 2.

TABLE 2

Enantioselective Allylic Amination Catalyzed by Phosphoramidite Ligand 1 and $[Ir(cod)Cl]_2$

| Entry | Allyl Carbonate | Amine | Time (h) | Ratio 3/4/5 | Yield of Product 3 | % ee |
|---|---|---|---|---|---|---|
| 1 | Ph—CH=CH—$CH_2$—OCOOMe | 4-methoxybenzylamine | 18 | 99/0/1 | 80 | 94 (−) |
| 2 | Ph—CH=CH—$CH_2$—OCOOMe | n-hexylamine | 9 | 98/2/0 | 88 | 96 (R) |
| 3 | Ph—CH=CH—$CH_2$—OCOOMe | allyl amine | 12 | na | 76 | 97 (−) |
| 4 | Ph—CH=CH—$CH_2$—OCOOMe | pyrrolidine | 2 | 98/2 | 75 | 97 (−) |
| 5 | Ph—CH=CH—$CH_2$—OCOOMe | Piperidine | 10 | 97/3 | 91 | 96 (−) |
| 6 | Ph—CH=CH—$CH_2$—OCOOMe | Morpholine | 24 | 99/1 | 92 | 97 (−) |
| 7 | Ph—CH=CH—$CH_2$—OCOOMe | Diethylamine | 16 | 98/2 | 83 | 97 (−) |
| 8 | 4-MeO—$C_6H_4$—CH=CH—$CH_2$—OCOOMe | Benzylamine | 9 | 99/1/0 | 88 | 96 (−) |
| 9 | 2-MeO—$C_6H_4$—CH=CH—$CH_2$—OCOOMe | Benzylamine | 16 | 95/4/1 | 77 | 76 (−) |
| 10 | 2-furyl-CH=CH—$CH_2$—OCOOMe | Benzylamine | 10 | 96/2/2 | 58 | 97 (+) |
| 11 | n-$C_3H_7$—CH=CH—$CH_2$—OCOOMe | Benzylamine | 10 | 88/8/4 | 66 | 95 (+) |
| 12 | Ph—CH=CH—$CH_2$—OAc | Benzylamine | 16 | 97/3/0 | 95 | 95 (−) |
| 13 | Ph—CH=CH—$CH_2$—OAc | Morpholine | 72 | 96/4 | 87 | 96 (−) |

TABLE 1

Ligand and Temperature Effects for Ir-Catalyzed Enantioselective Allylic Amination of Ph—CH=CH—$CH_2$—OCOOMe with Benzylamine

| Entry | Ligand | Temp. (° C.) | Time (h) | Ratio (3/4/5) | Yield of Product 3 (%) | % ee |
|---|---|---|---|---|---|---|
| 1 | L1 | 25 | 10 | 98/1/1 | 84 | 95 (R) |
| 2 | L1 | 50 | 4 | 98/2/0 | 89 | 94 (R) |
| 3 | L1 | 50 | 72 | 93/6/1 | 66 | 75 (S) |
| 4 | L3 | 50 | 72 | 72/23/5 | 25 | 61 (R) |
| 5 | L2 | 25 | 48 | 96/2/2 | 72 | 87 (R) |

In Table 1, the reaction was conducted with 1 mmol of Ph-CH=CH—$CH_2$—OCOOMe and 1.2-1.3 mmol of benzylamine in THF (0.5 mL) in the presence of 0.01 mmol of $[Ir(cod)Cl]_2$ and 0.02 mmol of selected phosphoramidite ligand unless otherwise noted. Product ratios were determined by $^1H$ NMR spectroscopy of crude reaction mixtures.

In Table 2, the reaction was conducted at room temperature with 0.02 mmol phosphoramidite ligand L1 as noted in Table 1. Ratios of products 3, 4, and 5, were determined by $^1H$ NMR spectra of crude mixtures. Yield of product 3 was determined by isolation using silica gel chromatography. Enantiomeric excess (ee) was determined by HPLC. The reaction of Entry 7 was conducted at 50° C. In Entry 9, 2.0 equiv of benzylamine was used. In Entry 13, the reaction was conducted in EtOH with 3.0 equiv of benzylamine. The reaction in Entry 14 was conducted neat with 3.0 equiv. of morpholine.

As shown in Table 2, reactions of Ph-CH=CH—$CH_2$—OCOOMe with primary amines such as 4-methoxybenzylamine, n-hexylamine, and allylamine gave the corresponding branched allylic amine with high selectivity over the isomeric or diallylamine (entries 1-3) and with enantioselectivities from 94 to 97%. Cyclic secondary amines, such as pyrrolidine, piperidine, and morpholine, reacted at room temperature (entries 4-6) to form the branched allylic amines with enantioselectivities between 96 and 97%. The acylic diethylamine reacted at 50° C. to form the branched product in high yield and 97% ee (entry 7).

Other aromatic and heteroaromic derivatives of cinnamyl carbonate also reacted with benzylamine in high yield and enantioselectivity. p-Methoxy-cinnamyl methyl carbonate reacted with benzylamine to form a branched product with 88% yield and 96% ee (entry 8). The furanyl analog of cinnamyl carbonate formed a product in acceptable yield and excellent enantioselectivity (entry 10). Significantly, the complex of phosphoramidite ligand L1 and [Ir(cod)Cl]$_2$ catalyzed the allylic amination of (E)-2-hexenyl methyl carbonate (entry 11) with high enantioselectivity. Although the yield was moderate because of slightly lower regioselectivity, the enantiomeric excess was 95%. The reaction also occurred with cinnamyl acetate 1 g in ethanol (entry 12) or neat (entry 13) with 3.0 equiv of amine to form the allylic amine in good yield and with excellent enantioselectivity. Two terminal carbonates reacted less selectively. o-Methoxy-substituted cinnamyl carbonate reacted with high regioselectivity, but the branched product formed with only 76% ee (entry 9). Branched allylic carbonates have, thus far, reacted to give low ee's of branched allylic amine after full conversion.

The following Tables show the broad scope of the reaction of the allylic carbonates with aromatic amines, such as aniline, in the presence of an additional additive such as DABCO. While not wishing to be bound by any theory, it is believed that the additional additive may function to activate the catalyst and place it in a more reactive form.

TABLE 3a

Allylic Amination of Methyl Allylic Carbonates with Anilines.

| Carbonates | Anilines | Ligand | Conditions | Yield (B/L) | Ee |
|---|---|---|---|---|---|
| Ph-OCOOMe | PhNH$_2$ | L1 (2%) | DABCO (50%) rt, 24 h | NA (>99/1) | 92% |
| Ph-OCOOMe | PhNH$_2$ | L2 (1%) | DABCO (10%) rt, 6 h | 80% (>99/1) | 95% |
| Ph-OCOOMe | H$_2$N-C$_6$H$_4$-CH$_3$ | L2 (1%) | DABCO (5%) rt, 12 h | 76% (>99/1) | 94% |
| Ph-OCOOMe | H$_2$N-C$_6$H$_4$-OMe | L2 (1%) | DABCO (5%) rt, 16 h | 91% (98/2) | 95% |
| Ph-OCOOMe | H$_2$N-C$_6$H$_4$-Cl | L2 (1%) | DABCO (5%) rt, 12 h | 95% (98/2) | 96% |
| Ph-OCOOMe | H$_2$N-C$_6$H$_4$-F | L2 (1%) | DABCO (5%) rt, 12 h | 92% (97/3) | 94% |

TABLE 3a-continued

Allylic Amination of Methyl Allylic Carbonates with Anilines.

R⌒⌒OCOOMe + ArNH₂ →[[Ir(COD)Cl]₂/L (Ir/L = 1/1)][DABCO, THF, rt or 50° C.] R-CH(NHAr)-CH=CH₂ + R⌒⌒NHAr

L₁ = BINOL-derived phosphoramidite with N(CHMePh)₂ (Ra, Rb, Rc)

L₂ = BINOL-derived phosphoramidite with N(CHMeNp)₂ (Ra, Rb, Rc)

| Carbonates | Anilines | Ligand | Conditions | Yield (B/L) | Ee |
|---|---|---|---|---|---|
| Ph⌒⌒OCOOMe | 4-I-C₆H₄-NH₂ | L2 (1%) | DABCO (5%) rt, 12 h | 92% (98/2) | 96% |
| Ph⌒⌒OCOOMe | 4-CF₃-C₆H₄-NH₂ | L2 (2%) | DABCO (10%) rt, 16 h | 74% (94/6) | 96% |
| Ph⌒⌒OCOOMe | 2-Br-C₆H₄-NH₂ | L2 (1%) | DABCO (5%) rt, 16 h | 66% (93/7) | 94% |
| Ph⌒⌒OCOOMe | 3-OMe-C₆H₄-NH₂ | L2 (1%) | DABCO (5%) rt, 8 h | 82% (97/3) | 96% |
| Ph⌒⌒OCOOMe | 2-naphthylamine | L2 (1%) | DABCO (5%) rt, 16 h | 89% (99/1) | ND |
| Ph⌒⌒OCOOMe | 1-naphthylamine | L2 (1%) | DABCO (5%) rt, 10 h | 83% (97/3) | 95% |

TABLE 3b

Allylic Amination of Methyl Allylic Carbonates with Anilines.

R−CH=CH−CH₂−OCOOMe + ArNH₂ → [Ir(COD)Cl]₂/L (Ir/L = 1/1), DABCO, THF, rt or 50° C. → R−CH(NHAr)−CH=CH₂ + R−CH=CH−CH₂−NHAr

L₁ = binaphthyl phosphoramidite with N(CHMePh)₂ (Ra, Rb, Rc)

L₂ = binaphthyl phosphoramidite with N(CHMeNp)₂ (Ra, Rb, Rc)

| Carbonates | Anilines | Ligand | Conditions | Yield (regiosel.) | Ee |
|---|---|---|---|---|---|
| Ph−CH=CH−CH₂−OCOOMe | indoline | L2 (1%) | DABCO (5%) rt, 2 h | 82% (99/1) | ND |
| Ph−CH=CH−CH₂−OCOOMe | 1,2,3,4-tetrahydroquinoline | L2 (1%) | DABCO (5%) rt, 4 h | 89% (97/3) | ND |
| Ph−CH=CH−CH₂−OCOOMe | 2,4,6-trimethylaniline | L2 (1%) | DABCO (5%) rt, 2 h | 85% (97/3) | 96% |
| Me−CH=CH−CH₂−OCOOMe | PhNH₂ | L2 (1%) | DABCO (5%) rt, 6 h | 72% (97/3) | 95% |
| n-Pr−CH=CH−CH₂−OCOOMe | PhNH₂ | L2 (1%) | DABCO (5%) rt, 2 h | 87% (98/2) | 95% |
| i-Pr−CH=CH−CH₂−OCOOMe | PhNH₂ | L2 (1%) | DABCO (3%) rt, 16 h | 83% (97/3) | 97% |
| Me−CH=CH−CH=CH−CH₂−OCOOMe (attack here) | PhNH₂ | L2 (1%) | DABCO (5%) rt, 2 h | 87% (98/1/1) | 97% |
| 2-furyl−CH=CH−CH₂−OCOOMe | PhNH₂ | L2 (1%) | DABCO (5%) rt, 12 h | 81% (95/5) | 95% |
| (2-OMe-C₆H₄)−CH=CH−CH₂−OCOOMe | PhNH₂ | L2 (1%) | DABCO (5%) rt, 6 h | 91% (99/1) | 74% |
| n-Pr−CH=CH−CH₂−OCOOMe | 4-MeO-C₆H₄-NH₂ | L2 (0.1%) | DABCO (5%) 50° C., 12 h | 85% (97/3) | 94% |

Typical Prep.: In a drybox, DABCO was placed into a vial, followed by Ir and ligand. THF (0.5 mL/1 mmol) was added. Tal the vial was sealed and brought outside the box. Allylic carbonate (1 eq) and aniline (1.2-1.3 equiv) was added by syringe. The reaction was stirred at rt and monitored by TLC. When finished, teh solvent was simply removed by evaporation, and the crude product is was purified by flash chromatography.

In addition to anilines, the reaction can be conducted with other weak nitrogen nucleophiles, or with ammonia. These reactions are summarized in Table 4. For example, reactions with ammonia equivalents such as $Boc_2NLi$ and $NaN(CHO)_2$ occurred in high yield, regio and enantioselectivity. Ammonia reacts to give the bis-allylic amine product with high regio, enantio, and diastereoselectivity.

TABLE 4

Ammonia, Ammonia Equivalents, Diastereoselective Reactions

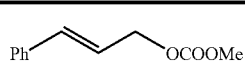

| Carbonate | Nucleophile | Ligand | Conditions | Yield (B/L) | Ee |
|---|---|---|---|---|---|
| 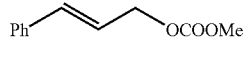 | $NH_3$/EtOH (2 eq) | L1 (4%) | rt, 16 h, THF/EtOH = 1 mL/1 mL for 1 mmol | 78% (>99/1) | 92% (>98% de) |
|  | $LiN(Boc)_2$ (1.0 eq) | L4 (1%) | rt, 16 h, THF (1 mL/mmol) | 72% (96/4) | 97% |
|  | $NaN(CHO)_2$ (1.2 eq) | L4 (1%) | 50° C., 10 h THF (1 mL/mmol) | 76% | ND |
|  | $NaN(CHO)_2$ (1.2 eq) | L4 (1%) | 50° C., 12 h THF (1 mL/mmol) | 78% | ND |
| 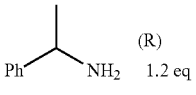 | 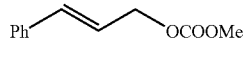 (R) 1.2 eq | L4 (1%) | rt, 16 h THF, (1 mL/mmol) | ND | 94% de |
| 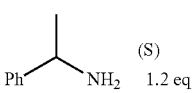 | 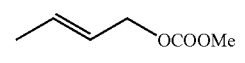 (S) 1.2 eq | L4 (1%) | rt, 16 h THF, (1 mL/mmol) | ND | 93% de |
| 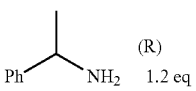 | 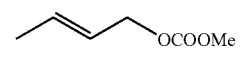 (R) 1.2 eq | L4 (1%) | rt, 16 h THF, (1 mL/mmol) | ND | >90% de |
| 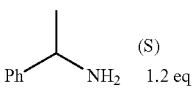 | (S) 1.2 eq | L4 (1%) | rt, 16 h THF, (1 mL/mmol) | ND | >90% de |

As shown in Table 4, reactions of α-chiral amines occur with diastereoselectivity that is controlled by the catalyst. For example, reaction of R and S phenethylamine with methyl cinnamy carbonate gives the opposite diastereomer with enantiomeric catalysts, and the diastereoselectivity appears to be independent of the chirality of the amine. Thus, it is possible to control the stereoselectivity in the production of α,α'-chiral amines and ethers. These materials are particularly useful as precursors for ring-closing metathesis processes to form saturated furans and pyrans and both pyrrolidines and piperidines with control of α-stereochemistry at the two carbons located α to the heteroatom.

Table 5 shows the activity and selectivity of various pendant groups on the ligands.

TABLE 5

Activity And Selectivity Of Various Pendant Groups On Ligands

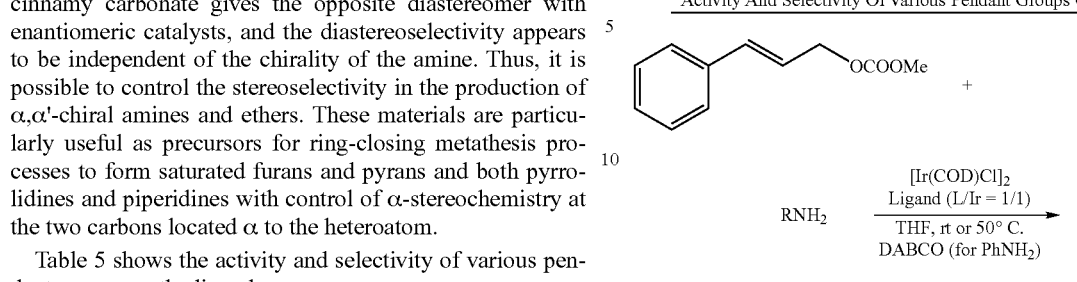

| Ligand | RNH₂ | Conditions | Conv. (ee) |
|---|---|---|---|
| L1 (R₁ = R₃ = Ph R₂ = R₄ = Me) | BnNH₂ | L1 (2 mol %) rt, 10 h | 100% (95%) |
| L1 | PhNH₂ | L1 (2 mol %) DABCO (50 mol %) rt, 24 h | 100% (92%) |
| L2 (R₁ = R₃ = 1-Napthyl R₂ = R₄ = Me) | BnNH₂ | L2 (1 mol %) rt, 4 h | 100% (95%) |
| L2 | PhNH₂ | L2 (1 mol %) DABCO (10 mol %) rt, 6 h | 100% (95%) |
| L3 (R1 = R3 = R4 = Ph R2 = Me) | BnNH₂ | L3 (2 mol %) rt, 24 h | 70% (85%) |
| L3 | PhNH₂ | L3 (2 mol %) DABCO (50 mol %) rt, 24 h | 50% (90%) |
| L4 (R1 = R3 = Ph R2 = Me, R4 = H) | BnNH₂ | L4 (2 mol %) 50° C., 48 h | 100% (91%) |
| L4 | PhNH₂ | L4 (2 mol %) DABCO (50 mol %) 50° C., 4 h | 50% (93%) |
| L5 (R1 = Np, R3 = Ph R2 = Me, R4 = H) | BnNH₂ | L5 (2 mol %) rt, 48 h | 100% (91%) |
| L5 | PhNH₂ | L5 (2 mol %) DABCO (50 mol %) rt, 4 h | 100% (93%) |

The data in Table 5 show that phosphoramidites, such as L4 and L5 that contain only one carbon-bound substituent with a stereochemical element, generate catalysts with activities and selectivities similar to those with two stereochemical elements on the amino group.

Etherification Reaction

In one embodiment, the present invention is directed to a general method of preparing allylic ethers enantioselectively. This general method comprising the steps of reacting (a) an achiral or racemic allylic ester, allylic carbonate or allylic halide and (b) a reagent containing a O—H bond or a salt thereof, and (c) a base. The reacting step takes place in a solvent and in the presence of a catalyst composition. The catalyst composition may be any catalyst composition that contains a transition metal selected from the group consisting of iridium, rhodium, ruthenium, molybdenum, and tungsten.

Like the amination reaction, the catalyst for the above general etherification reaction preferably comprises (1) a catalyst precursor having the general structure MSX$_n$, wherein M is the above transition metal; S is a coordinating ligand; X is a counterion; and n is an integer from 0 to 5; and (2) a phosphoramidite ligand having the structure

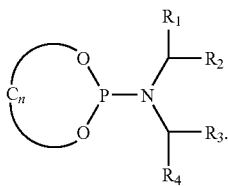

In the above structure, O—$C_n$—O is an aliphatic or aromatic diolate and $R_1$, $R_2$, $R_3$, and $R_4$ are selected from the group consisting of substituted or unsubstituted aryl groups, substituted or unsubstituted heteroaryl groups, substituted or unsubstituted aliphatic groups, and combinations thereof. However, at least one of $R_1$, $R_2$, $R_3$, or $R_4$ must be a substituted or unsubstituted aryl or heteroaryl group.

In a preferred embodiment, the present invention is further directed to methods of preparing allylic ethers enantioselectively, wherein the method comprises reacting an achiral or racemic allylic ester, allylic carbonate or allylic halide and a reagent containing an O—H bond, wherein the reacting step takes place in the presence of the above catalyst composition. The reaction can also be conducted in the presence of an optional additional additives such as metal salts (e.g., copper or zinc salts), metal halides (e.g., copper chloride or zinc chloride), bases such as 1,4-diazabicyclo(2.2.2)octane (DABCO), diazobicycloundecane, as well as various combinations of these to generate the active catalyst or promote desirable reactivity of the reactant having an OH bond, or the salt thereof. Applicants have unexpectedly discovered that under the appropriate conditions, iridium complexes of phosphoramidite ligand L1 above catalyzes allylic etherification of linear achiral electrophiles to form the branched product with high enantioselectivity (Scheme 2).

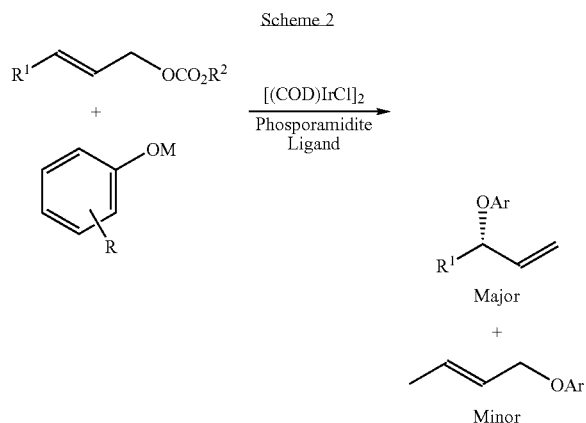

In one embodiment, the achiral allylic ester is preferably an achiral allylic ester or an achiral allylic carbonate. Examples of preferable achiral or racemic allylic acetates include, but are not limited to Ph-CH=CH—$CH_2$—OAc, 4-MeO—$C_6H_4$—CH=CH—$CH_2$—OAc, 4-$NO_2$—$C_6H_4$—CH=CH—$CH_2$—OAc, 2-MeO—$C_6H_4$—CH=CH—$CH_2$—OAc, 2-furyl-CH=CH—$CH_2$—OAc, n-$C_3H_7$—CH=CH—$CH_2$—OAc; Me-CH=CH—$CH_2$—OAc, n-Pr—CH=CH—$CH_2$—OAc, i-Pr—CH=CH—$CH_2$—OAc, $CH_3$—CH=CH—CH=CH—$CH_2$—OAc, and the like. Combinations of the above achiral allylic acetates may also be employed in the etherification reaction.

Examples of preferable achiral or racemic allylic carbonates that may be implemented in the method of the invention include Ph-CH=CH—$CH_2$—$OCOOR_2$, 4-MeO—$C_6H_4$—CH=CH—$CH_2$—$OCOOR_2$, 4-$NO_2$—$C_6H_4$—CH=CH—$CH_2$—$OCOOR_2$, 2-MeO—$C_6H_4$—CH=CH—$CH_2$—$OCOOR_2$, 2-furyl-CH=CH—$CH_2$—$OCOOR_2$, n-$C_3H_7$—CH=CH—$CH_2$—$OCOOR_2$, Me-CH=CH—$CH_2$—$OCOOR_2$, n-Pr—CH=CH—$CH_2$—$OCOOR_2$, i-Pr—CH=CH—$CH_2$—$OCOOR_2$, $CH_3$—CH=CH—CH=CH—$CH_2$—$OCOOR_2$, and the like. In each formula above, $R_2$ is a methyl or ethyl group. However, notwithstanding the above examples, it will be appreciated by those skilled in the art that other esters and carbonates can be used in the present invention, besides acetate and methyl carbonates shown above. For example, ethyl, t-butyl, phenyl, or another suitable aliphatic or aromatic group could replace methyl. As will further be appreciated, combinations of achiral allylic carbonates may also be implemented.

Useful achiral or racemic allylic halides that may be implemented in the method of the invention include Ph-CH=CH—$CH_2$—X, 4-MeO—$C_6H_4$—CH=CH—$CH_2$—X, 4-$NO_2$—$C_6H_4$—CH=CH—$CH_2$—X, 2-MeO—$C_6H_4$—CH=CH—$CH_2$—X, 2-furyl-CH=CH—$CH_2$—X, n-$C_3H_7$—CH=CH—$CH_2$—X, Me-CH=CH—$CH_2$—X, n-Pr—CH=CH—$CH_2$—X, i-Pr—CH=CH—$CH_2$—X, and $CH_3$—CH=CH—CH=CH—$CH_2$—X, wherein X is selected from a halide atom such as F, Cl, Br, and I.

Useful reagents that contain an O—H bond include alkoxides, phenoxides, siloxides, carboxylates, phosphates, alcohols, phenols, silanols, carboxylic acids, phosphorus-containing acids, and salts thereof. Specific examples of useful reagents containing an O—H bond that may be employed in the etherification method of the invention include 2-Me$C_6H_4$OLi, 4-Me$C_6H_4$OLi, 4-MeO$C_6H_4$OLi, 3-MeO$C_6H_4$OLi, 3-Ph$C_6H_4$OLi, 2-Ph$C_6H_4$OLi, 3-Me$_2$N$C_6H_4$OLi, 3,4-(OCH$_2$O)$C_6H_3$OLi, 2,4-Me$_2C_6H_3$OLi, 2,4,6-Me$_3C_6H_3$OLi, 4-Br$C_6H_4$ONa, 4-Cl$C_6H_4$ONa, 4-Br,3-Me$C_6H_4$ONa, 4-CF$_3C_6H_4$ONa, PhOLi, PhONa, as well as salts of these.

The etherificiation reaction may be carried out in the presence of an optional base. Examples of useful bases in the etherification method of the invention include 1,4-diazabicyclo(2.2.2)octane (DABCO), triethylamine, isopropyldiethylamine, ethyl dimethylamine, metal hydrides, amides, alkoxides, carbonates, and phosphates. Examples of useful solvents include DMF, ethanol, methanol, THF, acetonitrile, $CH_3NO_2$, DME, $CH_2Cl_2$, triethylamine, 1,4-dioxane, diethyl ether, toluene, hexane, and combinations thereof, as well as aqueous mixtures thereof.

Like the amination reaction above, the general reaction conditions for the etherification method of the present invention include reaction temperatures ranging from 20 to 60° C., and reaction times ranging from 1 to 96 hours. Generally, the ratio of the amounts of phosphoramidite ligand to catalyst precursor is approximately 2:1, and the enantiomeric excess (ee) of said method is typically greater than approximately 70%.

Choice of base and solvent and matching of the phenoxide nucleophile with the appropriate allylic carbonate derivative were crucial to observe high yields, regioselectivities, and enantioselectvities for formation of the major product.

Examples of the reaction and conditions are shown in Table 6.

TABLE 6

Effect of Nucleophile on the Ir-Catalyzed Enantioselective Allylic Etherification of (E)-cinnamylcarbonates (R1 = Ph)

Ph∼∼OCO$_2$R  +  PhOH or MOPh  +  base  →[(COD)IrCl]$_2$, (OR)$_2$PNR$_2$→  Ph–CH(OR$^1$)–CH=CH$_2$

1

| Entry | R | 1 | M—OPh | Temp (° C.) | time (h) | Major/Minor | Yield (%) | % (ee) |
|---|---|---|---|---|---|---|---|---|
| 1 | Me | 1a | PhOH/Et$_3$N | 50 | 15 | 93/7 | 76 | 84 |
| 2 | Me | 1a | PhOH/i-Pr$_2$NEt | 50 | 45 | 89/11 | 66 | 78 |
| 3 | Me | 1a | PhOH/Me$_2$NEt | 50 | 11 | 53/47 | 31 | 45 |
| 4 | Me | 1a | NaOPh | 23 | 22 | 97/3 | 40 | 92 |
| 5 | Et | 1b | NaOPh | 23 | 35 | 99/1 | 76 | 94 |
| 6 | Et | 1b | NaOPh | 50 | 17 | 95/5 | 78 | 92 |
| 7 | Me | 1a | LiOPh | 50 | 20 | 96/4 | 86 g | 96 |
| 8 | Me | 1a | LiOPh/CuCl | 50 | 12 | 96/4 | 73 | 37 |

In Table 6, all reactions were carried out with 1 mmol of 1 and 2.0 mmol of HOPh and base or MOPh in THF (0.5 mL) in the presence of 0.01 mmol of [(COD)IrCl]$_2$ and 0.02 mmol of phosphoramidite ligand L1 shown above, (L/Ir=1) unless otherwise noted. Ratios of major/minor regioisomer products were determined by $^1$H NMR of crude reaction mixtures. Yields represent isolated yields of the combined regioisomers. Enantiomeric excess was determined by chiral HPLC. Reactions with NaOPh were conducted in 1 mL of THF. Reactions with LiOPh/CuCl were conducted in 2 mL of THF.

The base used to generate the phenoxide influenced selectivities. To avoid transesterification, tertiary amines are used as bases for the reactions of (E)-cinnamyl methyl carbonate (1a) (Table 6, entries 1-3). The highest regio- and enantioselectivities were obtained with Et$_3$N as base at 50° C. (Table 6, entry 1). Reactions conducted with a more hindered amine (entry 2) occurred more slowly and less enantioselectively. Reactions conducted with a less hindered amine (entry 3) occurred faster, but with lower yields, regioselectivities, and enantioselectivities.

Alkali metal phenoxides as nucleophiles proved to be superior to the combination of phenol and amine base. Sodium phenoxide furnished the corresponding allylation product with high regio- and enantioselectivity (Table 6, entries 4-6). Reaction of sodium phenoxide with methyl carbonate 1a formed the alkylation product at room temperature in a modest 40% yield because of competing trans-esterification (entry 4), but reactions with the more hindered and less reactive (E)-cinnamyl ethyl carbonate (1b of Table 6) occurred without significant competing transesterification. This combination of phenoxide and carbonate gave the branched ether in good yields with excellent regio- and enantioselectivities after 35 h at room temperature or 17 h at 50° C. (Table 6, entries 5 and 6).

However, the highest yield and enantioselectivity from reaction of an electron-neutral phenol derivative with carbonate 1a occurred with the less basic lithium phenoxide. Reactions of this substrate combination occurred smoothly at 50° C. to provide after 20 h 86% yield of the major product with 96:4 regioselectivity and 96% enantioselectivity (Table 6, entry 7). Reaction of the allylic carbonate with a phenoxide generated by transmetalation of the LiOPh with CuCl occurred with much lower enantioselectivities. Other (E)-cinnamyl alcohol derivatives reacted in lower yields or with lower enantioselectivities. Reactions of LiOPh with the corresponding tert-butyl carbonate were slow, but gave the branched ether in 97% ee. (E)-Cinnamyl acetate did not react, even at 50° C. (E)-Cinnamyl diethyl phosphate underwent complete reaction with LiOPh after only 10 h at 50° C. to form the allylic ethers in a 91:9 ratio and in an 83% combined yield. However, the ee was only 60%.

Similar to the Ir-catalyzed allylic amination, regioselective formation of the major product required careful selection of the reaction conditions. In THF, the iridium phosphoramidite complex catalyzed allylic transposition of branched major product to form linear minor product. Thus, long reaction times led to lower selectivities. For example, the reaction of LiOPh (2 equiv) with 1a in THF gave complete conversion and excellent regio- and enantioselectivity after 20 h at 50° C., but lower ratios of major and minor products and lower ee's were observed at times significantly longer than 20 h. Solvent also influenced the reactivity, regioselectivity, and enantioselectivity. Reactions of 2.0 equiv of LiOPh with 1a at 50° C. in various solvents followed the order DME>THF>1,4-dioxane>Et$_2$O. Reactions in each solvent, except DME, occurred with high regioselectivities and ee's from 92 to 96%. Reactions in THF displayed the most suitable balance of rate, regio-, and enantioselectivity. Reactions were also conducted with lithium phenoxide generated in situ. LiOPh generated from n-BuLi (hexanes) or Cy$_2$NLi provided the major product with equally high yields and enantioselectivities. However, LiOPh generated from LDA reacted with lower regioselectivities, and LiOPh generated from LiN(SiMe$_3$)$_2$ did not completely convert the allylic carbonate after 72 h.

The scope of the allylic etherification catalyzed by [(COD)IrCl]$_2$ and phosphoramidite ligand L1 shown above is summarized in Table 7.

TABLE 7

Enantioselective allylic Etherification with Aryloxides Catalyzed by Phosphoramidite Ligands L1 and L4.

$$R^1\diagup\hspace{-2pt}\diagdown OCO_2R^2 \;+\; MOAr \;\xrightarrow[\text{L1 or L4}]{[(COD)IrCl]_2}\; R^1\text{-CH(OR}^1)\text{-CH=CH}_2$$

| Entry | $R^1$, $R^2$ (1) | Metal-Aryloxide (2) | Ligand | Time (h) | 4/5 b | Yield (%) | ee (%) |
|---|---|---|---|---|---|---|---|
| 1 | Ph, Me (1a) | 2-MeC$_6$H$_4$OLi (2c) | L1 | 14 | 96/4 | 87 | 95 (R) |
| 2 | Ph, Me (1a) | 4-MeC$_6$H$_4$OLi (2d) | L1 | 22 | 98/2 | 91 | 95 |
| 3 | Ph, Me (1a) | 4-MeOC$_6$H$_4$OLi (2e) | L1 | 8 | 98/2 | 88 | 97 |
| 4 | Ph, Me (1a) | 3-MeOC$_6$H$_4$OLi (2f) | L1 | 17 | 95/5 | 84e | 96 |
| 5 | Ph, Me (1a) | 3-PhC$_6$H$_4$OLi (2g) | L1 | 13 | 96/4 | 76 | 95 |
| 6 | Ph, Me (1a) | 2-PhC$_6$H$_4$OLi (2h) | L1 | 10 | 96/4 | 65 | 93 |
| 7 | Ph, Me (1a) | 3-Me$_2$NC$_6$H$_4$OLi (2i) | L1 | 14 | 99/1 | 56 | 97 |
| 8 | Ph, Me (1a) | 3,4-(OCH$_2$O)C$_6$H$_3$OLi (2j) | L1 | 18 | 99/1 | 65 | 94 |
| 9 | Ph, Me (1a) | 2,4-Me$_2$C$_6$H$_3$OLi (2k) | L1 | 11 | 98/2 | 85e | 95 |
| 10 | Ph, Me (1a) | 2,4,6-Me$_3$C$_6$H$_2$OLi (2l) | L1 | 22 | 93/7 | 82e | 93 |
| 11 | Ph, Et (1b) | 4-BrC$_6$H$_4$ONa (2m) | L1 | 8 | 96/4 | 91 | 90 |
| 12 | Ph, Et (1b) | 4-ClC$_6$H$_4$ONa (2n) | LI | 20 | 93/7 | 86 | 92 |
| 13 | Ph, Et (1b) | 4-Br,3-MeC$_6$H$_3$ONa (2o) | L1 | 8 | 95/5 | 89 | 87 |
| 14 | Ph, Et (1b) | 4-CF$_3$C$_6$H$_4$ONa (2p) | L1 | 10 | 90/10 | 92 | 80 (R) |
| 15 | 2-MeOC$_6$H$_4$, Me (1c) | PhOLi (2a) | L1 | 41 | 98/2 | 79 | 75 |
| 16 | 4-MeOC$_6$H$_4$, Me (1d) | PhOLi (2ag) | L1 | 13 | 97/3 | 70 | 86 |
| 17 | n-Pr, Me (1e) | PhOLi (2a) | L1 | 14 | 92/8 | 93 | 92 |
| 18 | n-Pr, Me (1e) | 2-MeC$_6$H$_4$OLi (2c) | L1 | 20 | 87/13 | 86 | 90 |
| 19 | n-Pr, Me (1e) | 4-MeOC$_6$H$_4$OLi (2e) | L1 | 14 | 90/10 | 73 | 85 |
| 20 | Ph, t-Bu | LiOEt/CuI | L4 | 12 | 92/8 | 85% | 95% |
| 21 | Ph, t-Bu | LiOCH(CHMe)$_2$/CuI | L4 | 16 | 99/1 | 86% | 96% |
| 22 | Ph, t-Bu | LiOCyclohexyl/CuI | L4 | 16 | 95/5 | 75% | 94% |
| 23 | Ph, t-Bu | LiO-t-Bu/CuI | L4 | 24 | 96/4 | 80% | 66% |
| 24 | Ph, t-Bu | LiOCEtMe$_2$/CuI | L4 | 24 | 97/3 | 81% | 68% |

In Table 7, all reactions were carried out with 1 mmol of allylic ester and 2.0 mmol of M-OAr (isolated from the reaction of aryl alcohols and n-BuLi or NaH) in the presence of 0.01-0.02 mmol of [(COD)IrCl]$_2$ and 0.02-0.04 mmol of phosphoramidite ligand L1 or L4 above unless otherwise noted. Ratios of regioisomers were determined by $^1$H NMR spectroscopy of crude reaction mixtures. Yields were calculated from isolated yields of major and minor products unless otherwise noted. In entries 11-14, the reaction was conducted with 1 M of 1b. In entry 16, three equivalents of LiOPh were used.

Reactions of 1a with lithium aryloxides containing a single substituent at the ortho, meta, or para position (Table 7, entries 1-7) gave the corresponding branched allylic ether (major product) with high selectivity over the achiral linear ether (minor product) and with enantioselectivities ranging from 93 to 97%. Methyl, phenyl, methoxy, or dialkylamino substituents were tolerated on the aryloxide. Lithium sesamolate (2j), lithium 2,4-dimethyl-phenoxide (2k), and the more sterically hindered 2,4,6-trimethyl-phenoxide (2l) (entries 8-10) also reacted to give the chiral phenyl ethers in good yields and with enantioselectivities between 93 and 95%.

High yields from reactions of aryloxides with electron-withdrawing groups were obtained from reactions of the sodium aryloxides and ethyl carbonate 1b (Table 7, entries 11-14). Enantioselectivities ranged from 80 to 92%. Aryloxides containing stronger electron-withdraw-ing groups, such as nitro and cyano, in the para position failed to react under these conditions. The scope of the carbonate encompassed both aromatic and aliphatic derivatives. Ortho- and para-substituted methoxycinnamyl carbonates (1c and 1d) reacted in high yield, with high regio-selectivities, and with enantioselectivities between 75 and 86% (entries 15 and 16). The combination of [(COD)IrCl]$_2$ and phosphoramidite ligand 1 above also catalyzed etherification of the straight-chain aliphatic (E)-2-hexenyl carbonate (1e) to give predominantly the branched ether (entries 17-19). Carbonate 1e reacted with unsubstituted, ortho-substituted, or electron-rich phenols to give the branched ether with 85-92% ee. Reactions of branched allylic carbonates have occurred, thus far, with low enantioselectivities after full conversion. Reactions with aliphatic alkoxides also occurred in high yields and in good to excellent enantioselectivity in the presence of copper iodide as additive. For example, reactions of the primary alkoxide and two secondary alkoxides in entries 20-22 occurred in high yields with high enantioselectivities.

Activated Catalyst

As described above, the present invention also encompasses an activated catalyst, comprising a cyclometallated phosphoramidite having the structure

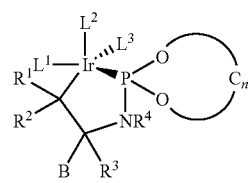

In the above cyclometallated phosphoramidite structure, O—$C_n$—O is an aliphatic or aromatic diolate as described above for the catalyst composition. B is any substituted or unsubstituted aryl or heteroaryl group. $R_1$, $R^2$, $R^3$, and $R^4$ may be hydrogen, an alkyl or benzylic group such as methyl, benzyl, phenethyl, or diphenylmethyl, or an aromatic group, such as phenyl. $L^1$ and $L^2$ are any ligands bound to the metal through an electron pair or through electrons in a pi-system of an unsaturated moiety. Examples of useful ligands include diolefins or two monoolefins, diphosphines or two monophosphines, diamines or two monoamines, diheterocyclic units such as bipyridine, or two heterocyclic units such as pyridines. $L^3$ is an optional ligand, and may be phosphine, phosphite, phosphoramidite, amine, heterocycle, carbon monoxide, or other ligand that could dissociate from the metal under the conditions of the catalytic reaction.

As explained in more detail in the following Examples, the activated catalyst is made by combining the catalyst precursor and a phosporamadite ligand in the presence of a base under conditions that form said activated catalyst.

Subsequent studies of the catalyst have revealed that it contains an activated form which comprises a cyclometallated phosphoramidite. The activated catalyst is formed in situ within the reaction mixture. Reaction of the catalyst precursor [(COD)IrCl]$_2$ with the phosphoramidite Ligand 1 (Scheme 3) forms the standard square-planar Ir(I) complex [CODIrClL$_1$] (1 in Scheme 3).

Scheme 3

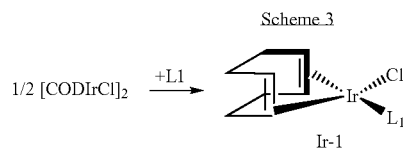

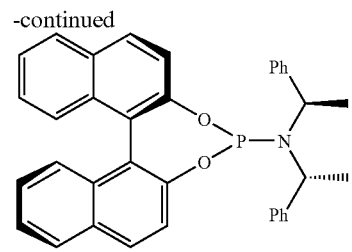

L1 ($S_a$, $S_c$, $S_c$)

Complex Ir-1 of Scheme 3 was fully characterized by NMR spectroscopy and X-ray diffraction. Treatment of Ir-1 at 50° C. with excess of methyl cinnamyl carbonate leads to no reaction. Thus, addition of the carbonate to square planar 1 does not occur during the catalytic process. However, reaction of Ir-1 at room temperature for 12 h with pyrrolidine generated a new iridium complex Ir-2, as determined by the appearance of a single set of two doublet resonances ($\delta$=152.6 and 127.8 ppm, $^3J_{P,P}$=46.3 Hz) in the $^{31}$P NMR spectrum of the reaction mixture. Reaction of complex Ir-1 with 2 equiv of the phosphoramidite ligand (Scheme 4) and pyrrolidine for 12 h generated the same compound Ir-2 in yields greater than 90%.

Scheme 4

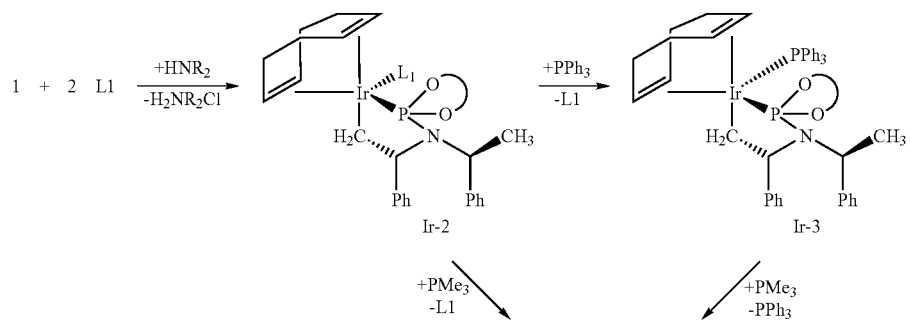

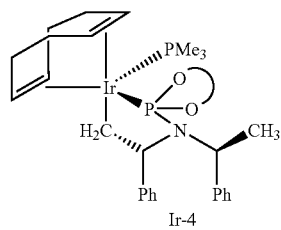

These data indicate that an unsymmetric bis-phosphoramidite complex is formed in the presence of base. Reaction of this species generated in situ with more strongly coordinating dative ligands like $PMe_3$ or $PPh_3$ displaced only one of the two phosphoramidites and generated the complexes Ir-3 and Ir-4 in Scheme 2.

Crystallographic characterization of complex Ir-4 (FIG. 1) revealed a trigonal bipyramidal metal center containing one $\eta^1$ phosphine ligand and one phosphoramidite that has undergone cyclometallation at the amino methyl group to generate a $\kappa^2$-coordination mode. The bite angle of the $\kappa^1$ phosphoramidite ligand is 80.30(12)°, and the Ir(1)-C(2) bond length is 2.141(4) Å. Only one diastereomer was observed in the crystal. A single diastereomer was also observed in solution, as indicated by a single set of doublets at 149.1 ppm and −57.3 ppm ($^3J_{P,P}$=46.5 Hz) in the $^{31}P$ NMR spectrum.

Complex Ir-4 formed from substitution of the $\eta^1$-phosphoramidite with triphenylphosphine consisted of a roughly 80:20 mixture of two diastereomers. This mixture was observed in crystalline samples by X-ray diffraction and in the solution phase by NMR spectroscopy (major isomer: δ=152.1 and 6.6 ppm (84%), $^3J_{P,P}$=20.5 Hz, minor isomer δ=148.0 and 2.3 ppm $^3J_{P,P}$=48 Hz (16%)).

These structure determinations strongly suggest that complex Ir-2, which could exist in the catalytic system and which is the precursor to Ir-3 and Ir-4, contains one cyclometallated and one $\eta^1$-phosphite ligand in a trigonal bipyramidal structure. The $^{31}P$ NMR spectrum of complex Ir-2 showed the presence of a single diastereomer; the $^1H$ and $^{13}C$ NMR spectra were complicated by conformational changes on the NMR time scale. Nevertheless, the elemental composition and lack of chloride ligand in this material were deduced by combustion analysis.

Figure 2:
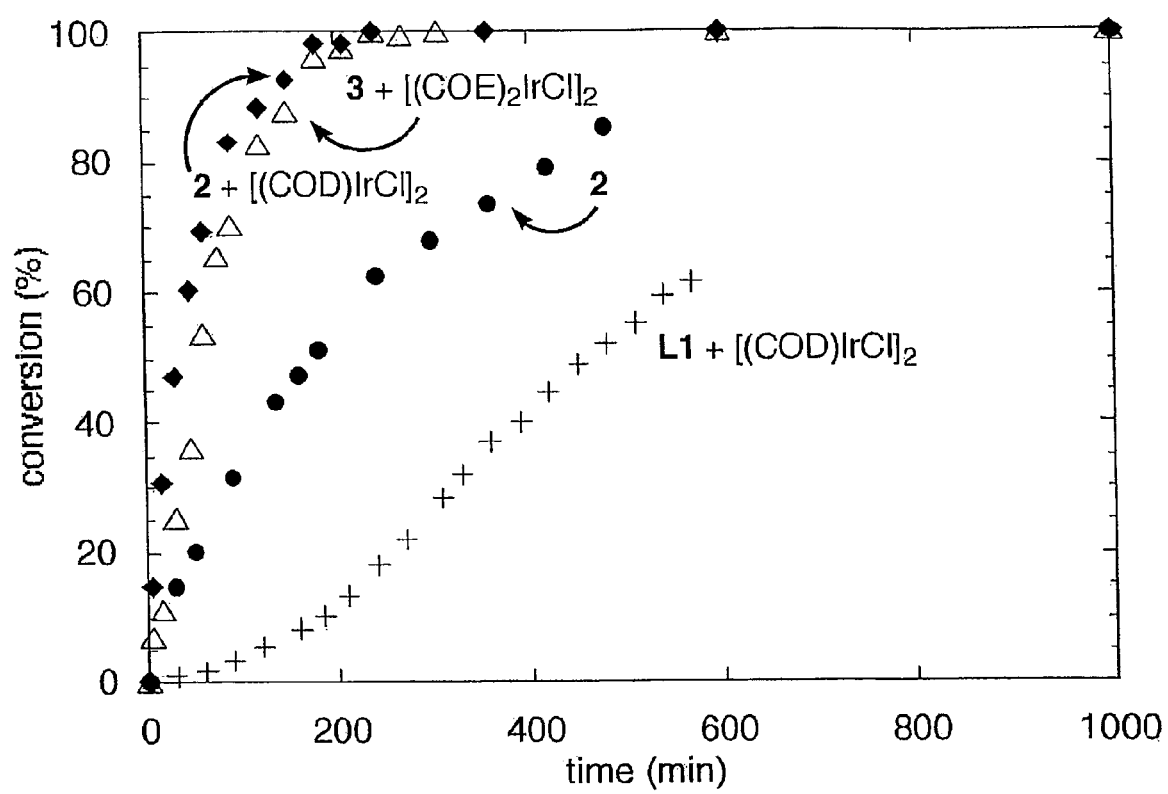
FIG. 2 depicts a comparison of the rates for reaction of methyl cinnamyl carbonate with benzylamine catalyzed by the original system, the activated catalyst and the isolated cyclometallated complexes.

It is believed that if the reaction of 1 with amine to generate Ir-2 generates the active catalyst, then reactions catalyzed by Ir-2 must occur faster than and with equally high selectivity as reactions conducted with 1 or the combination of [(COD)IrCl]$_2$ and L1. A comparison of reactions in the presence of these three catalyst compositions is shown in FIG. 2. Consistent with complex Ir-2 as an activated catalyst, the reaction of benzylamine with methyl cinnamyl carbonate occurred at much faster rates in the presence of Ir-3 than in the presence of Ir-1 or [(COD)IrCl]$_2$ and L1. The rates of reaction with Ir-3 were remarkably fast and selective. They occurred to completion in less than 2 h at room temperature to form the branched amine in 97% ee.

TABLE 8

Comparison Of The Original Catalyst 1 with the Activated Catalyst 2 in Combination with [CODIrCl]$_2$ for the Reaction of Methyl Cinnamyl Carbonate with Amines and Phenoxide Nucleophiles.

| Entry | Product | Catalyst | Time (h) | b/l | yield$^a$ | ee |
|---|---|---|---|---|---|---|
| 1 | HN(CH$_2$Ph)(CHPhCH=CH$_2$) | 1% 2 + [(COD)IrCl]$_2$ | 2 | 98/2 | 81% | 97% |
| 2 |  | 2% L1 + [(COD)IrCl]$_2$ | 12 | 98/2 | 84% | 95% |
| 3 | HN(CHPh$_2$)(CHPhCH=CH$_2$) | 1% 2 + [(COD)IrCl]$_2$ | 10 | 97/3 | 85% | 98% |
| 4 |  | 2% L1 + [(COD)IrCl]$_2$ | 10 | — | 11$^c$ | — |
| 5 | pyrrolidinyl-CHPhCH=CH$_2$ | 0.1% 2 + [(COD)IrCl]$_2$ | 10 | 99/1 | 81% | 98% |
| 6 |  | 2% L1 + [(COD)IrCl]$_2$ | 16 | 99/1 | 64% | 97% |
| 7 | NHPh-CHPhCH=CH$_2$ | 1% 2 + [(COD)IrCl]$_2$ | 2 | 99/1 | 81% | 97% |
| 8 |  | 2% L1 + [(COD)IrCl]$_2$ | 24 | — | <1% | — |
| 9$^b$ | OPh-CHPhCH=CH$_2$ | 1% 2 + [(COD)IrCl]$_2$ | 2 | 95/5 | 75% | 94% |
| 10$^b$ |  | 2% L1 + [(COD)IrCl]$_2$ | 35 | 99/1 | 76% | 94% |

$^a$Isolated yields;
$^b$Ethyl cinnamyl carbonate was used;
$^c$Conversion

Table 8 summarizes data that demonstrates increased rates, substrate scope and turnover numbers with the activated catalyst. The faster rates (FIG. 2 and entry 1 vs 2) allowed for increased scope with the less reactive of alkylamines. For example, the ammonia equivalent H$_2$NCHPh$_2$ reacted slowly with methyl cinnamyl carbonate in the presence the original catalyst, but formed the substitution product in 85% yield with 97:3 regioselectivity and 98% ee in 10 h in the presence of Ir-2 and [(COD)IrCl]$_2$.

This faster rate allowed for the allylic amination to be conducted with lower catalyst loadings. Reaction of methyl cinnamyl carbonate with pyrrolidine at room temperature for 12 h in the presence of 0.1 mol % of Ir-2 and [(COD)IrCl]$_2$ formed the branched allylic amine in 81% isolated yield, with 99:1 regioselectivity and 98% enantiomeric excess.

Weakly basic nitrogen nucleophiles did not react with the original system. This lack of reactivity can now be traced to an inability of these weak bases to generate the activated catalyst Ir-2. For example, reactions of aniline with allylic carbonates in the presence of [(COD)IrCl]$_2$ and L1 as catalyst generated no detectable product from allylic substitution. This lack of reactivity is due to the lack of reaction of Ir-1 with aniline to generate Ir-2 and not because of a lack of reactivity of aniline for allylic amination with an activated catalyst. Thus, aniline reacted with methyl cinnamyl carbonate in the presence of Ir-2 and [(COD)IrCl]$_2$ in high yield, with 99:1 selectivity for the branched isomer and in 97% ee. Likewise, sodium phenoxide reacted in the presence of isolated Ir-2 as catalyst in less than 2 h at room temperature to form the allylic ether in 75% yield with 95:5 regioselectivity and 94% ee. This reaction required 35 h to occur in the presence of [(COD)IrCl]$_2$ and L1 as catalyst.

EXAMPLES

The present invention is further described in detail by means of the following Examples. All parts and percentages are by weight, and all temperatures are degrees Celsius unless explicitly stated otherwise.

Amination Reaction

General Procedures $^1$H NMR spectra were recorded at 400.13 MHz with CDCl$_3$ as the solvent and tetramethylsilane as the internal standard. $^{13}$C{$^1$H} NMR spectra were obtained at 100.59 MHz or 125.77 MHz with CDCl$_3$ as the solvent. Chemical shifts of the $^{13}$C NMR spectra were measured relative to CDCl$_3$ (77.0 ppm). Optical rotations were measured with in a 10 cm cell (concentration c given as g/100 mL). Elemental Analyses were performed by Robertson Microlit Laboratories, Inc., Madison, N.J. 07940.

All reactions were conducted using standard Schlenk and drybox techniques. THF, Et$_2$O, and toluene were distilled from sodium-benzophenone ketyl under nitrogen. All other solvents were purchased as anhydrous grade reagents and used without further purification. [Ir(cod)Cl]$_2$ (Herde, J. L.; Lambert, J. C.; Senoff, C. V. Inorg. Synth. 1974, 15, 18), O,O'-(R)-(1,1'-Dinaphthyl-2,2'-diyl)-N,N'-di-(R,R)-1-phenylethylphosphoramidite, O,O'-(S)-(1,1'-Dinaphthyl-2,2'-diyl)-N,N'-di-(R,R)-1-phenylethylphosphoramidite, O,O'-(R)-(1,1'-Dinaphthyl-2,2'-diyl)-N,N'-diisopropylphosphoramidite, and 0,0'-(1,1'-Diphenyl-2,2'-diyl)-N,N'-di-(R,R)-1-phenylethylphosphoramidite were prepared according to published procedures (Alexakis, A.; Rosset, S.; Allamand, J.; March, S.; Guillen, F.; Benhaim, C. Synlett 2001, 1375). O,O'-(R)-(1,1'-Dinaphthyl-2,2'-diyl)-N, N'-dimethylphosphoramidite was purchased from Strem Chemicals. All allylic carbonates were synthesized by the reaction of corresponding allylic alcohols with methyl chloroformate in the presence of pyridine. (E)-4-Methoxycinnamyl alcohol, (E)-2-methoxycinnamyl alcohol, and (E)-3-(2-furanyl)-2-propen-1-ol were prepared by the DIBAH reduction of corresponding aldehydes. All amines, (E)-cinnamyl alcohol, (E)-2-hexen-1-ol, 2-methoxycinnamaldehyde, (E)-3-(2-furyl)acrolein, cinnamyl acetate (Aldrich Chemicals Co.), (E)-4-methoxycinnamaldehyde (TCI), and 4-nitrocinnamyl alcohol (Alfa Aesar) were purchased and used without further purification.

General Procedure for the Enantioselective Allylic Amination Catalyzed by Iridium-Phosphoramidite Complex:

A typical procedure is given as follows: In a drybox, [Ir(cod)Cl]$_2$ (6.5 mg, 0.010 mmol) and phosphoramidite ligand L1 (10.8 mg, 0.0200 mmol) are dissolved in 0.5 mL of THF in a screw-capped vial. A small magnetic stirbar was added, and the vial was sealed with a cap containing a PTFE septum and removed from the drybox. Benzylamine (135 mg, 1.26 mmol) and cinnamyl methycarbonate (188 mg, 0.979 mmol) are added to the reaction mixture by syringe. The reaction mixture was stirred at room temperature for 10 h and monitored by GC. After the reaction was complete, the volatile materials were evaporated. $^1$H NMR analysis of the residual crude mixture indicated the ratio of regioisomers and diallylation product to be 98/1/1. The mixture was then purified by flash column chromatography on silica gel (2.5% ethyl acetate in hexane) to give N-(1-phenyl-2-propenyl)benzylamine (184 mg, 84%). HPLC analysis indicated that the enantiomeric excess of product was 95% [Daicel CHIRALCEL OD-H (0.46 cm×25 cm); hexane/2-propanol/diethylamine=99.74/0.25/0.01; flow rate=0.6 mL/min; detection wave length=220 nm; T$_R$=15.1 (major), 17.4 (minor) min]:

N-(1-Phenyl-2-propenyl)benzylamine (Takeuchi, R.; Ue, N.; Tanabe, K.; Yamashita, K.; Shiga, N. J. Am. Chem. Soc. 2001, 123, 9525): [α]$_D^{RT}$=−7.0 (c 3.1, CHCl$_3$). $^1$H NMR (400.13 MHz, CDCl$_3$) δ 7.30-7.39 (m, 8H), 7.22-7.28 (m, 2H), 5.95 (ddd, J=16.8, 10.0, 7.2 Hz, 1H), 5.23 (dt, J=16.8, 1.6 Hz, 1H), 5.12 (dq, J=10.0, 0.8 Hz, 1H), 4.23 (d, J=7.2 Hz, 1H), 3.75 (d of AB pattern, J=13.4 Hz, 1H), 3.71 (d of AB pattern, J=13.4 Hz, 1H), 1.64 (brs, 1H). $^{13}$C NMR (100.59 MHz, CDCl$_3$) δ 142.74, 140.90, 140.38, 128.53, 128.37, 128.15, 127.31, 127.21, 126.89, 115.18, 65.09, 51.26.

N-(1-Phenyl-2-propenyl)-4-methoxybenzylamine (Yadav, J. S.; Bandyopadhyay, A.; Reddy, B. V. S. Tetrahedron Lett. 2001, 42, 6385: The general procedure was followed with 4-methoxybenzylamine (186 mg, 1.35 mmol) and cinnamyl methylcarbonate (199 mg, 1.04 mmol). The reaction was conducted at room temperature for 18 h. $^1$H NMR analysis of the crude mixture indicated the ratio of regioisomers and diallylation product to be 98/0/2. The mixture was purified by flash column chromatography on silica gel (5% ethyl acetate in hexane) to give the title compound (210 mg, 80%). HPLC analysis indicated that the enantiomeric excess of product was 94% [Daicel CHIRALCEL OD-H (0.46 cm×25 cm); hexane/2-propanol=99.75/0.25; flow rate=0.5 mL/min; detection wave length=230 nm; T$_R$=26.2 (major), 29.3 (minor) min]: [α]$_D^{RT}$=−1.8 (c 5.5, CHCl$_3$). $^1$H NMR (400.13 MHz, CDCl$_3$) δ 7.21-7.38 (m, 7H), 6.86 (d, J=8.4 Hz, 2H), 5.94 (ddd, J=17.2, 10.0, 7.6 Hz, 1H), 5.22 (dt, J=17.2, 1.4 Hz, 1H), 5.11 (ddd, J=10.0, 1.6, 1.2 Hz, 1H), 4.21 (d, J=7.6 Hz, 1H), 3.80 (s, 3H), 3.68 (d of AB pattern, J=13.0 Hz, 1H), 3.64 (d of AB pattern, J=13.0 Hz, 1H), 1.58 (brs, 1H). $^{13}$C NMR (125.77 MHz, CDCl$_3$) δ 158.54, 142.84, 141.01, 132.56, 129.29, 128.49, 127.30, 127.14, 115.05, 113.72, 64.99, 55.24, 50.65.

N-(1-Phenyl-2-propenyl)-n-hexylamine (Xu, Q.; Dittmer, D. C. Terahedron Lett. 1999, 40, 2255): The general procedure was followed with n-hexylamine (129 mg, 1.27 mmol) and cinnamyl methylcarbonate (193 mg, 1.00 mmol). The reaction was conducted at room temperature for 9 h. $^1$H NMR analysis of the crude mixture indicated the ratio of regioisomers and diallylation product to be 98/2/0. The mixture was purified by flash column chromatography on silica gel (2.5% ethyl acetate in hexane) to give the title compound (192 mg, 88%). The HPLC analysis indicated that the enantiomeric excess of product was 96% [Daicel CHIRALCEL OD-H (0.46 cm×25 cm); hexane/diethylamine=99.98/0.02; flow rate=0.4 mL/min; detection wave length=210 nm; $T_R$=19.8 (major), 20.9 (minor) min]: $[\alpha]_D^{RT}$=−19 (c 1.1, CHCl$_3$). $^1$H NMR (400.13 MHz, CDCl$_3$) δ 7.30-7.35 (m, 4H), 7.21-7.27 (m, 1H), 5.93 (ddd, J=17.2, 10.0, 6.8 Hz, 1H), 5.20 (dt, J=17.2, 1.4 Hz, 1H), 5.08 (ddd, J=10.0, 1.6, 1.2 Hz, 1H), 4.17 (d, J=6.8 Hz, 1H), 2.58 (dt, J=11.2, 7.2 Hz, 1H), 2.48 (dt, J=11.2, 7.2 Hz, 1H), 1.20-1.53 (m, 9H), 0.87 (t, J=6.8 Hz, 3H). $^{13}$C NMR (100.59 MHz, CDCl$_3$) δ 143.07, 141.23, 128.46, 127.17, 127.07, 114.77, 66.28, 47.72, 31.77, 30.14, 27.04, 22.61, 14.06.

N-(1-Phenyl-2-propenyl)allylamine: The general procedure was followed with allyl amine (75.5 mg, 1.32 mmol) and cinnamyl methylcarbonate (204 mg, 1.06 mmol). The reaction was conducted at room temperature for 12 h. The mixture was purified by flash column chromatography on silica gel (10% ethyl acetate in hexane) to give the title compound (140 mg, 76%). The HPLC analysis indicated that the enantiomeric excess of product was 97% [Daicel CHIRALCEL OD-H (0.46 cm×25 cm); hexane/diethylamine=99.99/0.01; flow rate=0.5 mL/min; detection wave length=210 nm; $T_R$=17.9 (major), 19.2 (minor) min]: $[\alpha]_D^{RT}$=−14 (c 3.1, CHCl$_3$). $^1$H NMR (400.13 MHz, CDCl$_3$) δ 7.30-7.35 (m, 4H), 7.22-7.28 (m, 1H), 5.83-5.88 (m, 2H), 5.21 (dt, J=17.2, 1.2 Hz, 1H), 5.16 (dq, J=17.2, 1.6 Hz, 1H), 5.11 (dt, J=10.0, 1.2 Hz, 1H), 5.09 (dq, J=10.0, 1.6 Hz, 1H), 4.23 (d, J=7.2 Hz, 1H), 3.21 (ddt of AB pattern, J=14.2, 6.0, 1.4 Hz, 1H), 3.16 (ddt of AB pattern, J=14.2, 6.0, 1.4 Hz, 1H), 1.41 (brs, 1H). $^{13}$C NMR (100.59 MHz, CDCl$_3$) & 142.69, 140.82, 136.72, 128.50, 127.24, 127.18, 115.90, 115.09, 65.17, 49.88. Anal. Calcd for C$_{12}$H$_{15}$N: C, 83.19; H, 8.73; N, 8.08. Found: C, 83.06; H, 8.61; N, 8.06.

1-(1-Phenyl-2-propenyl)pyrrolidine (Trost, B. M.; Spagnol, M. D. J. Chem. Soc., Perkin Trans 1 1995, 2083): The general procedure was followed with pyrrolidine (86.9 mg, 1.22 mmol) and cinnamyl methylcarbonate (185 mg, 0.96 mmol). The reaction was conducted at room temperature for 2 h. $^1$H NMR analysis of the crude mixture indicated the ratio of regioisomers to be 98/2. The mixture was purified by flash column chromatography on silica gel (5% ethyl acetate in hexane) to give the title compound (135 mg, 75%). HPLC analysis indicated that the enantiomeric excess of product was 97% [Daicel CHIRALCEL OD-H (0.46 cm×25 cm); hexane/diethylamine=99.99/0.01; flow rate=0.6 mL/min; detection wave length=210 nm; $T_R$=11.2 (major), 12.5 (minor) min]: $[\alpha]_D^{RT}$=−85 (c 3.2, CHCl$_3$). $^1$H NMR (400.13 MHz, CDCl$_3$) δ 7.28-7.37 (m, 4H), 7.20-7.25 (m, 1H), 6.04 (ddd, J=17.2, 10.0, 8.8 Hz, 1H), 5.20 (dd, J=17.2, 1.2 Hz, 1H), 5.00 (dd, J=10.0, 1.2 Hz, 1H), 3.58 (d, J=8.8 Hz, 1H), 2.45-2.54 (m, 2H), 2.33-2.42 (m, 2H), 1.76 (m, 4H). $^{13}$C NMR (100.59 MHz, CDCl$_3$) δ 142.73, 141.02, 128.48, 127.57, 127.12, 115.09, 75.20, 52.97, 23.27.

1-(1-Phenyl-2-propenyl)piperidine (Kondo, T.; Ono, H.; Satake, N.; Mitsudo, T.; Watanabe, Y. Organometallics 1995, 14, 1945): The general procedure was followed with piperidine (114 mg, 1.33 mmol) and cinnamyl methylcarbonate (194 mg, 1.01 mmol). The reaction was conducted at room temperature for 10 h. $^1$H NMR analysis of the crude mixture indicated the ratio of regioisomers to be 97/3. The mixture was purified by flash column chromatography on silica gel (2.5% ethyl acetate in hexane) to give the title compound (185 mg, 91%). HPLC analysis indicated that the enantiomeric excess of product was 96% [Daicel CHIRALCEL OJ (0.46 cm×25 cm); hexane/2-propanol/diethylamine=99.97/0.02/0.01; flow rate=0.6 mL/min; detection wave length=210 nm; $T_R$=9.3 (minor), 13.1 (major) min]: $[\alpha]_D^{RT}$=−99 (c 3.2, CHCl$_3$). $^1$H NMR (400.13 MHz, CDCl$_3$) δ 7.28-7.35 (m, 4H), 7.20-7.24 (m, 1H), 5.94 (ddd, J=17.2, 10.4, 8.5 Hz, 1H), 5.18 (dd, J=17.2, 1.6 Hz, 1H), 5.07 (dd, J=10.4, 1.6 Hz, 1H), 3.65 (d, J=8.5 Hz, 1H), 2.35-2.48 (m, 2H), 2.22-2.34 (m, 2H), 1.50-1.59 (m, 4H), 1.36-1.45 (m, 2H). $^{13}$C NMR (125.77 MHz, CDCl$_3$) δ 142.41, 140.39, 128.34, 127.95, 126.87, 115.82, 75.42, 52.46, 26.15, 24.65.

1-(1-Phenyl-2-propenyl)morpholine (Bergbreiter, D. E.; Weatherford, D. A. J. Org. Chem. 1989, 54, 2726): The general procedure was followed with morpholine (113 mg, 1.30 mmol) and cinnamyl methylcarbonate (187 mg, 0.974 mmol). The reaction was conducted at room temperature for 24 h. $^1$H NMR analysis of the crude mixture indicated the ratio of regioisomers to be 99/1. The mixture was purified by flash column chromatography on silica gel (2.5% ethyl acetate in hexane) to give the title compound (183 mg, 92%). HPLC analysis indicated that the enantiomeric excess of product was 97% [Daicel CHIRALCEL OJ (0.46 cm×25 cm); hexane/2-propanol/diethylamine=98.99/1/0.01; flow rate=0.5 mL/min; detection wave length=210 nm; $T_R$=12.4 (minor), 13.7 (major) min]: $[\alpha]_D^{RT}$=−98 (c 5.2, CHCl$_3$). $^1$H NMR (400.13 MHz, CDCl$_3$) δ 7.29-7.36 (m, 4H), 7.22-7.26 (m, 1H), 5.90 (ddd, J=17.2, 10.0, 8.8 Hz, 1H), 5.23 (dd, J=17.2, 1.6 Hz, 1H), 5.10 (dd, J=10.0, 1.6 Hz, 1H), 3.69 (t, J=4.0 Hz, 4H), 3.62 (d, J=8.8 Hz, 1H), 2.43-2.55 (m, 2H), 2.29-2.37 (m, 2H). $^{13}$C NMR (100.59 MHz, CDCl$_3$) δ 141.54, 139.70, 128.57, 127.92, 127.24, 116.64, 75.51, 67.12, 51.96.

(1-Phenyl-2-propenyl)diethylamine (Takeuchi, R.; Ue, N.; Tanabe, K.; Yamashita, K.; Shiga, N. J. Am. Chem. Soc. 2001, 123, 9525): The general procedure was followed with diethylamine (91.1 mg, 1.25 mmol) and cinnamyl methylcarbonate (193 mg, 1.01 mmol). The reaction was conducted at 50° C. for 16 h. $^1$H NMR analysis of the crude mixture indicated the ratio of regioisomer 3/4 to be 98/2. The mixture was purified by flash column chromatography on silica gel (2.5% ethyl acetate in hexane) to give the title compound (158 mg, 83%). HPLC analysis indicated that the enantiomeric excess of product was 97% [Daicel CHIRALCEL OJ (0.46 cm×25 cm); hexane/diethylamine=99.99/0.01; flow rate=0.4 mL/min; detection wave length=210 nm; $T_R$=12.6 (minor), 13.6 (major) min]: $[\alpha]_D^{RT}$=−106 (c 3.1, CHCl$_3$). $^1$H NMR (400.13 MHz, CDCl$_3$) δ 7.19-7.40 (m, 5H), 5.95 (ddd, J=17.2, 10.0, 8.8 Hz, 1H), 5.19 (dd, J=17.2, 1.6 Hz, 1H), 5.12 (dd, J=10.0, 1.6 Hz, 1H), 4.13 (d, J=8.8 Hz, 1H), 2.49-2.63 (m, 4H), 0.98 (t, J=7.2 Hz, 6H). $^{13}$C NMR (100.59 MHz, CDCl$_3$) δ 142.96, 139.50, 128.29, 127.82, 126.79, 116.06, 69.46, 42.82, 11.44.

N-[1-(4-Methoxyphenyl)-2-propenyl]benzylamine (You, S.-L.; Zhu, X.-Z.; Luo, Y.-M.; Hou, X.-L.; Dai, L.-X. J. Am. Chem. Soc. 2001, 123, 7471): The general procedure was followed with benzylamine (129 mg, 1.20 mmol) and 4-methoxycinnamyl methylcarbonate (222 mg, 1.00 mmol). The reaction was conducted at room temperature for 9 h. $^1$H NMR analysis of the crude mixture indicated the ratio of regioisomers and diallylation product to be 99/1/0. The mixture was purified by flash column chromatography on silica gel (5% ethyl acetate in hexane) to give the title compound (223 mg, 88%). HPLC analysis indicated that the enantiomeric excess of product was 96% [Daicel CHIRALCEL OD-H (0.46 cm×25 cm); hexane/2-propanol=98/2; flow rate=0.6 mL/min; detection wave length=230 nm; $T_R$=10.5 (major), 12.0 (minor) min]: $[\alpha]_D^{RT}$=−0.43 (c 5.1, CHCl$_3$). $^1$H NMR (400.13 MHz, CDCl$_3$) δ 7.21-7.33 (m, 7H), 6.88 (d, J=8.8 Hz, 2H), 5.93 (ddd, J=17.2, 10.0, 7.6 Hz, 1H), 5.20 (dt, J=17.2, 1.6 Hz, 1H), 5.10 (dt, J=10.0, 1.6 Hz, 1H), 4.18 (d, J=7.6 Hz, 1H), 3.80 (s, 3H), 3.74 (d of AB pattern, J=13.4 Hz, 1H), 3.70 (d of AB pattern, J=13.4 Hz, 1H), 1.59 (brs, 1H). $^{13}$C NMR (100.59 MHz, CDCl$_3$) δ 158.71, 141.12, 140.42, 134.84, 128.35, 128.33, 128.13, 126.85, 114.84, 113.86, 64.39, 55.24, 51.19.

N-[1-(4-Nitrophenyl)-2-propenyl]benzylamine: The general procedure was followed with [Ir(cod)Cl]$_2$ (3.3 mg, 0.0050 mmol), phosphoramidite ligand L1, (5.4 mg, 0.010 mol), THF (0.25 mL), benzylamine (111 mg, 1.03 mmol) and 4-nitrocinnamyl methylcarbonate (103 mg, 0.43 mmol). The reaction was conducted at room temperature for 12 h. $^1$H NMR analysis of the crude mixture indicated the ratio of regioisomers and diallylation product to be 83/13/4. The mixture was purified by flash column chromatography on silica gel (50% CH$_2$Cl$_2$ in hexane) to give the title compound (78.1 mg, 67%). HPLC analysis indicated that the enantiomeric excess of product was 86% [Daicel CHIRALCEL OD-H (0.46 cm×25 cm); hexane/2-propanol/diethylamine=99.4/0.5/0.1; flow rate=0.6 mL/min; detection wave length=270 nm; T$_R$=45.2 (minor), 51.1 (major) min]: [α]$_D^{RT}$=−12 (c 0.74, CHCl$_3$). $^1$H NMR (400.13 MHz, CDCl$_3$) δ 8.19 (d, J=7.2 Hz, 2H), 7.57 (d, J=7.2 Hz, 2H), 7.24-7.35 (m, 5H), 5.87 (ddd, J=17.2, 10.4, 7.2 Hz, 1H), 5.26 (d, J=17.2 Hz, 1H), 5.19 (d, J=10.4 Hz, 1H), 4.33 (d, J=7.2 Hz, 1H), 3.74 (d of AB pattern, J=13.2 Hz, 1H), 3.69 (d of AB pattern, J=13.2, 1H), 1.67 (brs, 1H). $^{13}$C NMR (125.77 MHz, CDCl$_3$) δ 150.35, 147.14, 139.77, 139.51, 128.45, 128.14, 128.06, 127.12, 123.74, 116.56, 64.58, 51.26. Anal. Calcd for C$_{16}$H$_{16}$N$_2$O$_2$: C, 71.62; H, 6.01; N, 10.44. Found: C, 71.39; H, 5.99; N, 10.31.

N-[1-(2-Methoxyphenyl)-2-propenyl]benzylamine: The general procedure was followed with benzylamine (139 mg, 1.30 mmol) and 2-methoxycinnamyl methylcarbonate (254 mg, 1.00 mmol). The reaction was conducted at room temperature for 16 h. $^1$H NMR analysis of the crude mixture indicated the ratio of regioisomers and diallylation product to be 95/4/1. The mixture was purified by flash column chromatography on silica gel (5% ethyl acetate in hexane) to give the title compound (196 mg, 77%). HPLC analysis indicated that the enantiomeric excess of product was 76% [Daicel CHIRALCEL OD-H (0.46 cm×25 cm); hexane/2-propanol/diethylamine=99.49/0.5/0.01; flow rate=0.5 mL/min; detection wave length=220 nm; T$_R$=23.3 (major), 25.1 (minor) min]: [α]$_D^{RT}$=−4.6 (c 5.2, CHCl$_3$). $^1$H NMR (400.13 MHz, CDCl$_3$) δ 7.28-7.36 (m, 5H), 7.21-7.26 (m, 2H), 6.96 (dt, J=7.6, 0.8 Hz, 1H), 6.88 (dd, J=8.4, 0.8 Hz, 1H), 6.03 (ddd, J=17.2, 10.4, 6.8 Hz, 1H), 5.21 (dt, J=17.2, 1.6 Hz, 1H), 5.11 (ddd, J=10.4, 1.6, 1.0 Hz, 1H), 4.58 (d, J=6.8 Hz, 1H), 3.81 (s, 3H), 3.74 (d of AB pattern, J=13.2, 1H), 3.69 (d of AB pattern, J=13.2 Hz, 1H), 1.83 (brs, 1H). $^{13}$C NMR (100.59 MHz, CDCl$_3$) δ 157.10, 140.63, 139.90, 130.66, 128.25, 128.22, 128.10, 128.05, 126.74, 120.78, 114.95, 110.71, 59.57, 55.32, 51.47. Anal. Calcd for C$_{17}$H$_{19}$NO: C, 80.60; H, 7.56; N, 5.53. Found: C, 80.68; H, 7.55; N, 5.72.

N-[1-(2-Furyl)-2-propenyl]benzylamine (Dondoni, A.; Merchán, F. L.; Merino, P.; Tejero, T. *Synth. Commun.* 1994, 24, 2551): The general procedure was followed with benzylamine (130 mg, 1.21 mmol) and 3-(2-furanyl)-2-propenyl methylcarbonate (182 mg, 1.00 mmol). The reaction was conducted at room temperature for 10 h. $^1$H NMR analysis of the crude mixture indicated the ratio of regioisomers and diallylation product to be 96/2/2. The mixture was purified by flash column chromatography on silica gel (2.5% ethyl acetate in hexane) to give the title compound (125 mg, 58%). HPLC analysis indicated that the enantiomeric excess of product was 97% [Daicel CHIRALCEL OD-H (0.46 cm×25 cm); hexane/2-propanol=98/2; flow rate=0.5 mL/min; detection wave length=230 nm; T$_R$=10.3 (major), 11.2 (minor) min]: $^1$H NMR (400.13 MHz, CDCl$_3$) δ 7.38 (dd, J=1.8, 0.6 Hz, 1H), 7.29-7.34 (m, 4H), 7.22-7.28 (m, 1H), 6.33 (dd, J=3.2, 1.8 Hz, 1H), 6.20 (d, J=3.2 Hz, 1H), 5.98 (ddd, J=17.2, 10.0, 7.2 Hz, 1H), 5.26 (dt, J=17.2, 1.2 Hz, 1H), 5.23 (dt, J=10.0, 1.2 Hz, 1H), 4.31 (d, J=7.2 Hz, 1H), 3.77 (s, 3H), 1.68 (brs, 1H). $^{13}$C NMR (125.77 MHz, CDCl$_3$) δ 155.31, 141.82, 140.01, 137.50, 128.39, 128.22, 126.97, 116.87, 110.08, 106.37, 58.31, 50.98.

N-[1-(n-Propyl)-2-propenyl]benzylamine (Yadav, J. S.; Bandyopadhyay, A.; Reddy, B. V. S. *Tetrahedron Lett.* 2001, 42, 6385): The general procedure was followed with benzylamine (145 mg, 1.35 mmol) and 2-hexenyl methylcarbonate (160 mg, 1.01 mmol). The reaction was conducted at room temperature for 10 h. $^1$H NMR analysis of the crude mixture indicated the ratio of regioisomers and diallylation product to be 88/8/4. The mixture was purified by flash column chromatography on silica gel (2.5% ethyl acetate in hexane) to give the title compound (127 mg, 66%). HPLC analysis indicated that the enantiomeric excess of product was 95% [Daicel CHIRALCEL OD-H (0.46 cm×25 cm); hexane/2-propanol/diethylamine=99.49/0.5/0.01; flow rate=0.6 mL/min; detection wave length=210 nm; T$_R$=8.9 (major), 11.6 (minor) min]: [α]$_D^{RT}$=+1.1 (c 5.1, CHCl$_3$). $^1$H NMR (400.13 MHz, CDCl$_3$) δ 7.22-7.32 (m, 5H), 5.62 (ddd, J=16.8, 10.4, 7.6 Hz, 1H), 5.14 (dd, J=10.4, 1.6 Hz, 1H), 5.10 (dd, J=16.8, 1.6 Hz, 1H), 3.83 (d, J=13.2 Hz, 1H), 3.64, (d, J=13.2 Hz, 1H), 3.03 (dt, J=7.6, 6.0 Hz, 1H), 1.25-1.52 (m, 5H), 0.89 (t, J=7.2 Hz, 3H). $^{13}$C NMR (125.77 MHz, CDCl$_3$) δ 141.37, 140.72, 128.34, 128.16, 126.76, 115.92, 61.00, 51.22, 37.93, 19.08, 14.06.

General Procedure for the Enantioselective Allylic Amination Catalyzed by Iridium-Phosphoramidite Complex with DABCO as Additive:

A typical procedure is given for the reaction of entry 1 in Table 1. In a drybox, DABCO (5.6 mg, 0.050 mmol), [Ir(cod)Cl]$_2$ (3.4 mg, 0.005 mmol) and (Ra,Rc,Rc)-7 (6.4 mg, 0.01 mmol) were dissolved in 0.5 mL of THF in a screw-capped vial. A small magnetic stirbar was added, and the vial were sealed with a cap containing a PTFE septum and removed from the drybox. Aniline (130 mg, mmol) and cinnamyl carbonate (188 mg, 0.979 mmol) were added to the reaction mixture by syringe. The reaction mixture was stirred at room temperature for 10 h and monitored by GC and TLC. After the reaction was complete, the volatile materials were evaporated. $^1$H NMR analysis of the residue crude mixture indicated the ratio of regioisomers to be greater than 99/1. The mixture was then purified by flash column chromatography on silica gel (1.5% ethyl acetate in hexanes) to give the desired α-Ethynyl-N-(p-tolyl)-benzenemethanamine (0.164 g, 80%). HPLC analysis indicated that the enantiomeric excess of the product was 95% [Diacel CHIRALCEL OD-H (0.46 cm×25 cm); hexanes/2-propanol=99.75/0/25; flow rate=0.6 mL/min; detection wavelength=254 nm; Tr=(major), (minor) min]. α-Ethynyl-N-phenylbenzenemethanamine. $^1$H NMR (400.13 MHz, CDCl$_3$) δ 7.44-7.24 (m, 5H), 7.20-7.10 (m, 2H), 6.69 (t, J=7.2 Hz, 1H), 6.60 (d, J=8.0 Hz, 2H), 6.04 (ddd, J=16.8, 10.4, 6.4 Hz, 1H), 5.28 (dt, J=17.2, 1.2 Hz, 1H), 5.22 (dt, J=10.0, 1.2 Hz, 1H), 4.94 (t, J=4.4 Hz, 1H), 4.04 (br s, 1H).

α-Ethynyl-N-(p-tolyl)-benzenemethanamine. The general procedure was followed with cinnamyl carbonate (0.188 g, 0.979 mmol) and p-toluidine (0.160 g, 1.5 mmol). The reaction was conducted at room temperature for 6 h. $^1$H NMR analysis of the crude reaction mixture indicated the ratio of regioisomers to be >99/1. The mixture was purified by flash column chromatography on silica gel (2% ethyl acetate in hexanes) to give the title compound (0.166 g, 76%). HPLC analysis indicated the enantiomeric excess of the product was 94% [Diacel CHIRALCEL OD-H (0.46 cm×25 cm); hexane/2-propanol=99.75/0.25; flow rate=0.6 mL/min; detection wavelength=254 ml; $T_R$=24.2 (minor), 32.2 (major) min; $[\alpha]_D^{RT}$=(c, CHCl$_3$). $^1$H NMR (400.13 MHz, CDCl$_3$) δ 7.44-7.32 (m, 4H), 7.28 (dt, J=7.2, 2.0 Hz, 1H), 7.06 (d, J=7.6 Hz, 1H), 7.03 (t, J=7.2 Hz, 1H), 6.65 (t, J=7.2 Hz, 1H), 6.52 (d, J=8.0 Hz, 1H), 6.08 (ddd, J=16.8, 10.4, 6.0 Hz, 1H), 5.27 (dt, J=17.2, 1.2 Hz, 1H), 5.23 (dt, J=10.4, 1.2 Hz, 1H), 4.99 (t, J=4.4 Hz, 1 H), 3.88 (br s, 1H), 2.20 (s, 3H).

α-Ethynyl-N-(o-bromophenyl)-benzenemethanamine.

The general procedure was followed with cinnamyl carbonate (0.188 g, 0.979 mmol) and o-bromoaniline (0.215 g, 1.25 mmol). The reaction was conducted at room temperature for 16 h. $^1$H NMR analysis of the crude reaction mixture indicated the ratio of regioisomers to be 93/7. The mixture was purified by flash column chromatography on silica gel (1.5% ethyl acetate in hexanes) to give the title compound (0.185 g, 66%). HPLC analysis indicated the enantiomeric excess of the product was 94% [Diacel CHIRALCEL OD-H (0.46 cm×25 cm); hexane/2-propanol=99.75/0.25; flow rate=0.6 mL/1 min; detection wavelength=254 nm; $T_R$=14.8 (minor), 23.9 (major) min]; $[\alpha]_D^{RT}$=(c, CHCl$_3$). $^1$H NMR (400.13 MHz, CDCl$_3$) δ 7.46-7.25 (m, 6H), 7.07 (td, J=7.6, 0.8 Hz, 1H), 6.55 (t, J=7.6 Hz, 2 H), 6.07 (ddd, J=16.8, 10.4, 6.0 Hz, 1H), 5.27 (d, J=10.0 Hz, 1H), 5.24 (t, J=1.2 Hz, 1H), 4.98 (t, J=5.6 Hz, 1H), 4.75 (d, J=5.2 Hz, 1H). $^{13}$C NMR (100.59 MHz, CDCl$_3$) δ 143.82, 141.13, 138.58, 132.26, 128.79, 128.26, 127.54, 126.94, 118.05, 116.25, 112.71, 109.91, 60.53. Anal. Calcd for C$_{15}$H$_{14}$NBr: C, 62.52; H, 4.90; N, 4.86; Br, 27.73. Found: C, 62.77; H, 4.92; N, 4.87; Br, 27.46.

α-Ethynyl-N-p-methoxyphenyl)-benzenemethanamine.

The general procedure was followed with cinnamyl carbonate (0.188 g, 0.979 mmol) and p-anisidine (0.15 g, 1.22 mmol). The reaction was conducted at room temperature for 16 h. $^1$H NMR analysis of the crude reaction mixture indicated the ratio of regioisomers to be. The mixture was purified by flash column chromatography on silica gel (4% ethyl acetate in hexanes) to give the title compound (0.214 g, 91%). HPLC analysis indicated the enantiomeric excess of the product was 95% [Diacel CHIRALCEL OD-H (0.46 cm×25 cm); hexane/2-propanol=99.75/0.25; flow rate=0.6 mL/min; detection wavelength=254 nm; $T_R$=38.9 (major), 58.4 (minor) min]; $[\alpha]_D^{RT}$=(c, CHCl$_3$). $^1$H NMR (400.13 MHz, CDCl$_3$) δ 7.44-7.24 (m, 5H), 6.73 (dt, J=8.8, 2.8 Hz, 1H), 6.56 (dt, J=8.8, 2.8 Hz, 1H), 6.03 (ddd, J=16.8, 10.0, 6.0 Hz, 1H), 5.26 (dt, J=17.2, 1.2 Hz, 1H), 5.20 (dt, J=10.0, 1.3 Hz, 1H), 4.85 (d, J=6.0 Hz, 1H), 3.79 (br s, 1H), 3.72 (s, 3H). $^{13}$C NMR (100.59 MHz, CDCl$_3$) δ. Anal. Calcd for C$_{16}$H$_{17}$NO: C, 80.30; H, 7.16; N, 5.85. Found: C, 80.05; H, 7.06; N, 5.97.

α-Ethynyl-N-(2,4,6-trimethylphenyl)-benzenemethanamine.

The general procedure was followed with cinnamyl carbonate (0.188 g, 0.979 mmol) and 2,4,6-trimethylaniline (0.170 g, 1.25 mmol). The reaction was conducted at room temperature for 12 h. $^1$H NMR analysis of the crude reaction mixture indicated the ratio of regioisomers to be 97/3. The mixture was purified by flash column chromatography on silica gel (1% ethyl acetate in hexanes) to give the title compound (0.207 g, 85%). HPLC analysis indicated the enantiomeric excess of the product was 96% [Diacel CHIRALCEL OD-H (0.46 cm×25 cm); hexane/2-propanol=99.75/0.25; flow rate=0.6 mL/min; detection wavelength=254 nm; $T_R$=17.0 (major), 19.5 (minor) min]; $[\alpha]_D^{RT}$=(c, CHCl$_3$). $^1$H NMR (400.13 MHz, CDCl$_3$) δ 7.38-7.23 (m, 5H), 6.78 (s, 2H), 6.05 (ddd, J=17.2, 10.0, 6.4 Hz, 1H), 5.17 (dt, J=10.4, 1.3 Hz, 1H), 4.61 (t, J=6.4 Hz, 1H), 3.12 (br s, 1H), 2.22 (s, 3H), 2.11 (s, 6H). $^{13}$C NMR (100.59 MHz, CDCl$_3$) δ 142.92, 141.89, 139.34, 130.89, 129.77, 129.34, 128.41, 127.10, 126.93, 115.51, 64.19, 20.56, 18.61. Anal. Calcd for C$_{18}$H$_{21}$N: C, 86.01; H, 8.42; N, 5.57. Found: C, 86.18; H, 8.49; N, 5.62.

α-Ethynyl-N-(p-trifluoromethylphenyl)-benzenemethanamine. The general procedure was followed with cinnamyl carbonate (0.094 g, 0.490 mmol) and p-trifluoromethylaniline (0.100 g, 0.62 mmol). The reaction was conducted at room temperature for 12 h. $^1$H NMR analysis of the crude reaction mixture indicated the ratio of regioisomers to be 94/6. The mixture was purified by flash column chromatography on silica gel (1% ethyl acetate in hexanes) to give the title compound (0.098 g, 72%). HPLC analysis indicated the enantiomeric excess of the product was 96% [Diacel CHIRALCEL OD-H (0.46 cm×25 cm); hexane/2-propanol=99.75/0.25; flow rate=0.6 mL/min; detection wavelength=254 nm; $T_R$=29.8 (major), 34.9 (minor) min]: $[\alpha]_D^{RT}$=(c, CHCl$_3$). $^1$H NMR (400.13 MHz, CDCl$_3$) δ 7.50-7.35 (m, 7H), 6.64 (d, J=8.4 Hz, 2H), 6.08 (ddd, J=16.8, 10.4, 6.0 Hz, 1H), 5.33 (dt, J=7.2, 1.2 Hz, 1H), 5.30 (d, J=1.2 Hz, 1H), 5.02 (t, J=5.6 Hz, 1H), 4.40 (d, J=4.8 Hz, 1H). $^{13}$C NMR (100.59 MHz, CDCl$_3$) δ 149.50, 140.88, 138.01, 128.88, 127.76, 127.08, 126.43 (q, J=3.8 Hz), 123.56, 119.03 (q, J=32.5 Hz), 116.58, 112.64, 60.34. Anal. Calcd for C$_{16}$H$_{14}$NF$_3$: C, 69.31; H, 5.09; N, 5.05; F, 20.55. Found: C, 69.46; H, 5.12; N, 5.09; F, 20.37.

α-Ethynyl-N-(p-fluorophenyl)-benzenemethanamine.

The general procedure was followed with cinnamyl carbonate (0.188 g, 0.979 mmol) and p-fluoroaniline (0.130 g, 1.17 mmol). The reaction was conducted at room temperature for 12 h. $^1$H NMR analysis of the crude reaction mixture indicated the ratio of regioisomers to be 95/5. The mixture was purified by flash column chromatography on silica gel (1.5% ethyl acetate in hexanes) to give the title compound (0.214 g, 96%). HPLC analysis indicated the enantiomeric excess of the product was 94% [Diacel CHIRALCEL OD-H (0.46 cm×25 cm); hexane/2-propanol=99.75/0.25; flow rate=0.6 mL/min; detection wavelength=254 nm; $T_R$=22.5 (major), 29.4 (minor) min]: $[\alpha]_D^{RT}$=(c, CHCl$_3$). $^1$H NMR (400.13 MHz, CDCl$_3$) δ 7.48-7.41 (m, 4H), 7.39-7.34 (m, 1H), 6.96-6.89 (m, 2H), 6.63-6.56 (m, 2H), 6.11 (ddd, J=16.8, 10.4, 6.0 Hz, 1H), 5.36 (dt, J=17.2, 1.2 Hz, 1H), 5.31 (dt, J=10.0, 1.2 Hz, 1H), 4.95 (d, J=5.6 Hz, 1H), 4.02 (br s, 1H). $^{13}$C NMR (100.59 MHz, CDCl$_3$) δ 155.76 (d. J=234 Hz), 143.44 (d, J=2.3 Hz), 141.61, 128.71, 127.45, 127.03, 116.03, 115.44 (d, J=22.1 Hz), 114.30 (d, J=8.4 Hz), 61.36. Anal. Calcd for C$_{15}$H$_{14}$NF: C, 79.27; H, 6.21; N, 6.16; F, 8.36. Found: C, 79.16; H, 6.24; N, 6.24; F, 8.46.

α-Ethynyl-N-(p-chlorophenyl)-benzenemethanamine. The general procedure was followed with cinnamyl carbonate (0.188 g, 0.979 mmol) and p-chloroaniline (0.150 g, 11.18 mmol). The reaction was conducted at room temperature for 16 h. $^1$H NMR analysis of the crude reaction mixture indicated the ratio of regioisomers to be 98/2. The mixture was purified by flash column chromatography on silica gel (2% ethyl acetate in hexanes) to give the title compound (0.225 g, 95%). HPLC analysis indicated the enantiomeric excess of the product was 96% [Diacel CHIRALCEL OD-H (0.46 cm×25 cm); hexane/2-propanol=99.75/0.25; flow rate=0.6 mL/min; detection wavelength=254 nm; $T_R$=29.6 (major), 46.3 (minor) min]: $[\alpha]_D^{RT}$=(c, CHCl$_3$). $^1$H NMR (400.13 MHz, CDCl$_3$) δ 7.48-7.36 (m, 5H), 7.17 (dt, J=8.8, 2.0 Hz, 2H), 6.59 (dt, J=8.8, 2.4 Hz, 2H), 6.10 (ddd, J=16.8, 10.4, 6.0 Hz, 1H), 5.36 (dt, J=14.8, 1.3 Hz, 1H), 5.33 (dt, J=8.0, 1.2 Hz, 1H), 4.98 (d, J=6.0 Hz, 1H), 4.14 (br s, 1H). $^{13}$C NMR (100.59 MHz, CDCl$_3$) δ 145.59, 141.25, 138.51, 128.82, 128.71, 127.52, 127.00, 122.03, 116.20, 114.56, 60.75. Anal.

Calcd for C$_{15}$H$_{14}$NCl: C, 73.92; H, 5.79; N, 5.75; Cl, 14.55. Found: C, 73.94; H, 5.83; N, 5.83; Cl, 14.67.

α-Ethynyl-N-(p-iodophenyl)-benzenemethanamine. The general procedure was followed with cinnamyl carbonate (0.188 g, 0.979 mmol) and p-iodoaniline (0.220 g, 1.04 mmol). The reaction was conducted at room temperature for 12 h. $^1$H NMR analysis of the crude reaction mixture indicated the ratio of regioisomers to be 98/2. The mixture was purified by flash column chromatography on silica gel (1.5% ethyl acetate in hexanes) to give the title compound (0.303 g, 92%). HPLC analysis indicated the enantiomeric excess of the product was 96% [Diacel CHIRALCEL OD-H (0.46 cm×25 cm); hexane/2-propanol=99/1; flow rate=0.6 mL/min; detection wavelength=254 nm; T$_R$=18.4 (major), 23.1 (minor) min]: [α]$_D^{RT}$=(c, CHCl$_3$). $^1$H NMR (400.13 MHz, CDCl$_3$) δ 7.48-7.40 (m, 6H), 7.36 (s, J=4.6 Hz, 1H), 6.43 (dt, J=8.8, 2.4 Hz, 2H), 6.09 (ddd, J=16.8, 10.4, 6.0 Hz, 1H), 5.34 (dt, J=12.0, 1.3 Hz, 1H), 5.31 (dt, J=5.2, 1.2 Hz, 1H), 4.97 (d, J=5.6 Hz, 1H), 4.15 (br s, 1H). $^{13}$C NMR (100.59 MHz, CDCl$_3$) δ 146.53, 141.10, 138.35, 137.51, 128.72, 127.53, 126.99, 116.28, 115.69, 78.32, 60.46. Anal. Calcd for C$_{15}$H$_{14}$NI: C, 53.75; H, 4.21; N, 4.18; I, 37.86. Found: C, 53.59; H, 4.27; N, 4.17; I, 38.04.

α-Ethynyl-N-(m-methoxyphenyl)-benzenemethanamine. The general procedure was followed with cinnamyl carbonate (0.188 g, 0.979 mmol) and m-anisidine (0.150 g, 1.22 mmol). The reaction was conducted at room temperature for 12 h. $^1$H NMR analysis of the crude reaction mixture indicated the ratio of regioisomers to be 97/3. The mixture was purified by flash column chromatography on silica gel (4% ethyl acetate in hexanes) to give the title compound (0.192 g, 82%). [α]$_D^{RT}$=(c, CHCl$_3$). $^1$H NMR (400.13 MHz, CDCl$_3$) δ 7.50-7.40 (m, 4H), 7.36 (tt, J=6.8, 2.0 Hz, 1H), 7.14 (t, J=8.0 Hz, 1H), 6.37 (dd, J=8.0, 2.4 Hz, 1H), 6.32 (dd, J=8.4, 2.0 Hz, 1H), 6.12 (ddd, J=16.8, 10.0, 6.0 Hz, 1H), 5.37 (dt, J=16.8, 1.4 Hz, 1H), 5.32 (dt, J=10.4, 1.4 Hz, 1H), 5.03 (br s, 1H), 4.18 (br s, 1H), 3.79 (s, 3H). $^{13}$C NMR (100.59 MHz, CDCl$_3$) δ 160.50, 148.47, 141.68, 138.84, 129.71, 128.63, 127.35, 127.02, 115.98, 106.53, 102.62, 99.46, 60.71, 54.85. Anal. Calcd for C$_{16}$H$_{17}$NO: C, 80.30; H, 7.16; N, 5.85. Found: C, 80.17; H, 7.24; N, 5.78.

α-Ethynyl-N-1-napthyl-benzenemethanamine. The general procedure was followed with cinnamyl carbonate (0.188 g, 0.979 mmol) and 1-napthylamine (0.170 g, 1.18 mmol). The reaction was conducted at room temperature for 16 h. $^1$H NMR analysis of the crude reaction mixture indicated the ratio of regioisomers to be 98/2. The mixture was purified by flash column chromatography on silica gel (1.5% ethyl acetate in hexanes) to give the title compound (0.210 g, 83%). HPLC analysis indicated the enantiomeric excess of the product was 95% [Diacel CHIRALCEL OD-H (0.46 cm×25 cm); hexane/2-propanol=99/1; flow rate=0.6 mL/min; detection wavelength=254 μm; T$_R$=29.3 (minor), 40.3 (major) min]: [α]$_D^{RT}$=(c, CHCl$_3$). $^1$H NMR (400.13 MHz, CDCl$_3$) δ 7.68 (dd, J=8.4, 1.6 Hz, 1H), 7.62 (dd, J=7.6, 2.0 Hz, 1H), 7.30-7.03 (m, 9H), 6.39 (dd, J=6.6, 1.8 Hz, 1H), 5.97 (ddd, J=17.2, 10.4, 6.0 Hz, 1H), 5.18 (dt, J=16.8, 1.2 Hz, 1H), 5.10 (dt, J=10.0, 1.2 hz, 1H), 4.95 (d, J=6.0 Hz, 1H), 4.57 (br s, 1H). $^{13}$C NMR (100.59 MHz, CDCl$_3$) δ 141.95, 141.57, 138.88, 134.17, 128.74, 128.67, 127.46, 127.08, 126.41, 125.61, 124.69, 123.37, 119.79, 117.59, 116.25, 106.20, 60.86. Anal. Calcd for C$_{19}$H$_{17}$N: C, 87.99; H, 6.61; N, 5.40. Found: C, 88.07; H, 6.53; N, 5.49.

α-Ethynyl-N-2-napthyl-benzenemethanamine. The general procedure was followed with cinnamyl carbonate (0.188 g, 0.979 mmol) and 2-napthylamine (0.170 g, 1.18 mmol). The reaction was conducted at room temperature for 16 h. $^1$H NMR analysis of the crude reaction mixture indicated the ratio of regioisomers to be 99/1. The mixture was purified by flash column chromatography on silica gel (1.5% ethyl acetate in hexanes) to give the title compound (0.225 g, 89%). [α]$_D^{RT}$=(c, CHCl$_3$). $^1$H NMR (400.13 MHz, CDCl$_3$) δ 7.53 (d, J=8.0 Hz, 1H), 7.48 (d, J=8.0 Hz, 1H), 7.42 (d, J=8.0 Hz, 1H), 7.31-7.11 (m, 6H), 7.06 (t, J=7.6 Hz, 1H), 6.76 (dd, J=9.0, 2.2 Hz, 1H), 6.64 (d, J=2.0 Hz, 1H), 5.95 (ddd, J=17.2, 10.4, 6.0 Hz, 1H), 5.20 (d, J=17.6 Hz, 1H), 5.13 (d, J=9.6 Hz, 1H), 4.94 (d, J=5.6 Hz, 1H), 4.06 (br s, 1H). $^{13}$C NMR (100.59 MHz, CDCl$_3$) δ 144.65, 141.52, 138.63, 134.90, 128.74, 128.73, 127.53, 127.48, 127.45, 127.14, 126.18, 125.99, 122.04, 118.02, 116.16, 105.82, 60.18. Anal. Calcd for C$_{19}$H$_{17}$N: C, 87.99; H, 6.61; N, 5.40. Found: C, 88.16; H, 6.58; N, 5.41.

1-(1-Phenyl-2-propenyl)-1,2,3,4-tetrahydroquinolin. The general procedure was followed with cinnamyl carbonate (0.188 g, 0.979 mmol) and 1,2,3,4-tetrahdroquinoline (0.160 g, 1.20 mmol). The reaction was conducted at room temperature for 1 h. $^1$H NMR analysis of the crude reaction mixture indicated the ratio of regioisomers to be 98/2. The mixture was purified by flash column chromatography on silica gel (1% ethyl acetate in hexanes) to give the title compound and its regioisomer as a mixture (0.212 g, 89%). HPLC analysis indicated the enantiomeric excess of the product was 96% [Diacel CHIRALCEL OD-H (0.46 cm×25 cm); hexane/2-propanol=99.9/0.1; flow rate=0.6 mL/min; detection wavelength=254 nm; T$_R$=20.7 (major), 25.2 (minor) min]: [α]$_D^{RT}$=(c, CHCl$_3$). $^1$H NMR (400.13 MHz, CDCl$_3$) δ 7.52-7.30 (m, 5H), 7.20-7.08 (m, 2H), 6.77 (dd, J=8.0, 3.6 Hz, 1H), 6.73 (t, J=3.2 Hz, 1H), 6.29 (ddd, J=17.2, 10.4, 6.0 Hz, 1H), 5.61 (d, J=4.8 Hz, 1H), 5.52 (dd, J=10.4, 1.2 Hz, 1H), 5.41 (dd, J=17.2, 1.6 Hz, 1H), 3.36 (quintet, J=5.6 Hz, 1H), 3.22 (quintet, J=5.2 Hz, 1H), 2.93 (d, J=4.8 Hz, 2H), 2.04 (t, J=5.6 Hz, 2H). $^{13}$C NMR (100.59 MHz, CDCl$_3$) δ 145.33, 140.05, 135.06, 129.01, 128.34, 127.87, 127.04, 126.94, 122.76, 118.00, 115.66, 111.16, 63.52, 44.51, 28.40, 22.29. Anal. Calcd for C$_{18}$H$_{19}$N: C, 86.70; H, 7.68; N, 5.62. Found: C, 86.48; H, 7.66; N, 5.50.

Etherification Reaction

General Procedures:

$^1$H NMR spectra were recorded at 400 or 500 MHz with CDCl$_3$ as solvent. $^{13}$C{$^1$H} NMR spectra were obtained at 100.59 MHz in CDCl$_3$. Carbon types were determined from DEPT $^{13}$C NMR experiments. The following abbreviations are used to indicate signal multiplicity: s, singlet; d, doublet; t, triplet; q, quartet; m, multiplet; br, broad. Optical rotations were measured with a 10 cm cell (concentration c given in g/100 mL). Absolute configuration of the products was determined by correlation with compounds published previously. Elemental Analyses were performed by Robertson Microlit Laboratories, Inc., Madison, N.J. 07940. All reactions were conducted using standard Schlenk and drybox techniques. THF, Et$_2$O, and toluene were distilled from sodium-benzophenone ketyl under nitrogen. All other solvents were purchased as anhydrous grade and were used without further purification. Thin-layer chromatography (TLC) was performed on silica gel plates, and components were visualized by observation under LTV light or by treating the plates with phosphomolybdic reagent followed by heating. Flash chromatography was performed on silica gel, unless otherwise stated. Drying of solutions was performed with anhydrous Na$_2$SO$_4$. Concentrations of solutions were conducted with a rotary evaporator.

[Ir(cod)Cl]$_2$, O,O'-(R)-(1,1'-Dinaphthyl-2,2'-diyl)-N,N'-di-(R,R)-phenylethylphosphoramidite were prepared according to published procedures (Herde, J. L.; Lambert, J. C.; Senoff, C. V. *Inorg. Synth.* 1974, 15, 18; Alexakis, A.; Rosset, S.; Allamand, J.; March, S.; Guillen, F.; Benhaim, C. *Synlett* 2001, 1375). Lithium aryloxides were prepared by reaction of the corresponding phenols with n-BuLi in THF at 0° C. After being stirred for 10 min at room temperature, the solution was concentrated under vacuum to afford the corresponding lithium aryloxides as white powders, which were stored under inert atmosphere. All allylic carbonates were synthesized by the reaction of the corresponding allylic alcohols with the corresponding alkylchloroformate in the presence of pyridine. (E)-4-Methoxycinnamamyl alcohol and (E)-2-methoxycinnamyl alcohol were prepared by the reduction of the corresponding aldehydes with DIBAL-H (Nung Min, Y.; Young Soo, G. *J. Org. Chem.* 1985, 50, 2443). Phenols, (E)-4-methoxycinnamaldehyde, and (E)-2-methoxycinnamaldehyde were purchased from Aldrich Chemicals Co. and used without further purification.

General Procedure for the Enantioselective Allylic Etherification Catalyzed by Iridium-Phosphoramidite Complex.

(−)-1-phenyl-1-phenoxy-2-propene: The reaction of lithium phenoxide (LiOPh) with cinnamyl methylcarbonate is used as example. In a drybox, [Ir(cod)Cl]$_2$ (6.7 mg, 0.010 mmol), phosphoramidite ligand L1 (10.8 mg, 0.020 mmol) and lithium phenoxide (200 mg, 2.0 mmol) were dissolved in THF (2 mL) in a screw-capped vial containing a small stirbar. The vial was sealed with a cap containing a PTFE septum and removed from the drybox. Cinnamyl methylcarbonate (192 mg, 1.0 mmol) was added to the reaction mixture by syringe. After being stirred at 50° C. for 20 h, the reaction mixture was poured into brine, extracted with Et$_2$O, dried, filtered, and concentrated. $^1$H NMR analysis of the mixture indicated the ratio of regioisomers to be 96/4. The residue was purified by flash chromatographyy on silica gel (1% Et$_2$O/Hexanes) to afford 182 mg of the major product as a viscous oil. [86%, R$_f$ 0.85 (5% Et$_2$O/Hexanes)]. [α]D$^{20}$=−8.9 (c 1.4, CHCl$_3$); $^1$H NMR (500 MHz, CDCl$_3$) δ 7.48-7.27 (m, 8H), 7.01-6.96 (m, 2H), 6.15 (ddd, J=17.2, 10.4, 5.9 Hz, 1H), 5.70 (d, J=5.9 Hz, 1H), 5.41 (d, J=17.2 Hz, 1H), 5.31 (d, J=10.4 Hz, 1H). $^{13}$C NMR (125.77 MHz, CDCl$_3$) δ 157.9 (C), 140.1 (C), 137.6 (CH), 129.3 (CH), 128.6 (CH), 127.8 (CH), 126.6 (CH), 121.0 (CH), 116.5 (CH$_2$), 116.2 (CH), 80.8 (CH). Anal. Calc. for C$_{15}$H$_{14}$O: C, 85.68; H, 6.71. Found: C, 85.86; H, 7.00. HPLC analysis indicated an enantiomeric excess of 96% [Chiralcel® OJ-H column, eluting with 99.7:0.3 hexane/i-PrOH, 0.8 mL/min, 220 nm; minor enantiomer t$_R$, 39.1, major enantiomer t$_R$ 47.1 min].

(R)-(−)-1-phenyl-1-(2-methylphenoxy)-2-propene (Trost, B. M.; Fraise, P. L.; Ball, Z. T. *Angew. Chem., Int. Ed.* 2002, 41, 1059): The general procedure was followed with lithium 2-methylphenoxide (228 mg, 2.0 mmol). The reaction was conducted at 50° C. for 14 h. $^1$H NMR analysis of the mixture indicated the ratio of regioisomers to be 96/4. The residue was purified by flash chromatography on silica gel (1-2% Et$_2$O/Hexanes) to afford 196 mg of the title compound as a viscous oil. [87%, R$_f$ 0.88 (5% Et$_2$O/Hexanes)]. The absolute configuration was determined by comparison of the optical rotation with the literature data: [α]$_D$$^{20}$=−7.3 (c 0.84, CHCl$_3$), lit.$^3$ [α]$_D$$^{23}$=−6.9 (c 1.0, CHCl$_3$) $^1$H NMR (500 MHz, CDCl$_3$) δ 7.52 (d, J=7.3 Hz, 2H), 7.46 (m, 2H), 7.38 (m, 1H), 7.25 (d, J=7.3 Hz, 1H), 7.13 (m, 1H), 6.94 (t, J=7.4 Hz, 1H), 6.89 (d, J=8.1 Hz, 1H), 6.20 (ddd, J=17.1, 10.4, 5.8 Hz, 1H), 5.74 (d, J=5.8 Hz, 1H), 5.48 (d, J=17.1 Hz, 1H), 5.34 (d, J=10.4 Hz, 1H), 2.44 (s, 3H); $^{13}$C NMR (125.77 MHz, CDCl$_3$) δ 155.9 (C), 140.5 (C), 138.3 (CH), 130.7 (CH), 128.6 (CH), 127.7 (CH), 127.5 (C), 126.5 (CH), 126.4 (CH), 120.6 (CH), 115.9 (CH$_2$), 113.4 (CH), 80.6 (CH), 16.6 (CH$_3$); Anal. Calc. for C$_{16}$H$_{16}$O: C, 85.68; H, 7.19. Found: C, 85.47; H, 7.10. HPLC analysis indicated an enantiomeric excess of 95% [Chiralcel® OD-H column, eluting with 99.85:0.15 hexane/i-PrOH, 0.7 mL/min, 220 nm; (S) enantiomer t$_R$, 16.6, (R) enantiomer t$_R$ 19.4 min].

(+)-1-phenyl-1-(4-methylphenoxy)-2-propene: The general procedure was followed with lithium 4-methylphenoxide (228 mg, 2.0 mmol). The reaction was conducted at 50° C. for 22 h. $^1$H NMR analysis of the mixture indicated the ratio of regioisomers to be 98/2. The residue was purified by flash chromatography on silica gel (1-2% Et$_2$O/Hexanes) to afford 203 mg of the title compound as a viscous oil. [91%, R$_f$ 0.85 (5% Et$_2$O/Hexanes)].[α]$_D$$^{20}$=+5.0 (c 1.3, CHCl$_3$). $^1$H NMR (500 MHz, CDCl$_3$) δ 7.47 (d, J=7.3 Hz, 2H), 7.42 (t, J=7.4 Hz, 2H), 7.34 (m, 1H), 7.08 (d, J=8.1 Hz, 2H), 6.90 (d, J=8.1 Hz, 2H), 6.16 (ddd, J=17.2, 10.4, 5.9 Hz, 1H), 5.66 (d, J=5.9 Hz, 1H), 5.40 (d, J=17.2 Hz, 1H), 5.31 (d, J=10.4 Hz, 1H), 2.32 (s, 3H); $^{13}$C NMR (125.77 MHz, CDCl$_3$) δ 155.8 (C), 140.3 (C), 138.1 (CH), 130.2 (C), 129.8 (CH), 128.6 (CH), 127.7 (CH), 126.6 (CH), 116.4 (CH$_2$), 116.1 (CH), 81.0 (CH), 20.5 (CH$_3$); Anal. Calc. for C$_{16}$H$_{16}$O: C, 85.68; H, 7.19. Found: C, 85.91; H, 7.48. HPLC analysis indicated an enantiomeric excess of 95% [Chiralcel® OD-H column, eluting with 99.85:0.15 hexane/i-PrOH, 0.6 mL/min, 220 nm; minor enantiomer t$_R$, 18.1, major enantiomer t$_R$ 19.4 min].

(+)-1-phenyl-1-(4-methoxyphenoxy)-2-propene: The general procedure was followed with lithium 4-methoxyphenoxide (260 mg, 2.0 mmol). The reaction was conducted at 50° C. for 8 h. $^1$H NMR analysis of the mixture indicated the ratio of regioisomers to be 98/2. The residue was purified by flash chromatography on silica gel (1-4% Et$_2$O/Hexanes) to afford 210 mg of the title compound as a viscous oil. [88%, R$_f$ 0.65 (5% Et$_2$O/Hexanes)].[α]$_D$$^{20}$=+6.6 (c 1.4, CHCl$_3$). $^1$H NMR (500 MHz, CDCl$_3$) δ 7.45 (m, 4H), 7.35 (m, 1H), 6.95(d, J=9.0 Hz, 2H), 6.84 (d, J=9.0 Hz, 2H), 6.17 (ddd, J=17.2, 10.4, 5.2 Hz, 1H), 5.60 (d, J=5.2 Hz, 1H), 5.40 (d, J=17.2 Hz, 1H), 5.32 (d, J=10.4 Hz, 1H), 3.80 (s, 3H); $^{13}$C NMR (125.77 MHz, CDCl$_3$) δ 154.0 (C), 152.0 (C), 140.3 (C), 138.2 (CH), 128.5 (CH), 127.7 (CH), 126.6 (CH), 117.4 (CH), 116.4 (CH$_3$), 114.4 (CH), 81.8 (CH), 55.5 (CH$_3$); Anal. Calc. for C$_{16}$H$_{16}$O$_2$: C, 79.97; H, 6.71. Found: C, 80.22; H, 6.72. HPLC analysis indicated an enantiomeric excess of 97% [Chiralcel® OD-H column, eluting with 97:3 hexane/i-PrOH, 0.8 mL/min, 220 nm; minor enantiomer t$_R$, 17.9, major enantiomer t$_R$ 16.3 min].

(−)-1-phenyl-1-(3-methoxyphenoxy)-2-propene: The general procedure was followed with lithium 3-methoxyphenoxide (260 mg, 2.0 mmol). The reaction was conducted at 50° C. for 17 h. $^1$H NMR analysis of the mixture indicated the ratio of regioisomers to be 95/5. The residue was purified by flash chromatography on silica gel (1-4% Et$_2$O/Hexanes) to afford 218 mg of the title compound as a viscous oil. [84%, R$_f$ 0.65 (5% Et$_2$O/Hexanes)].[α]$_D$$^{20}$=−15.3 (c 0.8, CHCl$_3$). $^1$H NMR (500 MHz, CDCl$_3$) δ 7.54 (d, J=7.3 Hz, 2H), 7.48 (m, 2H), 7.40 (m, 1H), 7.25 (t, J=8.5 Hz, 1H), 6.68 (m, 2H), 6.61 (m, 1H), 6.23 (ddd, J=17.1, 10.4, 5.9, 1H), 5.76 (d, J=5.9 Hz, 1H), 5.48 (d, J=17.1 Hz, 1H), 5.38 (d, J=10.4 Hz, 1H), 3.84 (s, 3H); $^{13}$C NMR (125.77 MHz, CDCl$_3$) δ 161.3 (C), 159.7 (C), 140.7 (C), 138.5 (CH), 103.3 (CH), 129.2 (CH), 128.4 (CH), 127.2 (CH), 117.1 (CH$_2$), 108.9 (CH), 107.2 (CH), 103.2 (CH), 81.4 (CH), 55.7 (CH$_3$); Anal. Calc. for C$_{16}$H$_{16}$O$_2$: C, 79.97; H, 6.71. Found: C, 80.25; H, 6.47. HPLC analysis indicated an enantiomeric excess of 96% [Chiralcel® OJ-H column, eluting with 97:3 hexane/i-PrOH, 0.7 mL/min, 220 nm; minor enantiomer $t_R$, 68.2, major enantiomer $t_R$ 89.0 min].

(−)-1-phenyl-1-(3-phenylphenoxy)-2-propene: The general procedure was followed with lithium 3-phenylphenoxide (352 mg, 2.0 mmol). The reaction was conducted at 50° C. for 13 h. $^1$H NMR analysis of the mixture indicated the ratio of regioisomers to be 96/4. The residue was purified by flash chromatography on silica gel (1-2% Et$_2$O/Hexanes) to afford 218 mg of the title compound as a viscous oil. [76%, R$_f$ 0.76 (5% Et$_2$O/Hexanes)]. $[\alpha]_D^{20}$=−2.5 (c 1.1, CHCl$_3$). $^1$H NMR (400 MHz, CDCl$_3$) δ 7.66-7.26 (m, 14H), 6.24 (ddd, J=17.1, 10.4, 5.9 Hz, 1H), 5.82 (d, J=5.9 Hz, 1H), 5.50 (d, J=17.1 Hz, 1H), 5.39 (d, J=10.4 Hz, 1H); $^{13}$C NMR (100.59 MHz, CDCl$_3$) δ 158.2 (C), 142.5 (C), 140.9 (C), 140.0 (C), 137.8 (CH), 129.6 (CH), 128.7 (CH), 128.6 (CH), 127.8 (CH), 127.3 (CH), 127.1 (CH), 126.6 (CH), 119.9 (CH), 116.6 (CH$_2$), 115.2 (CM), 114.7 (CH), 80.9 (CH); Anal. Calc. for C$_{21}$H$_{18}$O: C, 88.08; H, 6.34. Found: C, 87.85; H, 6.37. HPLC analysis indicated an enantiomeric excess of 95% [Chiralcel® OJ-H column, eluting with 98:2 hexane/i-PrOH, 0.6 mL/min, 220 nm; minor enantiomer $t_R$, 45.5, major enantiomer $t_R$ 55.4 min].

(−)-1-phenyl-1-(2-phenylphenoxy)-2-propene: The general procedure was followed with lithium 2-phenylphenoxide (352 mg, 2.0 mmol). The reaction was conducted at 50° C. for 10 h. $^1$H NMR analysis of the mixture indicated the ratio of regioisomers to be 96/4. The residue was purified by flash chromatography on silica gel (1-2% Et$_2$O/Hexanes) to afford 187 mg of the title compound as a viscous oil. [65%, R$_f$ 0.76 (5% Et$_2$O/Hexanes)]. $[\alpha]_D^{20}$=−42 (c 1.0, CHCl$_3$). $^1$H NMR (400 MHz, CDCl$_3$) δ 7.70-7.02 (m, 14H), 6.08 (m, 1H), 5.71 (d, J=5.6 Hz, 1H), 5.35 (d, J=17.1 Hz, 1H), 5.24 (d, J=10.4 Hz, 1H); $^{13}$C NMR (100.59 MHz, CDCl$_3$) δ 154.5 (C), 140.1 (C), 138.7 (C), 138.1 (CH), 131.9 (C), 130.9 (CH), 129.7 (CH), 128.5 (CH), 128.3 (CH), 127.8 (CH), 127.6 (CH), 126.8 (CH), 126.4 (CH), 121.3 (CH), 115.9 (CH$_2$), 115.3 (CH), 81.6 (CH); Anal. Calc. for C$_{21}$H$_{18}$O: C, 88.08; H, 6.34. Found: C, 87.79; H, 6.15. HPLC analysis indicated an enantiomeric excess of 93% [Chiralcel® OJ-H column, eluting with 99.9:0.01 heptane/i-PrOH, 0.6 mL/min, 220 nm; minor enantiomer $t_R$, 29.6, major enantiomer $t_R$ 34.2 min].

(−)-1-phenyl-1-(3-dimethylaminophenoxy)-2-propene: The general procedure was followed with lithium 3-dimethylaminophenoxide (274 mg, 2.0 mmol). The reaction was conducted at 50° C. for 14 h. $^1$H NMR analysis of the mixture indicated the ratio of regioisomers to be 99/1. The residue was purified by flash chromatography on silica gel (1-5% Et$_2$O/Hexanes) to afford 142 mg of the title compound as a viscous oil. [56%, R$_f$ 0.45 (5% Et$_2$O/Hexanes)]. $[\alpha]_D^{20}$=−13.9 (c 0.82, CHCl$_3$) $^1$H NMR (500 MHz, CDCl$_3$) δ 7.45 (d, J=7.4 Hz, 1H), 7.38 (m, 2H), 7.31 (t, J=7.3 Hz, 1H), 7.10 (t, J=8.2 Hz, 2H), 6.40 (s, 1H), 6.36 (m, 2H), 6.15 (ddd, J=17.1, 10.4, 5.9 Hz, 1H), 5.68 (d, J=5.9 Hz, 1H), 5.38 (d, J=17.1 Hz, 1H), 5.28 (d, J=10.4 Hz, 1H), 2.93 (s, 6H); $^{13}$C NMR (125.77 MHz, CDCl$_3$) δ 159.0 (C), 151.8 (C), 140.5 (C), 138.2 (CH), 129.5 (CH), 128.6 (CH), 127.7 (CH), 126.6 (CH), 116.4 (CH$_2$), 105.9 (CH), 103.8 (CH), 101.2 (CH), 80.7 (CH), 40.5 (CH$_3$); Anal. Calc. for C$_{17}$H$_{19}$NO: C, 80.60; H, 7.56, N, 5.53. Found: C, 80.74; H, 7.63; N, 5.28. HPLC analysis indicated an enantiomeric excess of 97% [Chiralcel® OJ-H column, eluting with 96:4 hexane/i-PrOH, 0.8 mL/min, 220 nm; minor enantiomer $t_R$ 29.1, major enantiomer $t_R$ 35.5 min].

(−)-1-phenyl-1-[(3,4-methyenedioxy)phenoxy]-2-propene: The general procedure was followed with lithium (3,4-methyenedioxy)phenoxide (288 mg, 2.0 mmol). The reaction was conducted at 50° C. for 18 h. $^1$H NMR analysis of the mixture indicated the ratio of regioisomers to be 99/1. The residue was purified by flash chromatography on silica gel (1-5% Et$_2$O/Hexanes) to afford 165 mg of the title compound as a viscous oil. [65%, R$_f$ 0.60 (5% Et$_2$O/Hexanes)]. $[\alpha]_D^{RT}$=−24.3 (c 1.1, CHCl$_3$) $^1$H NMR (500 MHz, CDCl$_3$) δ 7.47-7.28 (m, 5H), 6.66 (d, J=8.5 Hz, 1H), 6.55 (d, J=2.5 Hz, 1H), 6.38 (dd, J=8.5, 2.5 Hz, 1H), 6.10 (ddd, J=17.2, 10.3, 6.1 Hz, 1H), 5.9 (s, 2H), 5.51 (d, J=6.1 Hz, 1H), 5.34 (d, J=17.2 Hz, 1H), 5.27 (d, J=10.3 Hz, 1H); $^{13}$C NMR (100.59 MHz, CDCl$_3$) δ 153.3 (C), 148.1 (C), 141.9 (C), 140.2 (C), 138.0 (CH), 128.7 (CH), 127.9 (CH), 126.6 (CH), 116.6 (CH$_2$), 108.1 (CH), 108.0 (CH), 106.1 (CH), 101.2 (CH$_2$), 82.3 (CH). Anal. Calc. for C$_{16}$H$_{14}$O$_3$: C, 75.57, H, 5.55. Found: C, 75.55; H, 5.51. HPLC analysis indicated an enantiomeric excess of 94% [Chiralcel® OJ-H column, eluting with 98:2 hexane/i-PrOH, 0.7 mL/min, 220 nm; minor enantiomer $t_R$, 71.8, major enantiomer $t_R$ 79.1 min].

(+)-1-phenyl-1-(2,4-dimethylphenoxy)-2-propene: The general procedure was followed with lithium 2,4-dimethylphenoxide (256 mg, 2.0 mmol). The reaction was conducted at 50° C. for 11 h. $^1$H NMR analysis of the mixture indicated the ratio of regioisomers to be 98/2. The residue was purified by flash chromatography on silica gel (1-2% Et$_2$O/Hexanes) to afford 202 mg of the title compound as a viscous oil. [85%, R$_f$ 0.89 (4% Et$_2$O/Hexanes)].$[\alpha]_D^{20}$=+4.4 (c 1.3, CHCl$_3$). $^1$H NMR (500 MHz, CDCl$_3$) δ 7.48 (m, 2H), 7.41 (m, 2H), 7.33 (m, 1H), 7.02 (s, 1H), 6.89 (d, J=8.2 Hz, 1H), 6.73 (d, J=8.2 Hz, 1H), 6.14 (ddd, J=17.2, 10.4, 5.9 Hz, 1H), 5.64 (d, J=5.8 Hz, 1H), 5.42 (d, J=17.2 Hz, 1H), 5.28 (d, J=10.4 Hz, 1H), 2.35 (s, 3H), 2.29 (s, 3H); $^{13}$C NMR (125.77 MHz, CDCl$_3$) δ 153.8 (C), 140.7 (C), 138.5 (CH), 131.5 (CH), 129.8 (C), 128.5 (CH), 127.6 (CH), 127.3 (C), 126.6 (CH), 126.4 (CH), 115.9 (CH$_2$), 113.6 (CH), 80.9 (CH), 20.4 (CH$_3$), 16.5 (CH$_3$); Anal. Calc. for C$_{17}$H$_{18}$O: C, 85.67; H, 7.61. Found: C, 85.69; H, 7.56. HPLC analysis indicated an enantiomeric excess of 95% [Chiralcel® OJ-H column, eluting with 99.9:0.1 hexane/i-PrOH, 0.6 mL/min, 220 nm; minor enantiomer $t_R$, 27.4, major enantiomer $t_R$ 29.2 min].

(−)-1-phenyl-1-(2,4,6-trimethylphenoxy)-2-propene: The general procedure was followed with lithium 2,4,6-trimethylphenoxide (284 mg, 2.0 mmol). The reaction was conducted at 50° C. for 22 h. $^1$H NMR analysis of the mixture indicated the ratio of regioisomers to be 93/7. The residue was purified by flash chromatography on silica gel (1-2% Et$_2$O/Hexanes) to afford 207 mg of the title compound as a viscous oil. [82%, R$_f$ 0.90 (5% Et$_2$O/Hexanes)].$[\alpha]_D^{20}$=−8.8 (c 1.4, CHCl$_3$). $^1$H NMR (500 MHz, CDCl$_3$) δ 7.51 (m, 2H), 7.44-7.38 (m, 3H), 6.85 (s, 2H), 6.21 (m, 1H), 5.32 (d, J=16.1 Hz, 1H), 5.30-5.24 (m, 2H), 2.30 (s, 3H), 2.19 (s, 6H); $^{13}$C NMR (125.77 MHz, CDCl$_3$) δ 152.6 (C), 140.8 (C), 138.0 (CH), 132.7 (C), 130.9 (C), 129.4 (CH), 128.3 (CH), 127.8 (CH), 127.2 (CH), 116.9 (CH$_2$), 85.5 (CH), 20.6 (CH$_3$), 17.2 (CH$_3$); Anal. Calc. for C$_{18}$H$_{20}$O: C, 85.67; H, 7.99. Found: C, 85.77; H, 7.86. HPLC analysis indicated an enantiomeric excess of 93% [Chiralcel® OD-H column, eluting with 99.9:0.1 hexane/i-PrOH, 0.6 mL/min, 220 nm; minor enantiomer $t_R$, 20.4, major enantiomer $t_R$ 25.6 min].

(+)-1-phenyl-1-(4-bromophenoxy)-2-propene: The general procedure was followed with sodium 4-bromophenoxide (390 mg, 2.0 mmol). The reaction was conducted at 50° C. for 8 h. $^1$H NMR analysis of the mixture indicated the ratio of regioisomers to be 96/4. The residue was purified by flash chromatography on silica gel (1-4% Et$_2$O/Hexanes) to afford 262 mg of the title compound as a viscous oil. [91%, R$_f$ 0.75 (5% Et$_2$O/Hexanes)]. $[\alpha]D^{20}$=+12.7 (c 1.2, CHCl$_3$). $^1$H NMR (500 MHz, CDCl$_3$) δ 7.45-7.33 (m, 7H), 6.88 (d, J=9.0 Hz, 2H), 6.13 (ddd, J=17.2, 10.4, 5.9 Hz, 1H), 5.63 (d, J=5.9 Hz, 1H), 5.40 (d, J=17.2 Hz, 1H), 5.31 (d, J=10.4 Hz, 1H); $^{13}$C NMR (125.77 MHz, CDCl$_3$) δ 156.9 (C), 139.6 (C), 137.5 (CH), 132.1 (CH), 128.6 (CH), 128.0 (CH), 126.5 (CH), 118.0 (CH), 116.7 (CH$_2$), 113.2 (C), 81.1 (CH); Anal. Calc. for C$_{15}$H$_{13}$BrO: C, 62.30, H, 4.53. Found: C, 62.58; H, 4.70. HPLC analysis indicated an enantiomeric excess of 90% [Chiralcel® OJ-H column, eluting with 99.7:0.3 hexane/i-PrOH, 0.8 mL/min, 220 nm; minor enantiomer t$_R$, 31.2, major enantiomer t$_R$, 35.7 min].

(+)-1-phenyl-1-(4-chlorophenoxy)-2-propene: The general procedure was followed with sodium 4-chlorophenoxide (300 mg, 2.0 mmol). The reaction was conducted at 50° C. for 20 h. $^1$H NMR analysis of the mixture indicated the ratio of regioisomers to be 93/7. The residue was purified by flash chromatography on silica gel (1-3% Et$_2$O/Hexanes) to afford 210 mg of the title compound as a viscous oil. [86%, R$_f$ 0.72 (5% Et$_2$O/Hexanes)]. [α]$_D^{20}$=+10.1 (c 1.1, CHCl$_3$). $^1$H NMR (500 MHz, CDCl$_3$) δ 7.47-7.24 (m, 7H), 6.93 (d, J=8.3 Hz, 2H), 6.15 (ddd, J=17.3, 10.4, 5.8 Hz, 1H), 5.65 (d, J=5.8 Hz, 1H), 5.41 (d, J=17.3 Hz, 1H), 5.33 (d, J=10.4 Hz, 1H); $^{13}$C NMR (125.77 MHz, CDCl$_3$) δ 156.9 (C), 140.1 (C), 138.1 (CH), 129.7 (CH), 129.2 (CH), 128.5 (CH), 127.1 (CH), 126.4 (C), 118.0 (CH), 117.2 (CH$_2$), 81.8 (CH); Anal. Calc. for C$_{15}$H$_{13}$ClO: C, 73.62; H, 5.35. Found: C, 73.61; H, 5.08. HPLC analysis indicated an enantiomeric excess of 92% [Chiralcel® OJ-H column, eluting with 99.7:0.3 hexane/i-PrOH, 0.8 mL/min, 220 nm; minor enantiomer t$_R$, 30.7, major enantiomer t$_R$ 36.5 min].

(−)-1-phenyl-1-(3-methyl,4-bromophenoxy)-2-propene: The general procedure was followed with sodium 3-methyl, 4-bromophenoxide (418 mg, 2.0 mmol). The reaction was conducted at 50° C. for 8 h. $^1$H NMR analysis of the mixture indicated the ratio of regioisomers to be 95/5. [89%, R$_f$ 0.79 (7% Et$_2$O/Hexanes))]. $^1$H NMR (500 MHz, CDCl$_3$) δ 7.46-7.33 (m, 6H), 6.92 (s, 1H), 6.69 (d, J=8.7 Hz, 1H), 6.13 (ddd, J=17.2, 10.4, 5.8 Hz, 1H), 5.64 (d, J=5.8 Hz, 1H), 5.39 (d, J=17.2 Hz, 1H), 5.32 (d, J=10.4 Hz, 1H), 2.38 (s, 3H); $^{13}$C NMR (125.77 MHz, CDCl$_3$) δ 157.0 (C), 139.7 (C), 138.7 (C), 137.6 (CH), 132.7 (CH), 128.6 (CH), 127.9 (CH), 126.5 (CH), 118.9 (CH), 116.6 (CH$_2$), 115.8 (C), 115.0 (CH), 81.0 (CH), 23.1 (CH3); Anal. Calc. for C$_{16}$H$_{15}$BrO: C, 63.38, H, 4.99. Found: C, 63.72; H, 5.24. HPLC analysis indicated an enantiomeric excess of 87%. [Chiralcel® OJ-H column, eluting with 99.9:0.1 hexane/i-PrOH, 0.6 mL/min, 220 nm; minor enantiomer t$_R$, 72, major enantiomer t$_R$ 79 min].

(R)-(−)-1-phenyl-1-(4-trifluoromethylphenoxy)-2-propene (Trost, B. M.; Fraise, P. L.; Ball, Z. T. *Angew. Chem., Int. Ed.* 2002, 41, 1059): The general procedure was followed with sodium 4-trifluoromethylphenoxide (368 mg, 2.0 mmol). The reaction was conducted at 50° C. for 10 h. $^1$H NMR analysis of the mixture indicated the ratio of regioisomers to be 90/10. The residue was purified by flash chromatography on silica gel (1-2% Et$_2$O/Hexanes) to afford 256 mg of the title compound as a viscous oil. [92%, R$_f$ 0.69 (5% Et$_2$O/Hexanes)]. The absolute configuration was determined by comparison of the optical rotation with the literature data: [α]$_D^{20}$=−6.7 (c 1.3, CHCl$_3$), lit.$^3$ [α]$_D^{23}$=−7.4 (c 1.0, CHCl$_3$). $^1$H NMR (500 MHz, CDCl$_3$) δ 7.60-7.23 (m, 7H), 7.04 (d, J=8.5 Hz, 2H), 6.14 (ddd, J=17.1, 10.5, 5.8 Hz, 1H), 5.72 (d, J=5.8 Hz, 1H), 5.41 (d, J=17.1 Hz, 1H), 5.32 (d, J=10.4 Hz, 1H); $^{13}$C NMR (125.77 MHz, CDCl$_3$) δ 160.3, 139.3, 137.3, 128.8, 128.2, 126.7 (q, J=10.9 Hz), 126.6, 123.3 (q, J=33 Hz), 116.9, 116.0, 81.0. The quaternary carbon of CF$_3$ could not be detected. Anal. Calc. for C$_{16}$H$_{13}$F$_3$O: C, 69.06; H, 4.71. Found: C, 69.03; H, 4.71. HPLC analysis indicated an enantiomeric excess of 80% [Chiralcel® OJ-H column, eluting with 99.7:0.3 hexane/i-PrOH, 0.7 mL/min, 220 nm; (S) enantiomer t$_R$, 21.5, (R) enantiomer t$_R$ 26.2 min].

(−)-1-(2-Methoxyphenyl)-1-phenoxy-2-propene: The general procedure was followed with lithium phenoxide (300 mg, 3.0 mmol) and 2-methoxycinnamyl methylcarbonate (222 mg, 1.0 mmol) in THF (2 mL). The reaction was conducted at 50° C. for 41 h. $^1$H NMR analysis of the mixture indicated the ratio of regioisomers 4/5 to be 98/2. The residue was purified by flash chromatography on silica gel (1-3% Et$_2$O/Hexanes) to afford 190 mg of the title compound as a viscous oil. [79%, R$_f$ 0.60 (5% Et$_2$O/Hexanes)].[α]$_D^{20}$=−31.0 (c 0.82, CHCl$_3$). $^1$H NMR (500 MHz, CDCl$_3$) δ 7.54 (d, J=7.5 Hz, 1H), 7.32 (m, 3H), 7.05-6.96 (m, 5H), 6.21 (m, 2H), 5.45 (dt, J=15.9, 1.2 Hz, 1H), 5.28 (d, J=9.3 Hz, 1H), 3.96 (s, 3H); $^{13}$C NMR (125.77 MHz, CDCl$_3$) δ 157.9 (C), 156.1 (C), 137.2 (CH), 129.2 (CH), 128.7 (CH), 128.4 (C), 127.1 (CH), 121.0 (CH), 120.6 (CH), 115.8 (CH), 115.4 (CH$_2$), 110.5 (CH), 73.9 (CH), 55.5 (CH$_3$); Anal. Calc. for C$_{16}$H$_{16}$O$_2$: C, 79.97; H, 6.71. Found: C, 80.07; H, 6.52. HPLC analysis indicated an enantiomeric excess of 75% [Chiralcel® OD-H column, eluting with 99.9:0.1 hexane/i-PrOH, 0.6 mL/min, 254 nm; major enantiomer t$_R$, 29.6, minor enantiomer t$_R$ 35.0 min].

(+)-1-(4-Methoxyphenyl)-1-phenoxy-2-propene: The general procedure was followed with lithium phenoxide (300 mg, 3.0 mmol) and 4-methoxycinnamyl methylcarbonate (222 mg, 1.0 mmol) in THF (1 mL). The reaction was conducted at 50° C. for 13 h. $^1$H NMR analysis of the mixture indicated the ratio of regioisomers to be 97/3. The residue was purified by flash chromatography on silica gel (pre-coated with 1% Et$_3$N/hexanes) (1-3% Et$_2$O/Hexanes) to afford 169 mg of the title compound as a viscous oil. [70%, R$_f$ 0.62 (5% Et$_2$O/Hexanes)].[α]$_D^{20}$=+9.4 (c 0.8, CHCl$_3$). $^1$H NMR (500 MHz, CDCl$_3$) δ 7.37 (d, J=8.6 Hz, 2H), 7.27 (m, 2H), 6.94 (m, 5H), 6.14 (ddd, J=17.3, 10.4, 5.8, 1H), 5.64 (d, J=5.8 Hz, 1H), 5.36 (dt, J=17.3, 1.2 Hz, 1H), 5.29 (dt, J=10.4, 1.2 Hz, 1H), 3.84 (s, 3H); $^{13}$C NMR (125.77 MHz, CDCl$_3$) δ 159.2 (C), 157.9 (C), 138.1 (CH), 132.2 (C), 129.3 (CH), 128.0 (CH), 120.9 (CH), 116.2 (CH$_2$), 116.2 (CH), 114.0 (CH), 80.4 (CH), 55.3 (CH$_3$); Anal. Calc. for C$_{16}$H$_{16}$O$_2$: C, 79.97; H, 6.71. Found: C, 79.78; H, 6.92. HPLC analysis indicated an enantiomeric excess of 86% [Chiralcel® OD-H column, eluting with 99.9:0.1 hexane/i-PrOH, 0.6 mL/min, 254 nm; major enantiomer t$_R$, 44.8, minor enantiomer t$_R$ 48.1 min].

(−)-i-Propyl allyloxybenzene (Evans, P. A.; Leahy, D. K. *J. Am. Chem. Soc.* 2000, 122, 5012): The general procedure was followed with lithium phenoxide (200 mg, 2.0 mmol) and 2-hexenyl methylcarbonate (160 mg, 1.0 mmol) in THF (2 mL). The reaction was conducted at 50° C. for 14 h. $^1$H NMR analysis of the mixture indicated the ratio of regioisomers to be 92/8. The residue was purified by flash chromatography on silica gel (0-1% Et$_2$O/Hexanes) to afford 162 mg of the title compound as an oil. [93%, R$_f$ 0.90 (5% Et$_2$O/Hexanes)]. $^1$H NMR (500 MHz, CDCl$_3$) δ 7.23 (m, 2H), 6.91 (m, 3H), 5.84 (ddd, J=17.3, 10.6, 6.2 Hz, 1H), 5.25 (d, J=17.4 Hz, 1H), 5.20 (d, J=10.6 Hz, 1H), 4.59 (dt, J=6.8, 6.0 Hz, 1H), 1.83-1.74 (m, 1H), 1.68-1.61 (m, 1H), 1.58-1.38 (m, 2H), 0.96 (t, J=7.4 Hz, 3H); $^{13}$C NMR (125.77 MHz, CDCl$_3$) δ 158.4, 138.2, 129.3, 120.6, 116.2, 116.0, 78.6, 37.7, 18.6, 14.0. HPLC analysis indicated an enantiomeric excess of 92% [Chiralcel® OD-H column, eluting with 99.9:0.1 hexane/i-PrOH, 0.6 mL/min, 220 nm; major enantiomer t$_R$, 13.3, minor enantiomer t$_R$ 15.8 min].

(−)-1-Methyl-2-(1-propylallyloxy)benzene (Evans, P. A.; Leahy, D. K. *J. Am. Chem. Soc.* 2000, 122, 5012): The general procedure was followed with lithium 2-methylphenoxide (228 mg, 2.0 mmol) and 2-hexenyl methylcarbonate (160 mg, 1.0 mmol) in THF (2 mL). The reaction was conducted at 50° C. for 20 h. $^1$H NMR analysis of the mixture indicated the ratio of regioisomers to be 87/13. The residue was purified by flash chromatography on silica gel (0-1% Et$_2$O/Hexanes) to afford 165 mg of the title compound as an oil. [86%, R$_f$ 0.92 (5% Et$_2$O/Hexanes)].[α]$_D^{20}$=–3.0 (c 0.3, CHCl$_3$). $^1$H NMR (500 MHz, CDCl$_3$) δ 7.16 (m, 2H), 6.88 (m, 2H), 5.92 (ddd, J=17.4, 10.5, 6.1 Hz, 1H), 5.28 (dt, J=17.4, 1.2 Hz, 1H), 5.22 (dt, J=10.5, 1.0 Hz, 1H), 4.67 (dt, J=6.4, 6.1 Hz, 1H), 2.31 (s, 3H), 1.89-1.83 (m, 1H), 1.76-1.69 (m, 1H), 1.60-1.47 (m, 2H), 1.01 (t, J=7.4 Hz, 3H); $^{13}$C NMR (125.77 MHz, CDCl$_3$) δ 156.5 (C), 138.5 (CH), 130.6 (CH), 127.4 (C), 126.4 (CH), 120.2 (CH), 115.9 (CH$_2$), 113.1 (CH), 78.6 (CH), 37.9 (CH$_2$), 18.5 (CH$_2$), 16.4 (CH$_3$), 14.0 (CH$_3$). HPLC analysis indicated an enantiomeric excess of 90% [Chiralcel® OD-H column, eluting with 99.9:0.1 hexane/i-PrOH, 0.6 mL/min, 220 nm; major enantiomer t$_R$, 12.2, minor enantiomer t$_R$ 13.7 min].

(–)-1-Methoxy-4-(1-propylallyloxy)benzene: The general procedure was followed with lithium 4-methoxyphenoxide (260 mg, 2.0 mmol) and 2-hexenyl methylcarbonate (160 mg, 1.0 mmol) in THF (2 mL). The reaction was conducted at 50° C. for 14 h. $^1$H NMR analysis of the mixture indicated the ratio of regioisomers to be 90/10. The residue was purified by flash chromatography on silica gel (1% Et$_2$O/Hexanes) to afford 155 mg of the title compound as an oil. [73%, R$_f$ 0.82 (5% Et$_2$O/Hexanes)].[α]$_D^{20}$–8.2 (c 0.6, CHCl$_3$). $^1$H NMR (500 MHz, CDCl$_3$) δ 6.88 (d, J=9.3 Hz, 2H), 6.84 (d, J=9.2 Hz, 2H), 5.87 (ddd, J=17.3, 10.6, 6.3 Hz, 1H), 5.25 (d, J=17.3 Hz, 1H), 5.21 (d, J=10.6 Hz, 1H), 4.51 (q, J=6.4 Hz, 1H), 3.80 (s, 3H), 1.81 (m, 1H), 1.66 (m, 1H), 1.56-1.46 (m. 2H), 1.00 (t, J=7.3 Hz, 3H); $^{13}$C NMR (125.77 MHz, CDCl$_3$) δ 153.8 (C), 152.5 (C), 138.5 (CH), 117.3 (CH), 116.2 (CH$_2$), 114.4 (CH), 79.9 (CH), 55.6 (CH$_3$), 37.7 (CH$_2$), 18.5 (CH$_2$), 13.9 (CH$_3$); Anal. Calc. for C$_{13}$H$_8$O$_2$: C, 75.69; H, 8.80. Found: C, 75.90, H, 9.07. HPLC analysis indicated an enantiomeric excess of 85% [Chiralcel® OD-H column, eluting with 99.9: 0.1 hexane/i-PrOH, 0.6 mL/min, 220 nm; major enantiomer t$_R$, 24.5, minor enantiomer t$_R$ 27.6 min].

General Procedure for the Enantioselective Allylic Etherification with Lithium Aryloxides Generated In Situ.

(–)-1-phenyl-1-phenoxy-2-propene: The reaction of phenol with cinnamyl methylcarbonate is provided as a representative example. To a solution of phenol (188 mg, 2.0 mmol) in THF (1 mL), a solution of n-BuLi (2.58M in hexanes, 0.78 mL, 2.0 mmol,) was added dropwise at 23° C. After 10 min this solution was added by syringe to a round bottom flask containing [Ir(cod)Cl]$_2$ (6.7 mg, 0.010 mmol), phosphoramidite ligand 1, (10.8 mg, 0.020 mmol) and a small stirbar. After the mixture was stirred for 5 min, cinnamyl methylcarbonate (192 mg, 1.0 mmol) was added to the reaction mixture by syringe. After this final mixture was stirred at 50° C. for 20 h, the reaction mixture was poured into brine, extracted with Et$_2$O, dried, filtered, and concentrated. $^1$H NMR analysis of the mixture indicated the ratio of regioisomers to be 96/4. The residue was purified by flash chromatography on silica gel (1% Et$_2$O/Hexanes) to afford 182 mg of the title compound as a viscous oil. [86%, 96% ee, R$_f$ 0.85 (5% Et$_2$O/Hexanes)]. The same procedure was followed when Cy$_2$NLi (1.0 M in THF) was used instead of n-BuLi.

General Procedure for Reaction Between t-butyl Cinnamyl Carbonate and Primary Alkoxides.

The reaction of lithium ethoxide with t-butyl cinnamyl carbonate is used as an example. In a drybox, LiOEt (39 mg. 0.75 mmol) and CuI (152 mg, 0.800 mmol) were added to a screw-capped vial. THF (0.6 mL) was added, and the suspension was stirred for 30 min. To this suspension was added a THF (0.5 mL) solution of [Ir(cod)Cl]$_2$ (3.4 mg, 0.010 mmol) and (Ra,Rc,Rc)-Ligand L4 (6.4 mg, 0.010 mmol). A small magnetic stirbar was added, and the vial was sealed with a cap containing a PTFE septum and removed from the drybox. The vial was put into an ice-water bath, and t-butyl cinnamyl carbonate (110 mg, 0.467 mmol) was added to the reaction mixture by syringe. The reaction mixture was slowly warmed to room temperature over 4 h and carefully monitored by GC and TLC. After the reaction was complete (12 h), the crude mixture was passed through a pad of silica gel, eluting with 10% EtOAc in hexanes and concentrated. The ratio of regioisomers was determined by $^1$H NMR analysis of this mixture. The mixture was then purified by flash column chromatography on silica gel (1.5% ethyl acetate in hexanes) to give the desired product (61 mg, 85%). HPLC analysis indicated that the enantiomeric excess of product was 95% [Diacel CHIRALCEL OD-H (0.46 cm×25 cm); hexanes/2-propanol=99.95/0.05; flow rate=0.6 mL/min; detection wavelength=220 nm; Tr=9.6 (major), 10.3 (minor) min]. I-Ethoxy-1-phenyl-2-propene: $^1$H NMR (400.13 MHz, CDCl$_3$) δ 7.44-7.24 (m, 5H), 5.94 (ddd, J=16.8, 10.4, 6.4 Hz, 1H), 5.25 (dt, J=17.2, 1.2 Hz, 1H), 5.17 (dt, J=10.0, 1.2 Hz, 1H), 4.73 (d, J=7.6 Hz, 1H), 3.52 (quintet, J=7.2 Hz, 1H), 3.43 (quintet, J=7.2 Hz, 1H), 1.12 (t, J=7.2 Hz, 1H).

General Procedure for Reaction with Secondary and Tertiary Alkoxides.

In a drybox, LiOCH(CHMe$_2$)$_2$ (120 mg, 1.00 mmol) and CuI (200 mg, 1.05 mmol) in THF (1.0 mL) were stirred for 30 min. A THF solution (1.0 mL) of [Ir(COD)Cl]$_2$ (6.7 mg, 0.010 mmol) and (Ra,Rc,Rc)-Ligand L4 (12.8 mg, 0.020 mmol) was then added. Following the general procedure described for reactions of primary alkoxides, the product was obtained after 16 h of reaction time as a colorless liquid (96 mg, 86%, B/L=99/1). 1-[2-Methyl-1-(1-methylethyl)propoxy]-1-phenyl-2-propene: $^1$H NMR (400.13 MHz, CDCl$_3$) δ 7.32-7.15 (m, 5H), 5.83 (ddd, J=17.2, 10.0, 6.0 Hz, 1H), 5.18 (dt, J=17.2, 1.2 Hz, 1H), 5.10 (dt, J=10.4, 1.3 Hz, 1H), 4.74 (d, J=7.6 Hz, 1H), 2.95 (t, J=5.2 Hz, 1H), 1.85-1.73 (m, 2H), 0.90 (d, J=4.4 Hz, 3H), 0.88 (d, J=4.4 Hz, 3H), 0.77 (d, J=6.8 Hz, 3H), 0.74 (d, J=6.8 Hz, 3H). Anal Calcd. For C$_{16}$H$_{24}$O: C, 82.70; H, 10.41. Found: C, 82.49; H, 10.47. To measure the enantiomeric excess of the products from reactions with secondary and tertiary alkoxides, the olefin of this allyl ether was converted to the terminal alcohol by hydroboration. Thus, a portion of the allylic ether product (46 mg, 0.20 mmol) was dissolved in THF (0.5 mL), cooled to 0° C., and treated with BH$_3$.THF (1.0 M, 0.15 mL, 0.30 mmol). After 1 h, H$_2$O (0.10 mL) was added, and the reaction was stirred for another 30 min before adding aqueous NaOH (20 wt %, 0.2 mL) and aqueous H$_2$O$_2$ (30 wt %, 0.1 mL). The reaction was then warmed to room temperature over 1 h and saturated with K$_2$CO$_3$ and washed with CH$_2$Cl$_2$ (3×5 mL). The combined organic layer was washed with brine (2×10 mL), dried over Na$_2$CO$_3$, concentrated, and purified by chromatography (SiO$_2$, 12% EtOAc in hexanes) to give the alcohol. HPLC analysis indicated that the enantiomeric excess of the alcohol was 95% [Diacel CHIRALCEL OJ (0.46 cm×25 cm); hexanes/2-propanol=90/10; flow rate=0.5 mL/min; detection wavelength=210 nm; Tr=7.7 (minor), 8.7 (major) min].

The other secondary and teritiary ethers were prepared similarly and characterized by $^1$H NMR spectroscopy. The ee's of these materials were also measured from the corresponding alcohols prepared via the hydroboration and oxidation as described for the product from reaction of LiOCH(CHMe$_2$)$_2$.

Enantioselective Allylic Amination Catalyzed by Complex Ir-1 or the combination of [(COD)IrCl]$_2$ and L1 (FIG. 2 (+ symbols) and Table 8, Entry 2): In a drybox, [(COD)IrCl]$_2$ (6.7 mg, 0.010 mmol) and L1 (S$_a$,S$_c$,S$_c$) (10.8 mg, 0.020 mmol) or [(COD)IrCl(L1)] (Ir-1) (17.5 mg 0.0200 mmol) were dissolved in 0.5 mL of THF in a screw-capped vial. Dodecane (50.0 µl, 37.5 mg, 0.220 mmol) was added as internal standard. A small magnetic stirbar was added, and the vial was sealed with a cap containing a PTFE septum and removed from the drybox. Benzylamine (135 mg, 1.26 mmol) and methyl cinnamyl carbonate (192 mg, 1.00 mmol) were added to the reaction mixture by syringe. The reaction mixture was stirred at room temperature for 10 h and monitored by GC.

General Procedure for isolation of (+)-N-(1-phenyl-2-propenyl)benzylamine: After the above reaction was judged complete by GC, the volatile materials were evaporated. A $^1$H NMR spectrum of the crude reaction was obtained, and this spectrum showed that the ratio of branched regioisomer to linear regioisomer to diallylation product was 98/1/1. The mixture was purified by flash column chromatography on silica gel (2.5% ethyl acetate in pentane) to give (+)-N-(1-phenyl-2-propenyl)benzylamine (180 mg, 84%). HPLC analysis indicated that the enantiomeric excess of the product was 95% [Daicel Chiralcel® OD-H (0.46 cm×25 cm); hexane/2-propanol/diethylamine=99.74/0.25/0.01; flow rate=0.6 mL/min; detection wavelength=220 nm; TR=15.1 (minor) min, 17.4 (major)]. $^1$H NMR (400.13 MHz, CDCl$_3$) δ 7.30-7.39 (m, 8H), 7.22-7.28 (m, 2H), 5.95 (ddd, J=16.8, 10.0, 7.2 Hz, 1H), 5.23 (dt, J=16.8, 1.6 Hz, 1H), 5.12 (dq, J=10.0, 0.8 Hz, 1H), 4.23 (d, J=7.2 Hz, 1H), 3.75 (d of AB pattern, J=13.4 Hz, 1H), 3.71 (d of AB pattern, J=13.4 Hz, 1H), 1.64 (brs, 1H). $^{13}$C NMR (100.59 MHz, CDCl$_3$) δ 142.7, 140.9, 140.4, 128.5, 128.4, 128.1, 127.3, 127.2, 126.9, 115.2, 65.1, 51.3.

Reaction of benzylamine with methyl cinnamyl carbonate catalyzed by complex Ir-2 and [(COD)IrCl]$_2$ (FIG. 2, squares and Table 8, Entry 1): In a drybox, [(COD)Ir(κ$^2$-L1)L1] (Ir-2) (13.8 mg, 0.0100 mmol) and [(COD)IrCl]$_2$ (3.4 mg, 0.0050 mmol) were dissolved in 0.5 mL of THF in a screw-capped vial. Dodecane (50.0 µL, 37.5 mg, 0.220 mmol) was added as internal standard. A small magnetic stirbar was added, and the vial was sealed with a cap containing a PTFE septum and removed from the drybox. Benzylamine (135 mg, 1.26 mmol) and methyl cinnamyl carbonate (192 mg, 1.00 mmol) were added to the reaction mixture by syringe. The reaction mixture was stirred at room temperature for 10 h and monitored by GC. After the above reaction was judged complete by GC, the volatile materials were evaporated. $^1$H NMR analysis of the residual crude mixture indicated that the ratio of regioisomers and diallylation product was 98/1/1. The product was purified by the general procedure, and HPLC analysis of the purified product indicated that the enantiomeric excess was 97.2%.

Reaction of benzylamine with methyl cinnamyl carbonate catalyzed by complex Ir-2 (FIG. 2, circles): By the procedure for reaction of the combination of Ir-2 and [(COD)IrCl]$_2$, but with only [(COD)Ir(κ$^2$-L1)L1] (2) (13.8 mg, 0.0100 mmol) as catalyst, the reaction of benzylamine (135 mg, 1.26 mmol) and methyl cinnamyl carbonate (192 mg, 1.00 mmol) was monitored by GC for 10 h. $^1$H NMR analysis of the crude reaction showed the ratios of products to be 98/1/1, and after purification of the product by the general procedure, HPLC analysis indicated that the enantiomeric excess of the major product was 97.3%.

Reaction of benzylamine with methyl cinnamyl carbonate catalyzed by Complex Ir-3 and [(COE)$_2$IrCl]$_2$ (FIG. 2, triangles): By the procedure for reaction of the combination of Ir-2 and [(COD)IrCl]$_2$, the reaction of benzylamine (135 mg, 1.26 mmol) and methyl cinnamyl carbonate (192 mg, 1.00 mmol) catalyzed by [(COD)Ir(κ$^2$-L1)(PPh$_3$)] (Ir-3) (11.0 mg, 0.0100 mmol) and [(COE)$_2$IrCl]$_2$ (4.4 mg, 0.0050 mmol) was monitored by GC for 10 h. $^1$H NMR analysis of the crude reaction showed the ratios of products to be 98/1/1, and after purification of the product by the general procedure, HPLC analysis as described above indicated that the enantiomeric excess of the major product was 97.2%.

(−)-1-(1-Phenyl-2-propenyl)diphenylmethylamine (Table 8, Entry 3): By the procedure for reaction of benzylamine with methyl cinnamyl carbonate, the reaction of aminodiphenylmethane (0.240 mL, 255 mg, 1.390 mmol) and methyl cinnamyl carbonate (0.188 g, 0.979 mmol) catalyzed by [(COD)Ir(κ$^2$-L1)L1] (Ir-2) (13.8 mg, 0.0100 mmol) and [(COD)IrCl]$_2$ (3.4 mg, 0.0050 mmol) was conducted in 1.5 mL THF. After 10 h at room temperature, the $^1$H NMR spectrum of the reaction mixture indicated that the ratio of branched to linear isomer was 97/3. After purification by flash chromatography (silica gel, 2% ethyl acetate in hexanes), the product was isolated as a colorless oil (250 mg, 85%), [α]$^D_{RT}$=−35.0 (c=1.10, CHCl$_3$). $^1$H NMR analysis of its salt with (+)-camphorsulfonic acid indicated an enantiomeric excess of 98%. $^1$H NMR (400.13 MHz, CDCl$_3$) δ 7.32-7.04 (m, 15H), 5.83 (ddd, J=17.2, 10.4, 6.8 Hz, 1H), 5.07 (dt, J=10.8, 1.2 Hz, 1H), 5.04 (dq, J=3.6, 1.2 Hz, 1H), 4.73 (s, 1H), 4.01 (d, J=6.8 Hz, 1H), 1.77 (s, 1H); $^{13}$C NMR (100.5 MHz, CDCl$_3$) δ 144.0, 143.8, 142.7, 140.5, 128.4, 128.4, 128.4, 127.5, 127.4, 127.3, 127.1, 126.9, 126.9, 115.3, 63.3, 62.3. Anal. Calcd. For C$_{22}$H$_{21}$N: C, 88.25; H, 7.07; N, 4.68. Found: C, 87.98; H, 7.04; N, 4.68.

(−)-1-(1-Phenyl-2-propenyl)diphenylmethylamine (Table 8, Entry 4): By the procedure for reaction of benzylamine with methyl cinnamyl carbonate, the reaction of aminodiphenylmethane (0.240 mL, 0.255 g, 1.390 mmol) and methyl cinnamyl carbonate (0.188 g, 0.979 mmol) with [(COD)IrCl]$_2$ (6.7 mg, 0.010 mmol) and L1 (S$_a$,S$_c$,S$_c$) (10.8 mg, 0.020 mmol) as catalyst was conducted in 1.5 mL THF. After 10 h at room temperature, the conversion of (−)-1-(1-Phenyl-2-propenyl)diphenylmethylamine was determined by $^1$H NMR spectroscopy of the crude reaction to be 11%.

(+)-1-(1-Phenyl-2-propenyl)pyrrolidine (Table 8, Entry 5): A stock solution containing [(COD)Ir(η$^2$-L1)(L1)] (Ir-2) (13.8 mg, 0.0100 mmol) and [(COD)IrCl]$_2$ (3.4 mg, 0.0050 mmol) in 1.0 mL of THF was prepared. From this solution, 0.10 mL was added to 0.40 mL of THF in a screw-capped vial with a small magnetic stirbar. Pyrrolidine (87.5 mg, 1.23 mmol) and methyl cinnamyl carbonate (183 mg, 0.950 mmol) were added to the reaction mixture by syringe. The reaction was conducted at room temperature for 10 h. $^1$H NMR analysis of the crude mixture indicated that the ratio of the branched to linear products was 99/1. The mixture was purified by flash column chromatography on silica gel (5% ethyl acetate in hexane) to give 148 mg (81%) of the title compound. HPLC analysis indicated that the enantiomeric excess of product was 98% [Daicel Chiralcel® OD-H (0.46 cm×25 cm); hexane/diethylamine=99.75/0.25; flow rate=0.6 mL/min; detection wave length=220 nm; T$_R$=7.60 (minor), 8.10 (major) min]; =11.2 (major), 12.5 (minor) min]: [α]$^D_{RT}$=+85 (c 3.2, CHCl$_3$); $^1$H NMR (400.13 MHz, CDCl$_3$) δ 7.28-7.37 (m, 4H), 7.20-7.25 (m, 1H), 6.04 (ddd, J=17.2, 10.0, 8.8 Hz,1H), 5.20 (dd, J=17.2, 1.2 Hz, 1H), 5.00 (dd, J=10.0, 1.2 Hz, 1H), 3.58 (d, J=8.8 Hz, 1H), 2.45-2.54 (m, 2H), 2.33-2.42 (m, 2H), 1.76 (m, 4H); $^{13}$C NMR (100.5 MHz, CDCl$_3$) δ 142.7, 141.0, 128.5, 127.6, 127.1, 115.1, 75.2, 53.0, 23.3.

(+)-1-(1-Phenyl-2-propenyl)pyrrolidine (Table 8, Entry 6). A stock solution containing [(COD)IrCl]$_2$ (3.4 mg, 0.0050 mmol) and L1 (10.8 mg, 0.0200 mmol) in 1.0 mL of THF was prepared. By the procedure for reaction of benzylamine with methyl cinnamyl carbonate, the reaction of pyrrolidine (85.0 mg, 1.19 mmol) and methyl cinnamyl carbonate (201.5 mg, 1.049 mmol) was conducted at room temperature for 16 h. $^1$H NMR analysis of the crude mixture showed the ratio of branched to linear product to be 99/1. After purification, 121 mg of the title compound (61%) was isolated and HPLC analysis as described above indicated that the enantiomeric excess of the major product was 97%.

(−)-1-(1-Phenyl-2-propenyl)phenylamine (Table 8, Entry 7). By the procedure for reaction of benzylamine with methyl cinnamyl carbonate, the reaction of aniline (130 mg, 1.40 mmol) and methyl cinnamyl carbonate (188 mg, 0.980 mmol) with [(COD)Ir(κ$^2$-L1)L1] (Ir-2) (13.8 mg, 0.0100 mmol) and [(COD)IrCl]$_2$ (3.4 mg, 0.0050 mmol) as catalyst was conducted at room temperature for 2 h. $^1$H NMR analysis of the crude reaction mixture indicated that the ratio of regioisomers was greater than 99/1. The mixture was then purified by flash column chromatography on silica gel (1.5% ethyl acetate in hexanes) to give 81% yield. HPLC analysis indicated that the enantiomeric excess of the product was 97% [Diacel Chiralcel® OD-H (0.46 cm×25 cm); hexanes/2-propanol=99.75/0.25; flow rate=0.6 mL/min; detection wavelength=254 nm; T$_R$=19.1 (major) min., 20.3 min. (minor)]. [α]$^D_{20}$=−12.0 (c 2.10, CHCl$_3$); $^1$H NMR (400.13 MHz, C$_6$D$_6$) δ 7.44-7.24 (m, 5H), 7.20-7.10 (m, 2H), 6.69 (t, J=7.2 Hz, 1H), 6.60 (d, J=8.0 Hz, 2H), 6.04 (ddd, J=16.8, 10.4, 6.4 Hz, 1H), 5.28 (dt, J=17.2, 1.2 Hz, 1H), 5.22 (dt, J=10.0, 1.2 Hz, 1H), 4.94 (t, J=4.4 Hz, 1H), 4.04 (br s, 1H). $^{13}$C NMR (100.5 MHz, C$_6$D$_6$) δ .61.1 (s, CH), 114.2 (s, CH=CH$_2$), 115.9 (s, CH=CH$_2$), 118.2, 127.7, 127.8, 129.1, 129.6, 139.6 (all s, Ar—CH), 142.4 (s, Ar—C), 147.8 (s, Ar—C).

(−)-1-(1-Phenyl-2-propenyl)phenylamine (Table 8, Entry 8). By the procedure with [(COD)IrCl]$_2$ (6.7 mg, 0.010 mmol) and L1 (S$_a$,S$_c$,S$_c$) (10.8 mg, 0.020 mmol) the reaction of aniline (130 mg, 1.40 mmol) and methyl cinnamyl carbonate (188 mg, 0.980 mmol) was conducted at room temperature for 24 h. $^1$H NMR and GC analysis of the crude reaction mixture showed that the conversion of the reaction was less than 1%.

(+)-1-phenyl-1-phenoxy-2-propene (Table 8, Entry 9): [(COD)Ir(κ$^2$-L1)(L1)] (Ir-2) (13.8 mg, 0.0100 mmol), [(COD)IrCl]$_2$ (3.4 mg, 0.0050 mmol) and sodium phenoxide (232 mg, 2.00 mmol) were dissolved in 1.0 mL of THF. Ethyl cinnamyl carbonate (192 mg, 0.930 mmol) was added to the reaction mixture by syringe. After being stirred at room temperature for 2 h, the reaction mixture was poured into brine, extracted with ether, dried, filtered, and concentrated. $^1$H NMR analysis of the mixture indicated that the ratio of branched to linear regioisomers was 95/5. The residue was purified by flash chromatography on silica gel (1% Et$_2$O/Hexanes) to afford 157 mg (75%) of 1-phenyl-1-phenoxy-2-propene as a viscous oil. [R$_f$ 0.85 (5% Et$_2$O/Hexanes)] HPLC analysis indicated an enantiomeric excess of 94% [Chiralcel® OJ-H column, eluting with 99.75/0.25 hexane/i-PrOH, 0.6 mL/min, 220 nm; major enantiomer T$_R$, 45.4, minor enantiomer T$_R$ 55.3 min]; [α]$^D_{20}$=+8.9 (c 1.4, CHCl$_3$); $^1$H NMR (500.13 MHz, CDCl$_3$) δ 7.48-7.27 (m, 8H), 7.01-6.96 (m, 2H), 6.15 (ddd, J=17.2, 10.4, 5.9 Hz, 1H), 5.70 (d, J=5.9 Hz, 1H), 5.41 (d, J=17.2 Hz, 1H), 5.31 (d, J=10.4 Hz, 1H). $^{13}$C NMR (125.7 MHz, CDCl$_3$) δ 157.9 (C), 140.1 (C), 137.9 (CH), 129.3 (CH), 128.6 (CH), 127.8 (CH), 126.6 (CH), 121.0 (CH), 116.5 (CH$_2$), 116.2 (CH), 80.8 (CH).

(+)-1-phenyl-1-phenoxy-2-propene (Table 1, Entry 10): By the procedure for entry 9 of Table 1, the reaction of sodium phenoxide (232 mg, 2.00 mmol) and ethyl cinnamyl carbonate (192 mg, 0.930 mmol) with [(COD)IrCl]$_2$ (6.7 mg, 0.010 mmol) and L1 (S$_a$,S$_c$,S$_c$) (10.8 mg, 0.0200 mmol) as catalyst was conducted at room temperature for 32 h. $^1$H NMR analysis of the crude reaction showed the ratios of branched to linear products to be 99/1. After purification, 159 mg of the title compound (75%) was isolated. HPLC analysis as described above indicated that the enantiomeric excess of the major product was 94%.

Preparation of [(COD)IrCl(L1)](Ir-1): THF (5 mL) was added to a mixture of [(COD)IrCl]$_2$ (100 mg, 0.150 mmol) and phosphoramidite L1 (162 mg, 0.300 mmol) while stirring at room temperature. Formation of the product [(COD)IrCl(L1)] was determined by $^1$H and $^{31}$P NMR spectroscopy to be complete within 10 min. The solvent was removed under vacuum, and the product was washed three times with 3 mL of pentane. The orange powder was dried under high vacuum overnight. Crystals suitable for X-ray diffraction were obtained by slow diffusion of pentane into a saturated solution of [(COD)IrCl(L1)] (1) in CH$_2$Cl$_2$. Yield: 90% (236 mg). $^1$H-NMR (400.13 MHz, CD$_2$Cl$_2$) δ 0.99 (m, 1H, COD), 1.17 (m, 1H, COD), 1.68 (d, J=7.0 Hz, 6H, CHCH$_3$), 1.70 (m, 3H, COD), 1.87 (m, 1H, COD), 2.22 (m, 2H, COD), 2.40 (m, 1H, COD), 3.21 (m, 1H, COD), 5.25 (m, 3H, CHCH$_3$+COD), 5.46 (m, 1H, COD), 6.79 (d, J=8.6 Hz, 1H, ArH), 7.14 (m, 11H, ArH), 7.23 (d, J=6.5 Hz, 1H, ArH),7.25 (d, J=7.0 Hz, 1H, ArH), 7.32 (d, J=8.5 Hz, 1H, ArH), 7.44 (t, J=8.0 Hz, 1H, ArH), 7.46 (t, J=7.0 Hz, 1H, ArH), 7.88 (d, J=8.8 Hz, 1H, ArH), 7.95 (d, J=8.2 Hz, 1H, ArH), 8.00 (d, J=8.2 Hz, 1H, ArH), 8.10 (m, 2H, ArH); $^{31}$P-NMR (161.9 MHz, CD$_2$Cl$_2$) δ 115.9 (s); $^{13}$C NMR (127.7 MHz, CD$_2$Cl$_2$) δ 22.5 (s, CH$_3$), 28.7 (d, J=3 Hz, CH$_2$), 29.9 (d, J=2.3 Hz, CH$_2$), 33.4 (d, J=2.8 Hz, CH$_2$), 34.0 (d, J=2.8 Hz, CH$_2$), 52.1 (s, CH—COD), 55.6 (d, J=8.7 Hz, CHCH$_3$), 57.8 (s, CH—COD), 101.5 (s, CH—COD), 101.5 (d, J=17.9 Hz, CH—COD), 101.8 (d, J=20.5 Hz, CH—COD), 121.6 (s, Ar—C), 122.1, 125.4, 125.7, 126.4, 126.6, 127.1, 127.3, 127.3, 127.4, 127.8, 128.5, 128.7, 129.3, 130.1, 130.3 (all s, Ar—CH), 123.8 (d, J=4.0 Hz, Ar—C), 131.2, 132.2, 132.7, 133.2 (all s, Ar—C), 142.3 (d, J=3.7 Hz, Ar—C), 149.1 (d, J=4.5 Hz, Ar—C), 150.4 (d, J=14.6 Hz, Ar—C); Anal. Calc. for C$_{44}$H$_{42}$ClIrNO$_2$P: C, 60.37; H, 4.84; N, 1.60. Found: C, 60.37; H, 4.78; N, 1.57.

Figure 3:
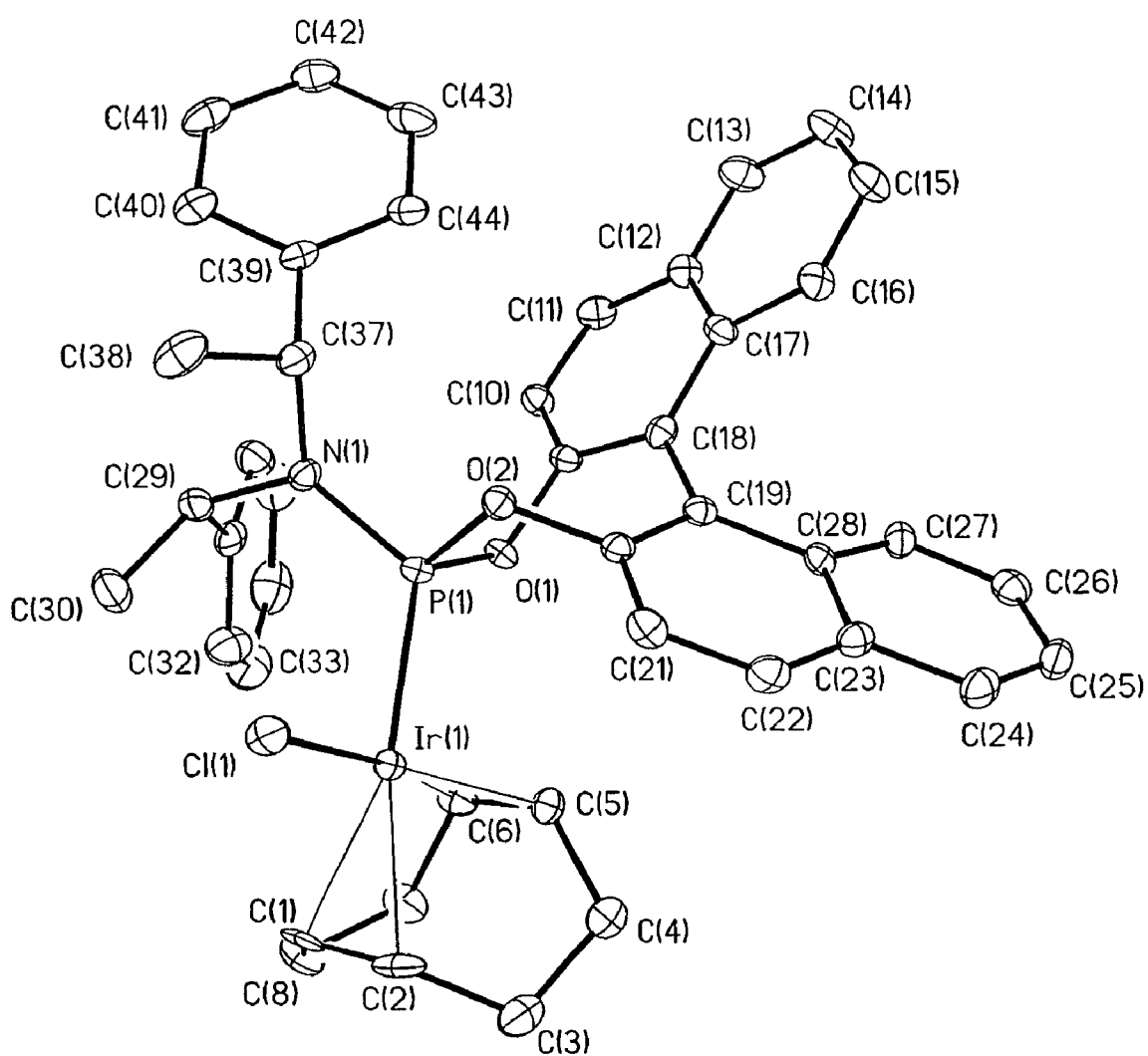
FIG. 3 is an ORTEP drawing of [(COD)IrCl(L1)]

X-Ray Analysis of 1. (FIG. 3) Crystals suitable for X-ray diffraction were obtained by slow diffusion of pentane into a saturated solution of [(COD)IrCl(L1)] (1) in CH$_2$Cl$_2$. An orange block crystal of C$_{44}$H$_{42}$ClIrNO$_2$P having approximate dimensions of 0.30×0.25×0.25 mm was mounted with epoxy cement on the tip of a fine glass fiber. All measurements were made on a Nonius KappaCCD diffractometer with graphite monochromated Mo—Kα radiation. Cell constants and an orientation matrix for data collection corresponded to a primitive triclinic cell with dimensions:

a=11.608(2) Å α=98.34(3)°
b=11.884(2) Å β=103.13(3)°
c=14.130(3) Å γ=105.27(3)°
V=1787.2(6) Å$^3$

For Z=2 and F.W.=875.41, the calculated density is 1.627 g/cm$^3$. Based on a statistical analysis of intensity distribution, and the successful solution and refinement of the structure, the space group was determined to be: P-1 (#2)

The data were collected at a temperature of 183(2) K to a maximum 2θ value of 55.00°. Three omega scans consisting of 62, 62, and 62 data frames, respectively, were collected with a frame width of 1.9° and a detector-to-crystal distance, Dx, of 35 mm. Each frame was exposed twice (for the purpose of de-zingering) for 38 s. The data frames were processed and scaled using the DENZO software package (Z. Otwinowski and W. Minor, "Processing of X-Ray Diffraction Data Collected in Oscillation Mode," Methods in Enzymology, vol. 276: Macromolecular Crystallography, part A, 307-326, 1997, C. W. Carter, Jr. & R. M. Sweet, Eds., Academic Press.) A total of 11298 reflections were collected of which 8103 were unique and observed ($R_{int}$=0.0271). The linear absorption coefficient, μ, for Mo—Kα radiation is 38.95 cm$^{-1}$, and no absorption correction was applied. The data were corrected for Lorentz and polarization effects.

The structure was solved by direct methods and expanded using Fourier techniques (*Acta Cryst. A*46 (1990) 467-473). The non-hydrogen atoms were refined anisotropically, and hydrogen atoms were treated as idealized contributions. The final cycle of full-matrix least-squares refinement (Least Squares function minimized: $\Sigma w(|F_o|-|F_c|)^2$) on F was based on 8103 observed reflections (I>2.00σ(I)) and 451 variable parameters and converged with unweighted and weighted agreement factors of R=Σ||Fo|-|Fc||/Σ|Fo|=0.0335 and $R_w$=$[\Sigma w(|Fo|-|Fc|)^2/\Sigma wFo^2]^{1/2}$=0.0775. The maximum and minimum peaks on the final difference Fourier map corresponded to 1.393 and -1.364 e$^-$/Å$^3$, respectively.

Preparation of [(COD)Ir(κ$^2$-L1)L1] (Ir-2): THF (5 mL) was added to a mixture of [(COD)IrCl(L1)] (1) (100 mg, 0.110 mmol) and phosphoramidite L1 (123 mg, 0.230 mmol) at room temperature. After complete dissolution of the iridium complex, pyrrolidine (391 mg, 460 µl, 5.50 mmol) was added by syringe, and the solution was stirred overnight. The color of the solution changed from orange to yellow, and a precipitate of the pyrrolidine hydrochloride was observed. The solvent was evaporated under vacuum, and the yellow residue was suspended in a mixture of 2 mL diethyl ether and 2 mL benzene. This suspension was filtered through a 0.45 µm nylon syringe filter. The solvent was evaporated under vacuum, and the yellow product was dissolved in 0.5 mL CH$_2$Cl$_2$ and precipitated by layering with pentane at -30° C. to yield a fine yellow powder, which was dried under high vacuum overnight. Yield: 85% (129 mg). $^1$H NMR (400.13 MHz, CD$_2$Cl$_2$, 248 K): δ -0.66 (dt, J=11.8, 6.0 Hz, 1H, IrCH$_2$), 0.32 (br s, 3H, CH$_3$), 0.92 (d, J=6.8 Hz, 3H, CH$_3$), 1.37 (d, J=6.5 Hz, 3H, CHCH$_3$), 1.67 (m, 1H, COD), 1.73 (dt, J=18.6, 11.3 Hz, 1H, IrCH$_2$), 1.93 (m, 2H, COD), 2.32 (m, 2H, COD), 2.45 (m, 2H, COD), 2.71 (m. 1H, COD), 2.91 (m 2H, COD), 3.28 (dd, J=6.9 Hz, J=7.1 Hz, 1H, CHCH$_2$Ir), 3.75 (m, 1H, CHCH$_3$), 3.81 (m, 1H, COD), 4.54 (m, 1H, CHCH$_3$), 4.69 (m, 1H, COD), 5.11 (m, 1H, CHCH$_3$), 5.85 (d, J=7.2 Hz, 1H, ArH), 6.50 (d, J=9.5 Hz, 1H, ArH), 6.55 (t, J=12.6 Hz, 2H, ArH), 6.92 (m, 4H, ArH), 6.92 (d, J=7.0 Hz, 1H, ArH), 7.08 (m, 2H, ArH), 7.13 (m, 3H, ArH), 7.17-7.26 (m, 13H, ArH), 7.32 (m, 4H, ArH), 7.40 (m, 2H, ArH), 7.49 (t, J=8.7 Hz, 1H, ArH), 7.64 (d, J=8.6 Hz, 1H, ArH), 7.73 (d, J=8.7 Hz, 2H, ArH), 7.83 (d, J=8.5 Hz, 1H, ArH), 7.87 (d, J=8.7 Hz, 1H, ArH), 7.92-8.06 (m, 5H, ArH), 8.13 (d, J=8.6 Hz, 1H, ArH); $^{31}$P NMR (161.9 MHz, CD$_2$Cl$_2$) δ 152.6 (d, J=46.3 Hz, 1P), 127.8 (d, J=46.2 Hz, 1P) main diastereomer (94%), 149.4 (d, J=77.8 Hz, 1P), 146.0 (d, J=78.0 Hz, 1P) minor diastereomer (6%); Aliphatic region of the $^{13}$C NMR spectrum (125.7 MHz, CD$_2$Cl$_2$, 248K) δ 15.2 (dd, J=4.9 Hz, J=5.8 Hz, IrCH$_2$), 20.1 (s, CH$_3$), 21.9 (s, CH$_3$), 24.1 (s, CH$_3$), 23.7 (br s, CH$_2$—COD), 29.7 (br s, CH$_2$—COD), 34.3 (br s, CH$_2$—COD), 44.0 (s, CH$_2$—COD), 45.7 (m, CH—COD), 46.2 (m, CH—COD), 53.9 (s, CH), 54.7 (d, J=24.7 Hz, CH), 59.0 (br s, CH), 68.3 (d, J=43.9 Hz, CHCH$_2$), 69.8 (s, CH—COD), 82.6 (s, CH—COD); MS (FAB$^+$) (%): m/z=1378.1 [M$^+$] (8), 838.2 [M+-C$_{36}$H$_{30}$PO$_2$N] (100), 730.2 [M+-L1-C$_8$H$_{12}$] (69); Anal.

Calc. for C$_{80}$H$_{71}$IrN$_2$O$_4$P$_2$: C, 69.70; H, 5.19; N, 2.03; P, 4.49; Cl, 0.00. Found: C, 69.55; H, 5.35; N, 2.09; P, 4.36, Cl<0.02.

Preparation of [(COD)Ir(κ$^2$-L1)PPh$_3$] (Ir-3). [Ir(COD)Cl(L1)] (1) (100 mg, 0.110 mmol) was dissolved in 5 mL of THF at room temperature. Pyrrolidine (391 mg, 460 µl, 5.5 mmol) was added to the stirred solution with a syringe, and the solution was stirred overnight. The color of the solution changed from orange to yellow, and precipitation of the pyrrolidine hydrochloride was observed. To this suspension was added a solution of PPh$_3$ (61 mg, 0.230 mmol) in 2 mL of THF, and the mixture were allowed to stir for 6 h at room temperature. The solvent was evaporated under vacuum, and the yellow residue was suspended in a mixture of 2 mL of diethyl ether and 2 mL of benzene. The suspension was filtered through a 0.45 µm nylon syringe filter. The solvent was evaporated under vacuum, and the yellow product was dissolved in 0.5 mL of CH$_2$Cl$_2$ and layered with pentane at -30° C. to yield pale yellow crystals, which were dried under high vacuum overnight. Yield: 85% (103 mg). $^1$H NMR (400 MHz, THF-d$_8$) major isomer: δ 0.17 (d, J=7.4 Hz, 3H, CH$_3$), 0.70 (m, 1H, COD), 1.11 (dt, J=11.3 Hz, 6.5 Hz, 1H, IrCH$_2$), 1.11 (m, 1H, COD), 1.44 (m, 2H, COD), 1.88 (m, 1H, COD), 1.95 (dt, J=17.6 Hz, 11.4 Hz, 1H, IrCH$_2$), 2.29 (m, 1H, COD), 2.55 (m, 2H, COD), 2.72 (m, 1H, COD), 3.12 (m, 1H, COD), 3.31 (m, 1H, COD), 3.84 (m, 1H, CHCH$_2$Ir), 3.89 (m, 1H, CHCH$_3$), 5.35 (m, 1H, COD), 6.73 (m, 1H, ArH), 6.87 (m, 5H, ArH), 6.95 (d, J=7.2 Hz, 2H, ArH), 7.01 (m, 1H, ArH), 7.05 (m, 1H, ArH), 7.09 (m, 3H, ArH), 7.16 (m, 2H, ArH), 7.23 (m, 3H, ArH), 7.34 (m, 8H, ArH), 7.39 (m, 4H, ArH), 7.54 (d, J=8.4 Hz, 2H, ArH), 7.60 (m, 2H, ArH), 7.88 (d, J=8.0 Hz, 1H, ArH), 8.01 (d, J=8.8 Hz, 1H, ArH), 8.08 (d, J=8.8 Hz, 2H, ArH), 8.16 (d, J=8.8 Hz, 1H, ArH); $^{31}$P NMR (161.9 MHz, d$^8$-THF) δ 152.1 (d, J=20.1 Hz, 1P), 6.6 (d, J=20.5 Hz, 1P) major diastereomer (84%), 148.0 (d, J=48.1 Hz, 1P), 2.3 (d, J=48.7 Hz, 1P) minor diastereomer (16%); Aliphatic region of the $^{13}$C NMR spectrum (125.7 MHz, THF-d$_8$): δ 17.8 (dd, J=10.2 Hz, J=3.7 Hz, Ir—CH$_2$), 21.2 (s, CH$_3$), 28.6 (d, J=7.8 Hz, CH$_2$—COD), 32.7 (d, J=3.6 Hz, CH$_2$—COD), 35.7 (s, CH$_2$—COD), 36.4 (d, J=7.7 Hz, CH$_2$—COD), 51.5 (dd, J=31.4 Hz, J=8.0 Hz, CH—COD), 61.1 (d, J=5.8 Hz, CHCH$_3$), 70.3 (dd, J=44 Hz, J=5.4 Hz, CHCH$_2$), 70.4 (s, CH—COD), 78.6 (s, CH—COD); Anal. Calc. for C$_{62}$H$_{56}$IrNO$_2$P$_2$.1.1CH$_2$Cl$_2$: C, 63.44; H, 4.91; N, 1.17. Found: C, 63.25; H, 4.98; N, 1.19.

Preparation of [(COD)Ir(κ$^2$-L1)PMe$_3$] (Ir-4): [(COD)Ir(κ$^2$-L1)PPh$_3$] (3) (55 mg, 0.050 mmol) was dissolved in 3 mL of THF at room temperature and cooled to -30° C. PMe$_3$ (50 µl of a 1 M solution in THF, 0.050 mmol) was added to this stirred solution with a syringe, and the resulting solution was stirred for 30 min at -30° C. The solvent was evaporated under vacuum, and the yellow residue was washed three times with 2 mL of pentane that was cooled to -30° C. The white product was recrystallized from a mixture of CH$_2$Cl$_2$ and pentane (1:5) at -30° C. to give clear crystals. Crystals suitable for X-ray diffraction were obtained by slow diffusion of pentane into a saturated solution of [(COD)Ir(κ$^2$-L1)PMe$_3$] (4) in CH$_2$Cl$_2$. Yield: 90% (42 mg). $^1$H NMR (400 MHz, CD$_2$Cl$_2$): δ 0.25 (d, J=10.5 Hz, 1H, IrCH$_2$), 1.41 (d, J=6.8 Hz, 3H, CH$_3$), 1.73 (d, J=7.3 Hz, 9H, P(CH$_3$)$_3$), 1.76 (m, 3H, COD), 1.88 (m, 1H, COD), 1.95 (m, 1H, COD), 2.17 (m, 4H, COD), 2.21 (dd, J=10.6 Hz, 10.5 Hz, 1H, IrCH$_2$), 3.34 (m, 1H, COD), 3.49 (m, 1H, COD), 4.39 (dq, J=6.8 Hz, J=11.5 Hz, 1H, CHCH$_3$), 4.58 (dd, J=37.5 Hz, J=9 Hz, CHCH$_2$Ir), 6.91-6.99 (m, 5H, Ar—H), 7.06 (t, J=7.6 Hz, 1H, Ar—H), 7.14 (t, J=7.6 Hz, 2H, Ar—H), 7.30 (m, 2H, Ar—H), 7.38-7.50 (m, 5H, Ar—H), 7.54 (br s, 1H, Ar—H), 7.86 (d, J=8.4 Hz, 1H, Ar—H), 7.98 (m, 3H, Ar—H), 8.09 (d, J=8.8 Hz, 2H, Ar—H); $^{31}$P NMR (161.9 MHz, CD$_2$Cl$_2$) δ 149.1 (d, J=47.1 Hz, 1P), −57.3 (d, J=45.5 Hz, 1P); $^{3}$C NMR (100.5 MHz, CD$_2$Cl$_2$) δ 17.7 (dd, Hz, J=26.1 Hz, J=3.1 Hz, P(CH$_3$)$_3$), 18.2 (t, J=5.7 Hz, Ir—CH$_2$), 20.4 (s, CH$\underline{C}$H$_3$), 31.9 (d, J=11.3 Hz, COD), 34.7 (s, COD), 34.7 (s, COD), 35.3 (d, J=3.9 Hz, COD), 49.8 (dd, J=50.0 Hz, J=7.5 Hz, CH—COD), 55.1 (dd, J=26.4 Hz, J=7.0 Hz, CH—COD), 55.4 (d, J=4.5 Hz, $\underline{C}$HCH$_3$), 63.1 (d, J=41.4, IrCH$_2\underline{C}$H), 72.4 (s, CH—COD), 77.7 (s, CH—COD), 122.6 (s, 1C, Ar—C), 122.5 (s, 1C, Ar—CH), 123.5 (s, 1C, Ar—CH), 124.3 (s, 1C, Ar—C), 124.8 (s, 1C, Ar—CH), 125.0 (s, 1C, Ar—CH), 125.2 (s, 1C, Ar—CH), 126.3 (s, 2C, Ar—CH), 126.6 (s, 1C, Ar—CH), 127.0 (s, 2C, Ar—CH), 127.2 (s, 2C, Ar—CH), 127.3 (s, 3C, Ar—CH), 127.4 (s, 1C, Ar—CH), 128.6 (s, 1C, Ar—CH), 128.7 (s, 1C, Ar—CH), 129.2 (s, 2C, Ar—CH), 129.5 (s, 1C, Ar—CH), 130.2 (s, 1C, Ar—CH), 131.0 (s, 1C, Ar—C), 131.3 (s, 1C, Ar—C), 133.2 (s, 1C, Ar—C), 133.4 (s, 1C, Ar—C), 142.6 (s, 1C, Ar—C), 150.0 (d, J=4.0 Hz, 1C, Ar—C), 150.1 (s, 1C, Ar—C), 151.5 (d, J=14.9 Hz, 1C, Ar—C); Anal. Calc. for C$_{47}$H$_{50}$IrNO$_2$P$_2$: C, 61.69; H, 5.51; N, 1.53. Found: C, 61.44; H, 5.40; N, 1.48.

Figure 4:
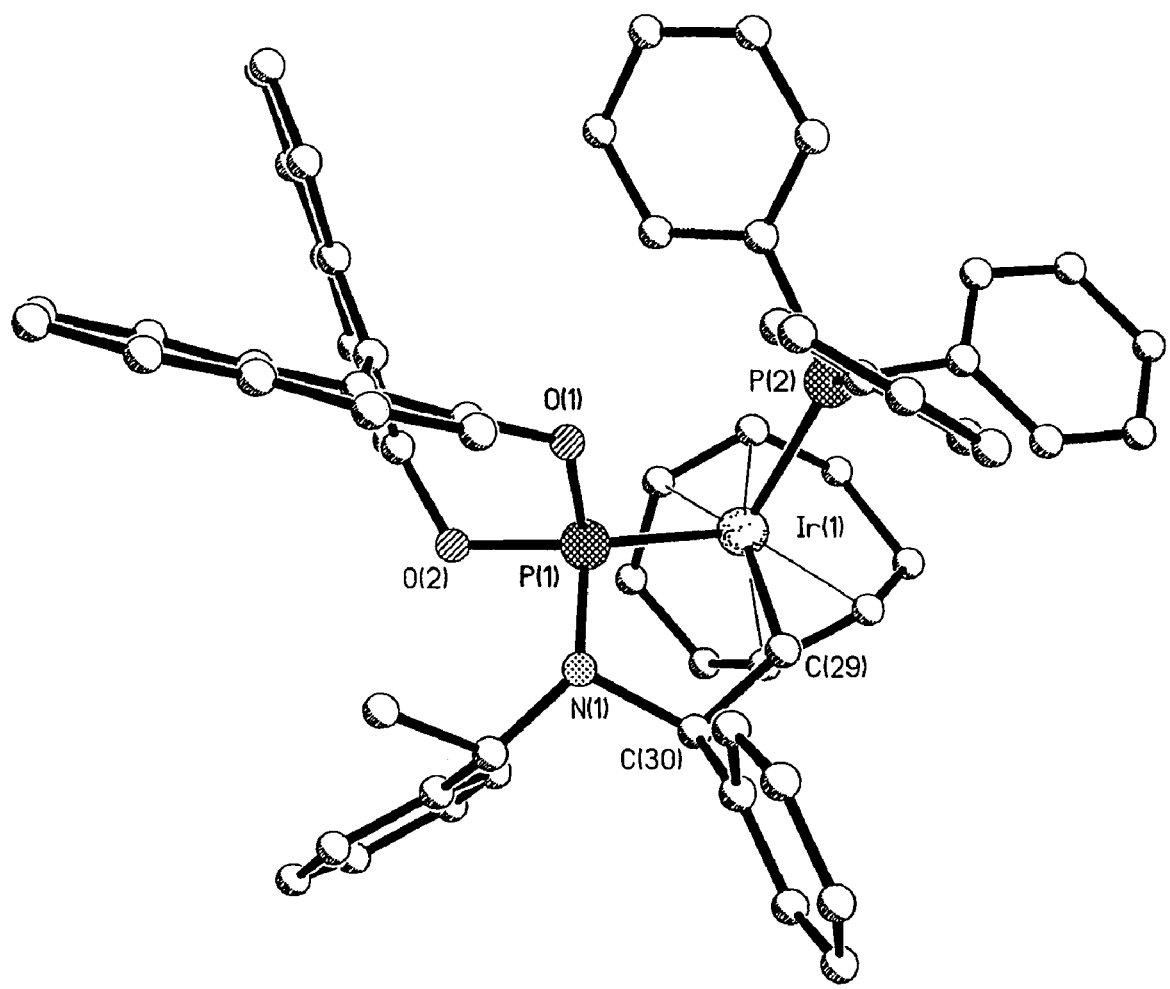
FIG. 4 is a PLUTO drawing of the major diastereomer of [(COD)Ir(κ$^2$-L1)PPh$_3$] determined from an X-ray structural analysis.

X-ray structural analysis of [(COD)Ir(κ$^2$-L1)PMe$_3$] (FIG. 4). Crystals suitable for X-ray diffraction were obtained by slow diffusion of pentane into a saturated solution of [(COD)Ir(κ$^2$-L1)PMe$_3$] (4) in CH$_2$Cl$_2$. A colorless block crystal of C$_{47}$H$_{50}$IrNO$_2$P$_2$ having approximate dimensions of 0.30×0.20×0.20 mm was mounted with epoxy cement on the tip of a fine glass fiber. All measurements were made on a Nonius KappaCCD diffractometer with graphite monochromated Mo—Kα radiation. Cell constants and an orientation matrix for data collection corresponded to a primitive orthorhombic cell with dimensions:

a=10.150(2) Å α=90°
b=19.125(4) Å β=90°
c=20.818(4) Å γ=90°
V=4041.3(14) Å$^3$

For Z=4 and F.W.=915.02, the calculated density is 1.504 g/cm$^3$. Based on a statistical analysis of intensity distribution, and the successful solution and refinement of the structure, the space group was determined to be: P2$_1$2$_1$2, (#19)

The data were collected at a temperature of 173(2) K to a maximum 2θ value of 56.54°. Three omega scans consisting of 54, 54, and 35 data frames, respectively, were collected with a frame width of 1.4° and a detector-to-crystal distance, Dx, of 35.0 mm. Each frame was exposed twice (for the purpose of de-zingering) for a total of 14 seconds. The data frames were processed and scaled using the DENZO software package as described above. A total of 9647 reflections were collected of which 9647 were unique and observed (R$_{int}$=0.000, Friedel pairs not merged). The linear absorption coefficient, μ, for Mo—Kα radiation is 34.22 cm$^{-1}$, and no absorption correction was applied. The data were corrected for Lorentz and polarization effects.

The structure was solved by direct methods and expanded using Fourier techniques as described above. The non-hydrogen atoms were refined anisotropically, and hydrogen atoms were treated as idealized contributions. The final cycle of full-matrix least-squares refinement on F was based on 9647 observed reflections (I>2.00σ(I)) and 478 variable parameters and converged with unweighted and weighted agreement factors of R=||Fo|−|Fc||/Σ|Fo|=0.0371 and R$_w$={Σ[w(F$_o^2$−F$_c^2$)$^2$]/[w(F$_o^2$)$^2$]}$^{1/2}$=0.0685. The maximum and minimum peaks on the final difference Fourier map corresponded to 0.588 and −1.057 e$^-$/Å$^3$, respectively.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. An activated catalyst, comprising a cyclometallated phosphoramidite having the structure

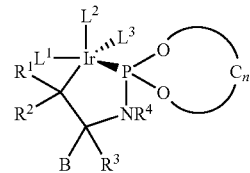

wherein:
O—C$_n$—O is an aliphatic or aromatic diolate;
B is any substituted or unsubstituted aryl or heteroaryl group;
R$^1$, R$^2$, R$^3$, and R$^4$ are independently selected from hydrogen, alkyl, benzylic and aromatic or heteroaromatic groups;
L$^1$ and L$^2$ are any ligands bound to Ir through an electron pair or through electrons in a pi-system of an unsaturated moiety; and
L$^3$ is an optional ligand selected from the group consisting of phosphine, phosphite, phosphoramidite, amine, heterocycle, carbon monoxide, and combinations thereof.

2. The activated catalyst of claim 1, wherein R$^1$, R$^2$, R$^3$, and R$^4$ are independently selected from methyl, benzyl, phenethyl, diphenylmethyl, and phenyl.

3. The activated catalyst of claim 1, wherein L$^1$ and L$^2$ are independently selected from dioolefins, monoolefins, diphosphines, monophosphines, diamines, monoamines, diheterocyclic units, and heterocyclic units.

4. A method of making an activated catalyst, said activated catalyst comprising a cyclometallated phosphoramidite according to claim 1, comprising the step of:
combining a catalyst precursor and a phosporamadite ligand in the presence of a base under conditions that form said activated catalyst.

* * * * *